(12) United States Patent
Davis et al.

(10) Patent No.: US 9,440,084 B2
(45) Date of Patent: Sep. 13, 2016

(54) PROGRAMMING POSTURE RESPONSIVE THERAPY

(75) Inventors: Jon P. Davis, St. Michael, MN (US); Dennis M. Skelton, Bloomington, MN (US); Shyam Gokaldas, New Brighton, MN (US); Rajeev Sahasrabudhe, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 2215 days.

(21) Appl. No.: 12/433,551

(22) Filed: Apr. 30, 2009

(65) Prior Publication Data

US 2010/0010585 A1 Jan. 14, 2010

Related U.S. Application Data

(60) Provisional application No. 61/080,070, filed on Jul. 11, 2008.

(51) Int. Cl.
*A61N 1/36* (2006.01)
*A61N 1/372* (2006.01)
(Continued)

(52) U.S. Cl.
CPC ....... *A61N 1/37247* (2013.01); *A61N 1/36132* (2013.01); *A61N 1/36135* (2013.01); *G06F 19/3406* (2013.01); *G06F 19/3418* (2013.01); *A61B 5/1116* (2013.01); *A61B 5/1118* (2013.01); *A61B 2562/0219* (2013.01);
(Continued)

(58) Field of Classification Search
USPC .................................................. 607/59, 62
See application file for complete search history.

(56) References Cited

U.S. PATENT DOCUMENTS

| | | | |
|---|---|---|---|
| 4,297,685 A | 10/1981 | Brainard, II | |
| 4,365,633 A | 12/1982 | Loughman | |

(Continued)

FOREIGN PATENT DOCUMENTS

| | | |
|---|---|---|
| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Allen Porter, Jr.
(74) *Attorney, Agent, or Firm* — Shumaker & Sieffert, P.A.

(57) ABSTRACT

A programming session for an implantable medical device that includes a posture responsive therapy mode includes at least two phases. In a first phase, a first set of therapy parameter values are modified while the posture responsive therapy mode is deactivated. In the posture responsive therapy mode, the medical device automatically selects one or more therapy parameter values that define therapy delivered to a patient based on a detected posture state. In a second phase, the posture responsive therapy mode is activated and a second set of therapy parameter values are adjusted after observing a patient response to the posture responsive therapy delivered with the first set of therapy parameter values selected during the first phase. The second set of therapy parameter values may, for example, define the patient posture states or the modification profiles with which the medical device adjusts therapy upon detecting a posture state transition.

27 Claims, 24 Drawing Sheets

(51) Int. Cl.
  *G06F 19/00* (2011.01)
  *A61B 5/11* (2006.01)
  *A61N 1/365* (2006.01)
(52) U.S. Cl.
  CPC ...... *A61N 1/36071* (2013.01); *A61N 1/36542* (2013.01); *G06F 19/345* (2013.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |

(56) References Cited

U.S. PATENT DOCUMENTS

| | | |
|---|---|---|
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0253174 A1 | 11/2006 | King |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 | 6/2007 | Bourget et al. |
| 2007/0150029 A1 | 6/2007 | Bourget et al. |
| 2007/0213789 A1 | 9/2007 | Nolan et al. |

(56) References Cited

U.S. PATENT DOCUMENTS

| | | |
|---|---|---|
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products. Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

(56) References Cited

OTHER PUBLICATIONS

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare 10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp., 2008.
Smith et al., "How do sleep disturbance and chronic pain interrelate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/48228: International Search Report and Written Opinion dated Sep. 4, 2009, 16 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.

(56) References Cited

OTHER PUBLICATIONS

U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

PROGRAMMING POSTURE RESPONSIVE THERAPY

This application claims the benefit of U.S. Provisional Application No. 61/080,070 to Skelton et al., entitled, "MODIFICATION PROFILES FOR POSTURE-RESPONSIVE THERAPY" and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure describes techniques for programming posture responsive therapy delivered by an implantable medical device. The techniques are applicable to electrical stimulation therapy or other therapies, such as therapy comprising the delivery of a therapeutic agent. The techniques described herein include testing posture responsive therapy features of a medical device during a programming session.

In one example, the disclosure is directed to a method comprising programming one or more therapy parameters of a medical device during a programming session while the medical device is in a first mode, during the programming session, activating a second mode of the medical device to deliver posture responsive therapy to a patient, wherein the posture responsive therapy is suspended while the medical device is in the first mode, and programming one or more therapy parameters of the medical device based on efficacy of the posture responsive therapy delivered to the patient while the second mode of the medical device is activated.

In another example, the disclosure is directed to a system comprising a medical device and a processor. The medical device includes a first mode and a second mode in which the medical device automatically delivers posture responsive therapy to a patient, wherein the posture responsive therapy is suspended when the medical device is in the first mode. During a programming session, the processor programs one or more therapy parameters of the medical device while the medical device is in the first mode, activates the second mode of the medical device to activate posture responsive therapy delivery to the patient, and programs one or more therapy parameters of the medical device based on efficacy of the posture responsive therapy delivered to the patient while the second mode of the medical device is activated.

In another example, the disclosure is directed to a system comprising means for programming one or more therapy parameters of a medical device during a programming session while the medical device is in a first mode, means for activating a second mode of the medical device to deliver posture responsive therapy to a patient during the programming session, wherein the posture responsive therapy is suspended while the medical device is in the first mode, and means for programming one or more therapy parameters of the medical device based on efficacy of the posture responsive therapy delivered to the patient while the second mode of the medical device is activated.

In another example, the disclosure is directed to a method comprising receiving input selecting a first therapy parameter value of a medical device while the medical device is in a first mode, wherein the medical device includes a second mode in which the medical device automatically delivers posture responsive therapy to a patient and the first mode in which the posture responsive therapy mode is suspended, transmitting a first signal to the medical device that causes the medical device to deliver therapy according to the first therapy parameter value, transmitting a second signal to the medical device that activates the posture responsive therapy mode of the medical device during the programming session, transmitting a third signal to the medical device that causes the medical device to deliver posture responsive therapy to the patient according to a second therapy parameter value, and, during the programming session, modifying the second therapy parameter value based on an efficacy of the posture responsive therapy delivered to the patient.

In another example, the disclosure is directed to a computer-readable storage medium comprising instructions. The instructions cause a programmable processor to perform any of the techniques described herein. The instructions may be encoded in the computer-readable medium. The instructions may be, for example, software instructions, such as those used to define a software or computer program. The computer-readable medium may be a computer-readable storage medium such as a storage device (e.g., a disk drive, or an optical drive), memory (e.g., a Flash memory or random access memory) or any other type of volatile or non-volatile memory that stores instructions (e.g., in the form of a computer program or other executable) to cause a programmable processor to perform the techniques described herein.

The details of one or more examples of systems, devices, and techniques are set forth in the accompanying drawings and the description below. Other features, objects, and advantages of the disclosure will be apparent from the description and drawings, and from the claims.

DETAILED DESCRIPTION

Figure 1A:
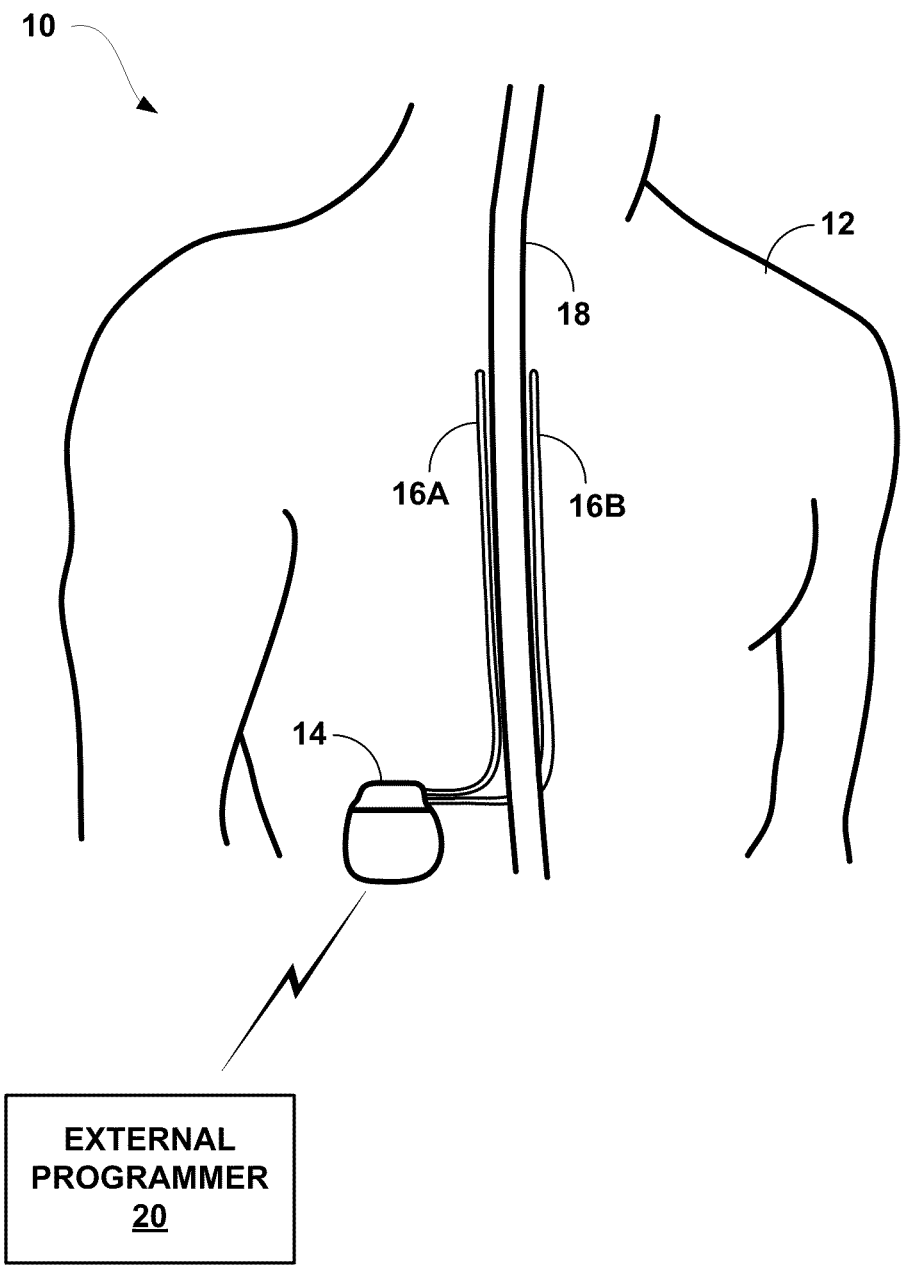
FIG. 1A is a conceptual diagram illustrating an example implantable therapy system including a medical device and two implantable stimulation leads.

In some medical devices that deliver electrical stimulation therapy, therapeutic efficacy may change as the patient changes posture states. In general, a posture state refers to a patient posture or a combination of posture and activity. For example, some posture states, such as upright, may be sub-categorized as upright and active or upright and inactive. Other posture states, such as lying down posture states, may or may not have an activity component. Efficacy may refer, in general, to a combination of complete or partial alleviation of symptoms alone, or alleviation of symptoms in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A medical device may adjust therapy by modifying values for one or more specific therapy parameters, e.g., by specifying adjustments to a specific therapy parameter or by selecting different therapy programs or groups of programs that define different sets of therapy parameter values. A therapy program may define respective values for a set of therapy parameters.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device may employ a posture state detector that determines the patient posture state. The medical device may adjust therapy parameters in response to a determined posture state. Therapy adjustments in response to different posture states may be fully automatic, semi-automatic in the sense that a user may provide approval of proposed changes, or user-directed in the sense that the patient may manually adjust therapy based on the posture state indication.

Stimulation therapy delivered to a patient may be modified for any of a variety of reasons. In some cases, symptoms, such as pain intensity, may change based on the posture state of the patient. For example, a patient may experience a greater degree of pain while walking compared to standing, while standing compared to sitting, or while sitting compared to lying down. In such cases, it may be desirable to adjust one or more therapy parameter values to in order to maintain therapeutic efficacy across multiple posture states. If pain is more intense in a given posture state, for example, stimulation amplitude may be increased to provide more effective pain relief. Posture state changes, in addition to presenting changes in symptoms, may cause implanted therapy elements such as leads and electrodes to migrate relative to one another or relative to a target tissue site.

For example, compression, expansion, or other changes to tissue may render therapy more or less intense due to lead or catheter migration. As an illustration, for spinal cord stimulation (SCS), when a patient transitions from an upright posture state to a lying posture state in which the patient is lying on his back, leads may be compressed inward toward the spinal cord, possibly resulting in an acute increase in stimulation intensity.

To maintain therapeutic efficacy, the stimulation therapy delivered to a patient may be posture responsive in the sense that one or more therapy parameter values may be modified when a patient transitions between different posture states. For example, an implantable electrical stimulation system may be configured to detect a posture state of a patient and automatically modify stimulation therapy based on the detected posture state. Again, the therapy parameter adjustments resulting from the posture responsive therapy may be fully automatic, semi-automatic, or user-directed.

As a result of the posture responsive therapy delivery, the values of one or more stimulation parameters of a stimulation signal being delivered as part of a therapy may be dynamic and change over time, e.g., according to a patient's posture state and/or activity level sensed by an implantable stimulation system. For example, a patient may experience more pain while walking compared to standing. In such cases, an implantable medical device (IMD) may be configured to automatically modify the stimulation therapy to a relatively higher stimulation intensity upon detecting that the patient has transitioned from standing to walking, e.g., by delivering therapy having a higher stimulation amplitude value when the patient is walking compared to the stimulation amplitude value when the patient is standing, to address the increased pain experienced by the patient.

As a further example, an IMD may be configured to automatically modify the stimulation therapy to a lower stimulation intensity when the stimulation system detects that the patient has ceased walking and returned to a standing posture state. In this manner, stimulation therapy delivered to a patient via an IMD may be automatically modified to deliver stimulation appropriate to the posture state exhibited by a patient.

Posture responsive therapy modifications may be made according to a modification profile. The profile of the modification may refer to any of a variety of characteristics of the modification, such as timing, slope, or the like. For some posture state transitions, for example, the modification profile may be characterized by a gradual upward or downward slope in the therapy parameter value over an extended period of time. For other posture state transitions, the modification profile may be characterized by an abrupt increase or decrease in a therapy parameter value. In this case, the therapy parameter value may be more immediately (e.g., instantaneously) modified, rather than gradually ramped upward or downward.

An immediate change in the therapy parameter value may be characterized by, for example, a jump from therapy delivery according to a first therapy parameter value to therapy delivery according to a second therapy parameter value. In contrast, a gradual change in the therapy parameter value may be accomplished by, for example, shifting from the therapy parameter value to therapy delivery according to a second therapy parameter value over time. The shift from the first therapy parameter value to the second therapy parameter value may involve, for example, therapy delivery according to intermediate therapy parameter values between the first and second therapy parameter values. In other examples, the therapy parameter value may be ramped from an existing therapy parameter value to a desired parameter value rather than ramping the existing parameter value down to approximately zero and then ramping up from zero to the new stimulation parameter, e.g., as in an immediate change in the therapy. For example, in the case of an adjustment in which the desired parameter value is higher than the existing parameter value of the stimulation being delivered, an IMD may increase the parameter value by ramping up to the desired value according to a constant rate of change during a transition period.

When therapy delivery to the patient is gradually changed, the modification profile may define the amount of time required for the parameter to be increased from the existing parameter value to the desired parameter value at the defined rate of change. This parameter of the modification profile may be referred to as a transition time. By gradually ramping a stimulation parameter value to a desired level over time rather than making an adjustment to a desired value substantially immediately, an IMD may effectively adjust the stimulation parameter based on patient posture state without the patient experiencing undesirable side effects that may result from making abrupt changes to a stimulation parameter, such as stimulation amplitude, too quickly.

In some examples, an IMD may make an adjustment to a stimulation parameter at different rates of change, i.e., different ramping rates, depending on one or more properties relating to the adjustment. As one example, the specific rate of change with which an IMD adjusts a stimulation parameter may correspond to a particular posture state transition that resulted in the parameter adjustment. As another example, the specific rate of change with which an IMD adjusts a stimulation parameter may correspond to the nature or type of parameter adjustment, e.g., an increase or decrease. In this manner, not only may the stimulation therapy delivered to a patient be modified based on particular posture state transitions but also particular types of modifications in therapy parameter values.

In addition, in some circumstances, an abrupt modification profile may be desirable, such as when a patient transitions from an upright posture state to a lying down (back) posture state. In this case, it may be desirable to reduce stimulation amplitude to reduce stimulation intensity in the event tissue compression places the electrodes closer to the target tissue. Moreover, it may be desirable to reduce stimulation amplitude abruptly rather than by a gradual ramp in order to reduce the likelihood that the patient will experience discomfort due to transfer of a greater effective amount of stimulation energy upon tissue compression.

An IMD may implement a variety of techniques for posture responsive therapy modification that make use of different modification profiles for different posture state transitions. By applying different modification profiles for different posture state transitions, such techniques may support consistent therapeutic efficacy as a patient transitions between different posture states.

An IMD that provides posture responsive therapy may be programmed with the assistance of a clinician during a programming session. A programming session may occur prior to a therapy session, during which the patient is not present at a clinic and the IMD delivers therapy to a patient (e.g., in an ambulatory manner based on therapy parameter values programmed during a therapy session), or in between therapy sessions. Devices, systems, and techniques for programming an IMD that is configured to provide posture responsive therapy delivery are described in this disclosure.

During a first phase of a programming session, a clinician selects one or more therapy parameter values (referred to herein as a first set of therapy parameters values, which may include one or more therapy parameters) that provide efficacious therapy to a patient in a particular patient posture and associate the one or more therapy parameter values with the patient posture in a memory of a device (e.g., the IMD or a programmer). In the case of stimulation therapy, the first set of therapy parameters may include, for example, a current or voltage amplitude, signal duration (e.g., pulse width in the case of stimulation pulses), frequency (e.g., pulse rate in the case of stimulation pulses), electrode combination (e.g., selected electrodes and respective polarities for delivering stimulation), and/or duty cycle. The IMD is programmed to deliver therapy to the patient according to the selected first set of therapy parameter values when the posture responsive therapy features of the IMD are activated, e.g., when IMD is in a posture responsive therapy mode.

The IMD is in a first mode (referred to herein as a programming mode) while the values for the first set of therapy parameters are selected. When the programming mode of the IMD is activated, the posture responsive therapy features of the IMD are deactivated in order to enable the clinician to maintain control over the therapy parameters that are actually delivered to the patient. That is, when in the programming mode, the IMD is instructed (e.g., via a programmer that communicates with the IMD) to deliver therapy according to user-selected therapy parameter values, rather than according to therapy parameter values that are selected based on a detected patient posture and/or activity level. In contrast, when the posture responsive therapy mode (also referred to as a second mode) of the IMD is activated, the IMD may automatically select therapy parameter values based on a sensed patient posture and/or activity level. Accordingly, the clinician may not have control over the exact therapy parameters that are delivered to the patient when the posture responsive therapy features of the IMD are activated.

In some examples, the programming mode and the posture responsive therapy mode of the IMD are mutually exclusive such that the IMD can be in the programming mode or the posture responsive therapy mode, but not both at one time. The programming mode of the IMD may be activated using any suitable technique, e.g., by deactivating the posture responsive therapy mode or by otherwise controlling the IMD to deliver therapy based on stimulation parameters selected by the clinician or programmer.

It may be difficult for the clinician to accurately determine the therapeutic efficacy (e.g., balance between minimization of side effects and decrease in patient symptoms) of a specific set of therapy parameter values if the clinician does not have control over the therapy parameter values with which the IMD generates and delivers therapy to the patient. For example, if the clinician selects a first therapy parameter value for trialing on the patient and the posture responsive therapy mode of the IMD is activated, the IMD may generate and deliver therapy to the patient with a different therapy parameter value that is associated with a detected patient posture state, rather than the first therapy parameter value. Deactivating the posture responsive therapy mode of the IMD during the first phase of the programming session provides the clinician direct control over the therapy parameter values with which the IMD generates therapy. In some cases, the clinician may instruct the IMD to generate and deliver therapy to the patient with clinician-selected therapy parameter values with the aid of a medical device programmer, which may be a computing device configured to wirelessly communicate with the IMD.

During the first phase of the programming session, the IMD delivers trial therapy generated in accordance with the first set of therapy parameter values while the posture responsive therapy features of the IMD are deactivated. Deactivating the posture responsive therapy mode of the IMD enables a clinician or programmer to maintain control over the actual therapy parameters with which the IMD delivers therapy to the patient. Trial therapy with a first set of therapy parameter values is delivered to the patient while the posture responsive therapy features of the IMD are deactivated. The clinician, or, in some cases, the programmer, modifies one or more values of the first set of therapy parameters based on efficacy of the trial therapy delivered while the posture responsive therapy features of the IMD are deactivated. The first set of therapy parameters may include values that define the stimulation signal or therapeutic agent doses delivered to the patient.

After efficacious values for the first set of therapy parameters are selected and during the same programming session in which the first set of therapy parameter values are selected, the clinician activates the posture responsive therapy features of the IMD. During a second phase of the programming session, the posture responsive therapy mode of the IMD is temporarily activated, and the IMD activates the actual posture responsive therapy mode that is programmed to be delivered to the patient during chronic therapy delivery by the IMD. Posture responsive therapy is delivered to the patient during the second phase with the first set of therapy parameter values and a second set of therapy parameter values. The first and second sets of stimulation parameter values are different. The second set of therapy parameter values define the manner in which the IMD detects a posture transition and modifies therapy delivery to a patient based on a detected posture transition. For example, the second set of therapy parameter values may include the modification profiles with which the IMD switches between therapy parameter settings (e.g., therapy programs) associated with different patient postures or the definition of the patient posture states stored by the IMD.

During the second phase of the programming session, the clinician, with the aid of patient input (e.g., verbal, written, electronic or otherwise) or with the aid of physiological sensors (implanted or external), can determine the therapeutic efficacy of the posture responsive therapy implemented with the selected first set of therapy parameter values and the second set of therapy parameter values. Based on the patient input, observed physiological effects of posture responsive therapy or other indications of therapeutic efficacy, the clinician may modify the first and/or second set of therapy parameter values of the IMD. In some examples, the IMD may not be programmed (e.g., the programming features of the IMD are not accessible) during the posture responsive therapy mode. In such examples, in order to modify the first and/or second set of therapy parameter values, the clinician may place the IMD back into the programming mode.

Efficacy of therapy may not only be based on the actual parameters of the stimulation signals or therapeutic agent doses delivered to the patient, as characterized by the first set of therapy parameter values, but on the responsiveness with which the IMD delivers the therapy to accommodate different patient postures and/or activity levels. The responsiveness of the IMD may depend on various therapy parameters (referred to herein as a second set of therapy parameters). Examples of parameter values in the second set include parameters in a modification profile, such as a dwell time. In some cases, the dwell time defines a period of time following a detection of a posture state transition by the IMD and prior to an initiation of a change in therapy to accommodate the posture state transition. In other cases, the dwell time defines a period of time between the actual posture state transition by the patient and an initiation of a change in therapy by the IMD to accommodate the posture state transition.

In some examples, the parameters in the modification profile can include a transition period, which indicates a duration of time over which the IMD gradually switches between therapy programs in response to detecting a posture state transition and a ramp rate, which is the rate at which the a therapy parameter value (e.g., amplitude) is switched in response to a posture state transition. Either the ramp rate or transition period may remain variable and the other may remain fixed. For example, in some examples, the ramp rate is a predetermined and fixed value, and the transition period depends upon the ramp rate and the net increase or decrease to a therapy parameter value made in response to the posture state transition. As another example, the transition period may be predetermined and fixed, and the ramp rate may depend upon the net increase or decrease to a therapy parameter value and the fixed transition period over which the increase or decrease takes place. In some examples, the transition period may be fixed and the ramp rate may not be a constant value. Dwell times and transition periods are described with reference to FIG. 12.

During the second phase of the programming session in which the posture responsive therapy mode of the IMD is activated, the IMD automatically dynamically adjusts therapy in response to sensed patient postures and/or activity levels. In this way, the clinician may test the posture responsive therapy features of the IMD, evaluate the response of the patient to the posture responsive therapy, and, if necessary, modify the second set of therapy parameter values based on the results of testing the posture responsive therapy features. The IMD does not deliver posture responsive therapy unless the IMD is in a posture responsive therapy mode. Thus, temporarily activating the posture responsive therapy mode during the same programming session (i.e., without an intervening therapy session) in which other therapy parameter values are selected may be useful for evaluating the efficacy of the posture responsive therapy delivered by the IMD. In the absence of activating the posture responsive therapy mode during the programming session, the clinician may be unable to evaluate the second set of therapy parameter values, and, accordingly, unable to effectively select efficacious values for the second set of therapy parameters.

Both the first and second set of therapy parameter values may be modified during the first phase of the programming session during which the posture responsive therapy features of the IMD are deactivated. However, only the first set of therapy parameter values are modified based on the efficacy of therapy delivery determined during the first phase. Because the posture responsive therapy features are not tested during the first phase of the programming session, the effects of the posture responsive therapy feature are not determined during the first phase. Thus, the second set of therapy parameter values, which affect the posture responsive therapy (e.g., the responsiveness with which the IMD switches between therapy parameter settings upon detecting a change in patient posture), are not tested (e.g., trialed) during the first phase of the programming session, and the efficacy of the therapy delivery in accordance with the second set of therapy parameter values are not determined during the first phase while the IMD is in a programming mode.

Similarly, both the first and second set of therapy parameter values may be modified during the second phase of the programming session after the posture responsive therapy features of the IMD are tested and the efficacy of the posture responsive therapy are determined. In some cases, only the second set of therapy parameter values are modified based on the efficacy of therapy delivery determined during the second phase. In other cases, however, the first set of therapy parameter values are also modified based on the efficacy of therapy delivery determined during the second phase.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and IMDs, application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat movement disorders (e.g., tremor), Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1A), and the parameters for a therapy program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes (not shown) that are placed adjacent to the target tissue of spinal cord 18 of patient 12. One or more electrodes may be disposed proximate to a distal end of a lead 16 and/or at other positions at intermediate points along the lead 16. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) electrically connected to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In other examples, IMD 14 is a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or continuous waveforms. In some examples, the target tissue includes nerves, smooth muscle or skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through spinal cord 18 and to the brain of patient 12. Patient 12 may perceive the interruption of pain signals as a reduction in pain and, therefore, efficacious therapy results.

The deployment of electrodes via leads 16 connected to IMD 14 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers electrical stimulation to patient 12 according to one or more programs. A program defines one or more therapy parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target stimulation site. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to mitigate additional pain or unusual sensations from the increased compression near electrodes of leads 16.

IMD 14 includes a posture state module that determines a patient posture state and, in some cases, a patient activity level. The patient posture and activity level may generally be referred to as a posture state. Example posture states may include "Upright," "Upright and Active," "Lying Down," and so forth. IMD 14 includes a posture responsive therapy mode that, when activated, results in adjustment of one or more stimulation parameter values based on a detected posture state. The posture responsive therapy may help mitigate changes in the efficacy of therapy attributable to patient posture changes. For example, the posture state module may include one or more accelerometers (e.g., one or more single axis, two-axis or three-axis accelerometers) that detect when patient 12 occupies a posture state for which it is appropriate to decrease the stimulation amplitude, e.g., when patient 12 lies down. IMD 14 may automatically reduce stimulation amplitude upon detecting patient 12 is lying down, thereby eliminating the need for patient 12 to manually adjust the therapy, which may be cumbersome. In addition, automatic adjustment of stimulation parameters based on a detected patient posture may also provide more responsive therapy because IMD 14 may detect a change in patient posture and modify therapy parameters faster than patient 12 manually modifying the therapy parameters.

As described in greater detail below, in some examples, IMD 14 is configured to automatically decrease stimulation amplitude when it detects that patient 12 has changed posture states to a lying down state. The amplitude adjustment may be configured to be decreased at a rate suitable to prevent undesirable effects, e.g., such as the effects due to the compression of leads 16 towards spinal cord 18 when patient lies down. In some examples, IMD 14 is configured to decrease the stimulation amplitude to a suitable amplitude value substantially immediately upon detection by IMD 14 that patient 12 is lying down. In other examples, the stimulation amplitude may not be decreased substantially immediately by IMD 14 upon detection of patient 12 lying down, but instead IMD 14 may decrease the stimulation amplitude to a suitable amplitude level at a rate of change that is suitable to prevent patient 12 from experiencing undesirable stimulation effects, e.g., due to increased transfer of stimulation energy to tissue of patient 12. In some examples, IMD 14 may substantially instantaneously decrease the stimulation amplitude to a suitable amplitude value when IMD detects that patient 12 is lying down.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include an activity sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When patient 12 lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on a time interleaved or rotating basis. Programmer 20 transmits the commands, programs or other information to IMD 14 with the aid of wireless communication signals.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

Figure 14A:
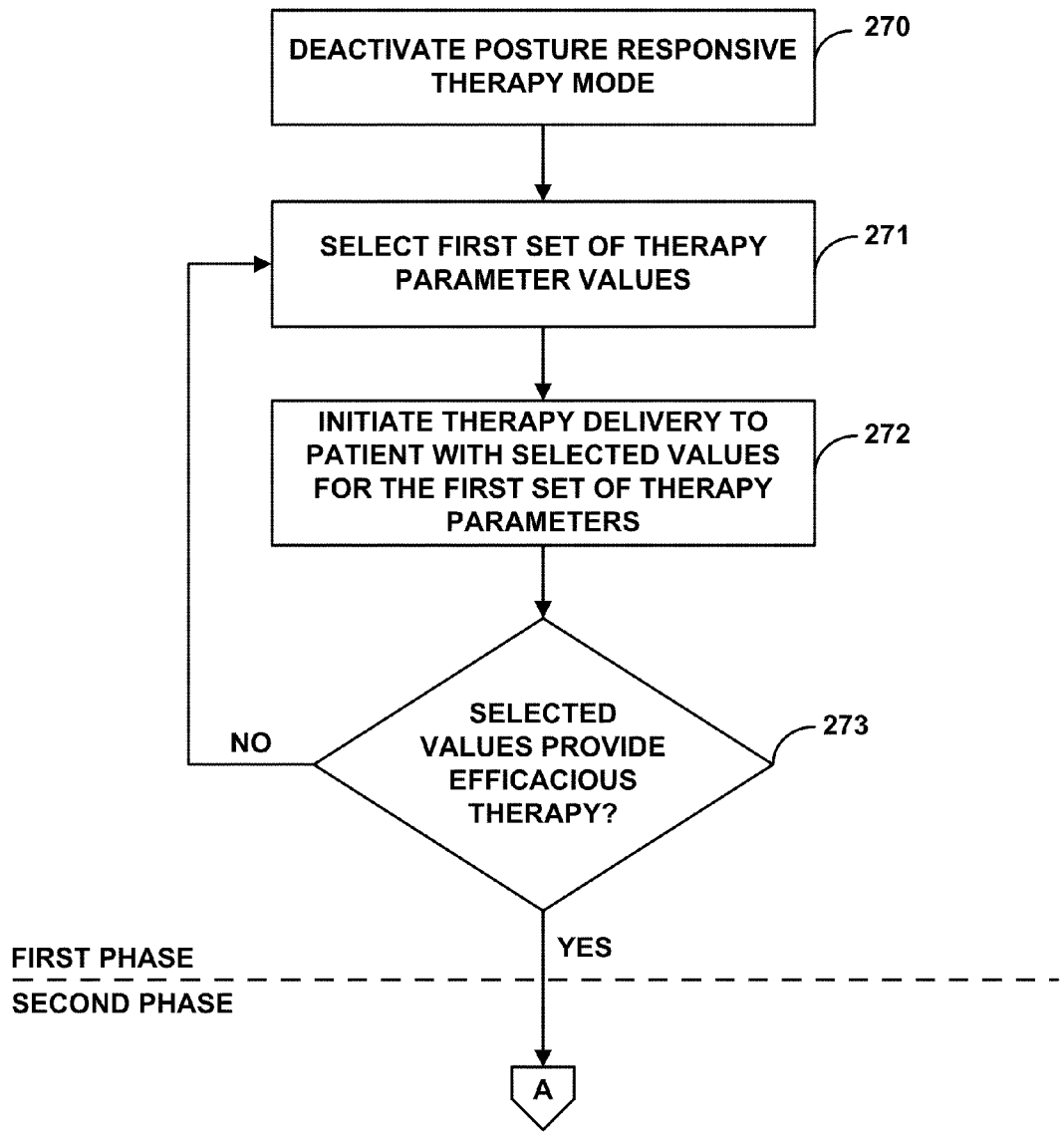
FIGS. 14A and 14B are flow diagrams illustrating an example technique for programming an implantable medical device that includes a posture responsive therapy mode.
Figure 14B:
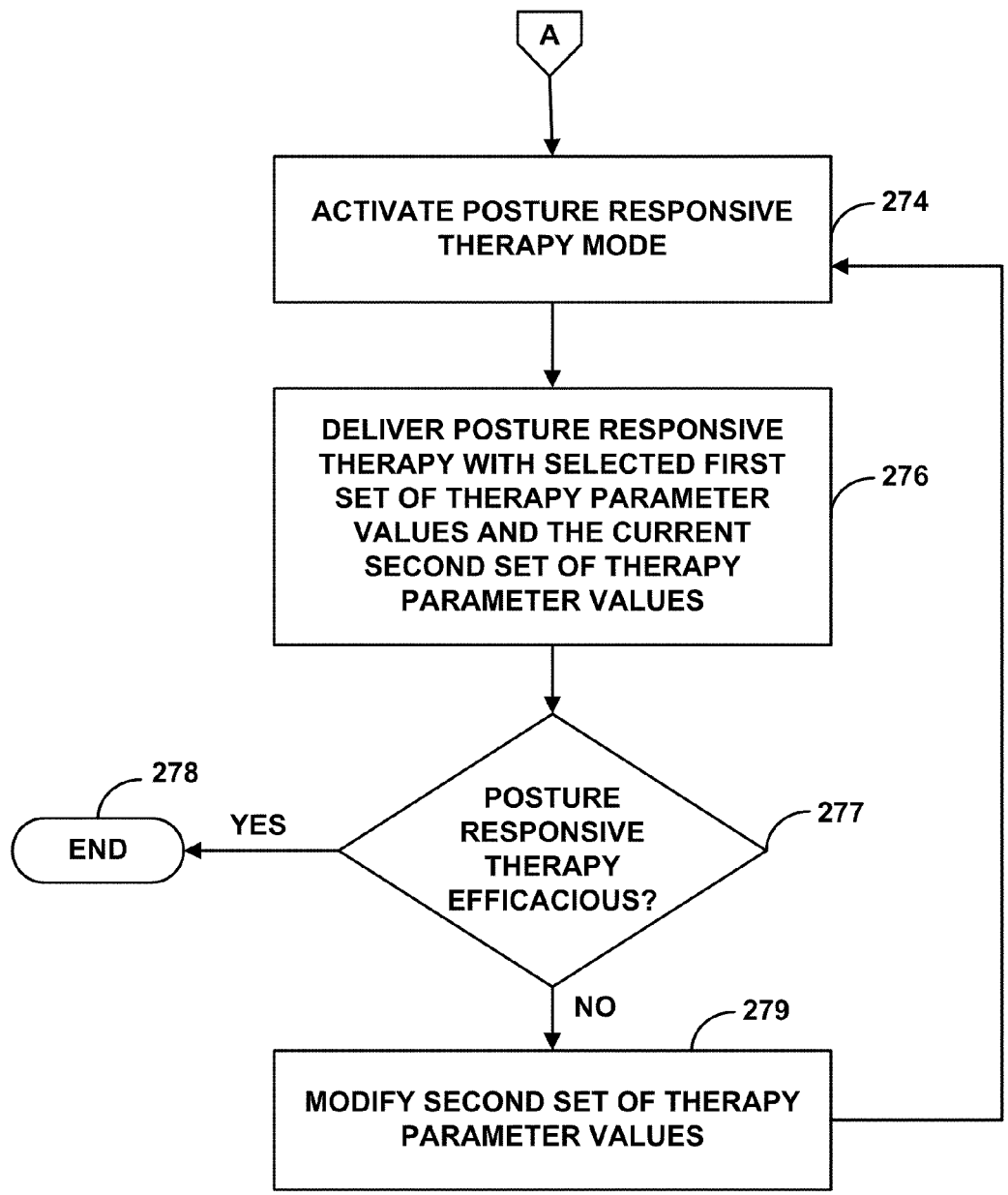

As described in further detail with respect to FIGS. 14A and 14B, in some examples, IMD 14 is programmed with programmer 20 during a programming session having at least two phases. The programming session may take place prior to or between therapy sessions, which can be time in which IMD 14 provides therapy to patient 12 on a chronic (e.g., non-temporary) basis. In a first phase of the programming session, IMD 14 is in a programming mode in which the posture responsive therapy features of IMD 14 are deactivated (e.g., temporarily suspended). While the posture state module within IMD 14 may continue to sense the posture of patient 12 while the posture responsive therapy features of IMD 14 are deactivated, IMD 14 does not automatically select therapy parameter values based on the detected patient posture. Instead, IMD 14 generates and delivers therapy to patient 12 based on therapy parameter values selected by a user (e.g., a clinician) via programmer 20. For example, a clinician may select a therapy program, which may be stored within programmer 20 or IMD 14, and programmer 20 may transmit a signal to IMD 14 that instructs IMD 14 to generate and deliver therapy to patient 12 according to the selected therapy program. In this way, the clinician may have direct control over the therapy parameter values with which IMD 14 actually generates and delivers therapy.

When the posture responsive therapy features of IMD 14 are activated, e.g., IMD 14 is in a posture responsive therapy mode, the clinician may not have direct control over the therapy parameter values with which IMD 14 actually generates and delivers therapy because IMD 14 is programmed to dynamically change one or more therapy parameter values based on a determined patient posture state when the posture responsive therapy features of IMD 14 are activated. When the clinician lacks control over the therapy parameter values, it may be difficult for the clinician to assess the therapeutic efficacy of different therapy parameters. For example, if the clinician wants to determine whether a first therapy program provides efficacious therapy to patient 12, the clinician may instruct IMD 14 to deliver therapy to patient 12 according to the first therapy program while patient 12 is in a first patient posture. However, if the posture responsive therapy features of IMD 14 are activated and the first therapy program is not associated with the first patient posture, IMD 14 may automatically deliver therapy according to a second therapy program that is associated with the first patient posture, e.g., within a memory of IMD 14. Thus, IMD 14 may circumvent the clinician's attempt to test the first therapy program because IMD 14 dynamically changes the therapy programs in response to a detected patient posture.

In accordance with the programming techniques described herein, the posture responsive therapy mode of IMD 14 is deactivated during a first phase of a programming session. The deactivation of the posture responsive therapy features of IMD 14 enables the clinician to deliver trial stimulation to patient 12 according to a clinician-selected therapy program without IMD 14 circumventing the selected therapy program. In the first phase of the programming session, the clinician selects values for a first set of stimulation parameters that provide efficacious therapy to patient 12. The first set of stimulation parameters may include, for example, therapy parameters that define the stimulation signals that are delivered to the patient 12. These stimulation parameters include, for example, the stimulation signal amplitude, frequency, and duration, and the electrode combination with which IMD 14 delivers the stimulation signal. The clinician, with the aid of programmer 20 modifies the first set of stimulation parameter values based on the efficacy of therapy delivery determined based on the trial therapy delivered during the first phase of the programming session. In some cases, programmer 20 automatically modifies the first set of stimulation parameter values based on the efficacy of therapy delivery determined during the first phase.

During the first phase of programming IMD 14, the clinician may also define the patient posture states and associate the selected stimulation parameter values with a patient posture state. The patient posture state definitions associate a posture sensor output (e.g., a vector) with a particular patient posture state. The patient posture state definitions may be determined by, for example, defining posture regions, such as posture cones, for one or more of the posture states. As described in further detail with reference to FIGS. 8A-8C, in some examples, a posture cone is defined by a reference coordinate vector for a given posture state in combination with a distance or angle defining a range of coordinate vectors within a cone surrounding the posture reference coordinate vector. The reference coordinate vector may be, for example, a vector determined based on the output of the posture sensor when patient 12 is in a known posture state.

In other examples, a posture cone is defined by a reference coordinate vector and a range of cosine values computed using the reference coordinate vector as an adjacent vector and any of the outermost vectors of the cone as a hypotenuse vector. The clinician may instruct patient 12 to undertake each of a plurality of postures and determine the patient posture state definitions for each of the plurality of postures. The posture state definitions may be stored in a memory of IMD 14, programmer 20 or another device.

In some examples, the clinician selects the stimulation parameter values and subsequently assigns the stimulation parameter values to a patient posture state for which the stimulation parameter values provide efficacious therapy. In other examples, the clinician selects a patient posture state and subsequently selects the stimulation parameter values that provide efficacious therapy for the selected patient posture state. In either example, a set of therapy parameter values may be stored as a therapy program in a memory of IMD 14, a memory of programmer 20, and/or a memory of another device.

A programming session is useful for not only selecting a plurality of therapy programs that provide efficacious therapy to patient 12 in different patient postures, but also selecting the parameters with which IMD 14 transitions between therapy programs for the different patient postures. Although "therapy programs" are generally referred to herein, the therapy parameters may be generally grouped together as therapy parameter settings and need not be defined as a specific therapy program. The parameters with which IMD 14 transitions between therapy programs for the different patient postures include, for example, a dwell time, transition period, and ramp rate, which may be considered part of a modification profile of IMD 14.

The modification profile indicates the manner in which IMD 14 detects a posture transition and modifies therapy in response to the detected posture transition. A dwell time indicates a duration of time between the detection of a posture state transition or the actual posture state transition and the activation of a change in a parameter such as amplitude to adjust therapy to accommodate the posture state transition. During a dwell time period, IMD 14 detects the posture transition by patient 12 and imposes a delay period before modifying therapy delivery. A transition period indicates a duration of time over which IMD 14 transitions between a first therapy program (or therapy parameter settings) associated with a first patient posture state and a second therapy program associated with a second, detected patient posture state. A ramp rate indicates the rate of change with which IMD 14 switches between therapy parameter values based on a particular posture state transition.

In some examples, however, a modification profile does not include a ramp rate and/or a transition time. For example, IMD 14 may implement a ramp rate or transition time that is independent of the posture state transition. In such examples, the ramp rate or transition time may be selected based on whether the stimulation parameter value (e.g., amplitude) is increasing or decreasing in response to a detected posture state transition. For example, a ramp rate and/or transition time may be shorter if the stimulation parameter value is decreased in response to a detected posture state transition compared to if the stimulation parameter value is increased.

Efficacy of therapy may not only be based on the actual parameters of the stimulation signals delivered to patient 12, but the manner in which IMD 14 switches between therapy programs when a change in patient posture is detected. For example, if there is a substantially long time delay between when patient 12 changes posture and when IMD 14 switches therapy programs in response to the posture transition, patient 12 may perceive the therapy as being ineffective. As another example, if IMD 14 switches therapy programs relatively quickly, the abrupt switch between therapy programs may cause discomfort to patient 12.

Modification profiles define the manner in which IMD 14 switches between therapy programs, e.g., in response to a detected posture state transition. A clinician may program the modification profiles, such as by selecting the durations of time for the dwell time and selecting either the transition time or ramp rate with which IMD 14 shifts between therapy parameter values. Either the ramp rate or transition period may remain variable and the other may remain fixed. For example, in some examples, the ramp rate is a predetermined and fixed value, and the transition period depends upon the ramp rate and the net increase or decrease to a therapy parameter value. As another example, the transition period may be predetermined and fixed, and the ramp rate may depend upon the net increase or decrease to a therapy parameter value and the fixed transition period over which the increase or decrease takes place. Therapy delivery according to the modification profile, however, is not implemented by IMD 14 when IMD 14 is in a programming mode because the posture responsive therapy features of IMD 14 are deactivated. That is, when IMD 14 is not providing posture responsive therapy, IMD 14 does not automatically switch between therapy programs according to the modification profile to accommodate different patient postures. Because the modification profiles influence the patient's perceived efficacy of therapy, it is desirable for the clinician to trial (i.e., test) the programmed modification profiles during the programming session.

Similarly, efficacy of therapy may also be based on the posture state that IMD 14 detects. The posture state detection by IMD 14 depends on various parameters, including the definition of the posture states. In some cases, IMD 14 determines a posture state of patient 12 based on a signal from a posture sensor (e.g., an accelerometer). IMD 14 may include a memory that associates the signal with a posture state. As described with respect to FIGS. 8A-8C, in some cases, the posture states are defined by a plurality of posture cones, which associate outputs from a posture state sensor with different patient posture states. The posture cone defines a three-dimensional region associated with a particular posture state. For example, a vector from the three-axis accelerometer of a posture state module of IMD 14 may reside within a predefined posture cone, thereby indicating patient 12 is in the posture associated with the predefined cone. For example, if a sensed posture state vector is within an applicable angle or distance of a reference coordinate vector associated with the particular posture state, or if the sensed posture state vector and the reference coordinate vector produce a cosine value in a specified cosine range associated with the particular posture state, then patient 12 is determined to be in the particular posture state. In addition, IMD 14 may determine a patient posture state based on hysteresis zones between posture cones. As described below with reference to FIGS. 8A-8C, posture state definitions may define other posture state regions in addition to or instead of posture cones.

If posture state definitions (e.g., the size of a posture state region) or hysteresis zones, or the orientations of the posture cones are inaccurate, patient 12 may perceive the posture responsive therapy delivery by IMD 14 to be ineffective. For example, if patient 12 assumes a first posture, but IMD 14 determines patient 12 is in a second posture based on the stored posture state definitions, IMD 14 may deliver therapy associated with the second posture, rather than the first, true patient posture. The therapy associated with the second posture may not provide efficacious therapy to patient 12 when patient is in the first posture. In this way, the posture state definitions stored by IMD 14 may also affect the effectiveness of the posture responsive therapy mode of IMD 14.

In some examples, a size of a posture cone may be defined in terms of a tolerance associated with the posture state. As described in further detail below with reference to FIGS. 8A-8C, one way to specify a tolerance is by providing an angle relative to a coordinate reference vector that is associated with the posture state. Another way to specify a tolerance is by providing a cosine value or range of cosine values that are determined using a reference coordinate vector as an adjacent vector and any of the outermost vectors of the posture cone as a hypotenuse vector.

In accordance with the programming techniques described herein, after determining values for the first set of stimulation parameters that provide efficacious therapy to patient 12 and associating the stimulation parameters with respective patient posture states, a second phase of the programming session is initiated in which the posture responsive therapy mode of IMD 14 is activated. During the second phase, an efficacy of therapy delivery with a second set of therapy parameter values is determined and the second set of therapy parameter values are modified based on determined efficacy. The first and second phases of the same programming session may be performed in a clinic and during the same clinic visit, e.g., without an intervening therapy session in which patient 12 is sent home with IMD 14.

When the posture responsive therapy is activated during part of the second phase of the programming session, IMD 14 dynamically controls the therapy parameters based on a posture state detected by the posture state module of IMD 14 during the second phase. IMD 14 selects a therapy program based on a detected patient posture state, whereby the therapy programs from which IMD 14 selects from include the therapy programs selected by the clinician during the first phase of the programming session. Thus, in order to test the posture responsive therapy during the programming session, at least two different posture-specific therapy parameter values (e.g., amplitudes) are defined prior to activation of the posture-responsive therapy. That is, in order to test the responsiveness with which IMD 14 changes therapy parameter values in response to detecting a posture state transition, at least two different therapy parameter values, each associated with a respective posture state, are defined prior to activation of the posture-responsive therapy during the programming session.

In addition, the posture state definitions with which IMD 14 detects the patient posture states may also be defined during the first phase of the programming session. During the second phase of the programming session, patient 12 may undertake a plurality of posture changes in order to evaluate the efficacy of the modification profiles of IMD 14 and evaluate the accuracy of the posture state definitions while the stimulation therapy is activated. In some cases, posture changes undertaken by patient 12 during the second phase of the programming session may be specific, clinician directed posture changes, or may be random and based on the course of patient activity during the second phase. The second phase of the programming session may take place over any suitable period of time, such as a few minutes to a few hours or more. In some examples, other programming features (e.g., features that permit the stimulation parameter values of IMD 14 to be selected) of IMD 14 are deactivated during the second phase of the programming session.

Patient 12 may provide input relating to the efficacy of the posture responsive therapy delivery with the second set of therapy parameter values, including the modification profiles. The input may be verbal or written input, or may be provided via programmer 20. For example, programmer 20 may present one or more questions to patient 12 that assess the efficacy of the posture responsive therapy provided by IMD 14. The questions may prompt patient 12 for a numerical or other scaled efficacy rating for each trialed posture transition. In general, the patient input includes a subjective assessment of the modification profiles.

In addition, in some examples, the clinician may utilize one or more sensors that sense one or more physiological parameters to determine the efficacy of the modification profiles. Examples of physiological parameters that may indicate efficacy of therapy include, for example, heart rate, respiration rate, brain signals (e.g., determined by an electroencephalogram (EEG) or electrocorticogram (ECoG)), an electrocardiogram (ECG), body temperature, blood pressure, electrodermal activity (e.g., galvanic skin response or skin conductance response), muscle activity (e.g., electromyogram (EMG)), blood flow rate, sweat gland activity, pilomotor reflex (e.g., goose bumps), or the like.

For each of the physiological parameters that are monitored during the second phase of the programming session, the clinician may determine a threshold value or a target range of values for the physiological parameters that indicate efficacious therapy. For example, in examples in which IMD 14 provides therapy to manage pain, a relatively high heart rate, a relatively large pilomotor reflex or electrodermal activity of patient 12 may indicate patient 12 is experiencing pain. Thus, if a sensed heart rate, pilomotor reflex or electrodermal activity falls outside of a stored range of values during a particular posture transition that is trialed during the second phase, the clinician may determine that IMD 14 is not effectively adjusting therapy to accommodate changes in the patient's physiological condition resulting from the posture transition. Other means of evaluating efficacy of therapy based on one or more sensed physiological parameters of patient are contemplated.

After trialing the posture responsive therapy mode of IMD 14, a clinician may modify the modification profiles for the posture transitions and/or the posture state definitions, which are a part of a second set of therapy parameters that are modified during the second phase of the programming session. The clinician may modify the values of one or more therapy parameters of the second set based on the patient input and/or information provided by the sensors. In some examples, the modification profiles for the posture transitions and/or the posture state definitions can only be modified when IMD 14 is in a programming mode and is not in the posture responsive therapy mode. Thus, in some examples, during the second phase of the programming session, a clinician may activate the programming mode of IMD 14 prior to adjusting the modification profiles for the posture transitions and/or the posture state definitions of IMD 14 based on the efficacy of posture responsive therapy determined when the posture responsive therapy features were activated.

In some examples, the posture responsive therapy mode of IMD 14 may only be activated during the second phase of the programming session for a predetermined maximum duration of time. Thus, after a predetermined duration of time, IMD 14 may automatically revert from the posture responsive therapy mode back to a programming mode in which the posture responsive therapy features of IMD 14 are deactivated and one or more therapy parameter values with which IMD 14 generates therapy may be adjusted. The clinician may select the predetermined duration of time or the predetermined duration of time may be selected by, e.g., a manufacturer of IMD 14 or programmer 20. In some examples, the predetermined duration of time is about one minute to one hour or more, such as about 30 minutes. In other examples, the second phase of the programming session does not terminate until a clinician intervenes and reverts IMD 14 from the posture responsive therapy mode back to the programming mode.

While both the first and second set of therapy parameter values may be modified during both the first and second phases of the programming session, only the first set of therapy parameter values are modified based on efficacy of trial therapy delivery determined during the first phase of the programming session. The second set of therapy parameter values are not trialed during the first phase of the programming session because the posture responsive therapy features are deactivated during the first phase and the second set of therapy parameter values define how IMD 14 dynamically adjusts therapy when the posture responsive mode of IMD 14 are activated. Thus, the efficacy of therapy delivery with specific values of the second set of therapy parameters may not be determined until the posture responsive therapy mode of IMD 14 is activated and trialed.

Both the first and second set of therapy parameter values may also be modified based on efficacy of trial therapy delivery determined during the second phase of the programming session. However, because the first set of therapy parameter values were already determined to provide efficacious therapy to patient 12 during the first phase of the programming session, a determination that posture responsive therapy delivery provided by IMD 14 during the second phase was inefficacious may more likely indicate that an adjustment to the second set of therapy parameters (e.g., modification profiles or posture state definitions) is desirable.

IMD 14 may be constructed with a biocompatible housing, such as titanium or stainless steel, or a polymeric material such as silicone or polyurethane, and surgically implanted at a site in patient 18 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other suitable location to secure IMD 14. Leads 16 may be tunneled from IMD 14 through tissue to reach the target tissue adjacent to spinal cord 18 for stimulation delivery.

Figure 1B:
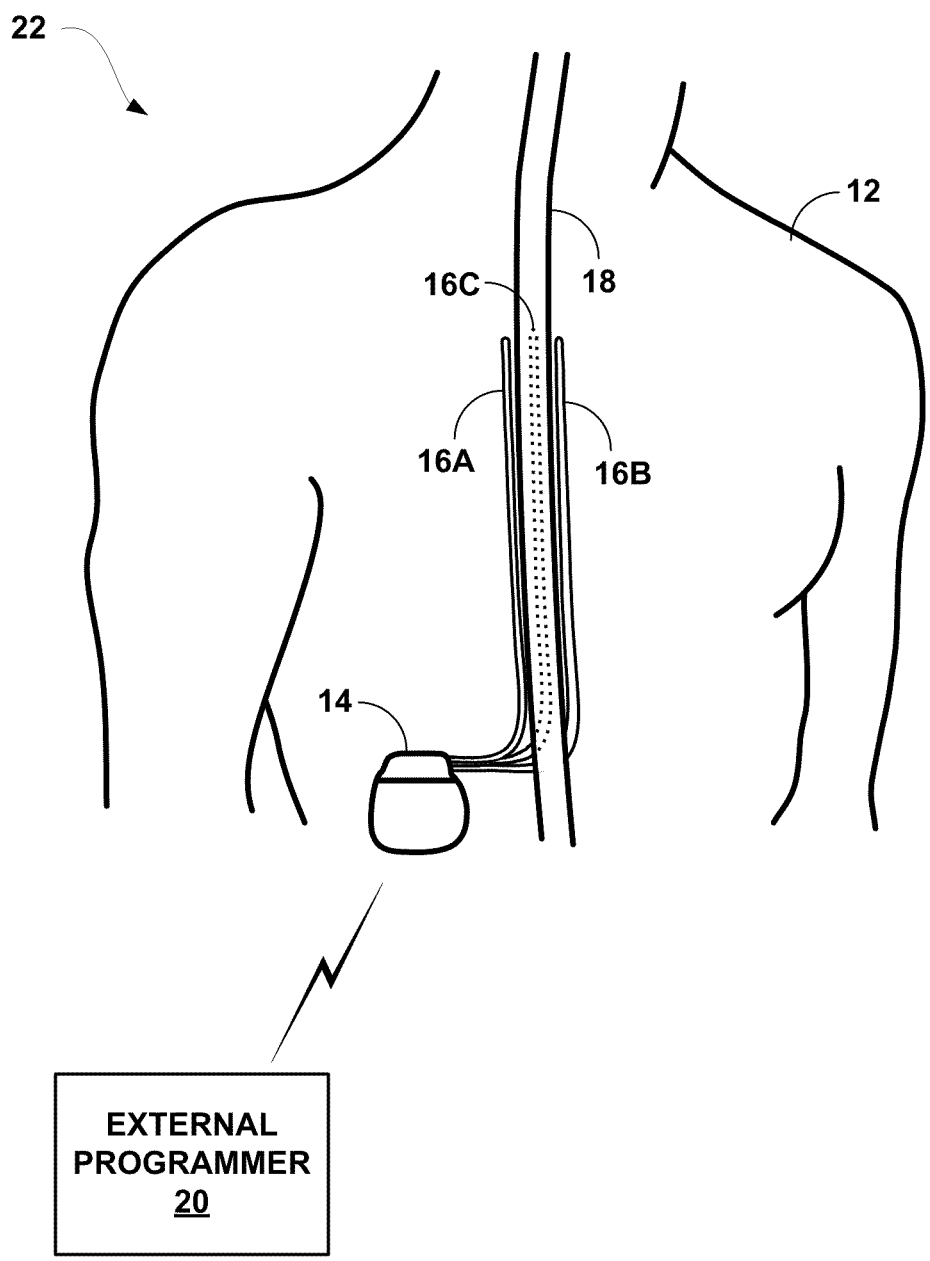
FIG. 1B is a conceptual diagram illustrating another example implantable therapy system including three implantable stimulation leads.

FIG. 1B is a conceptual diagram illustrating stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 in order to programmer 20 appropriately program stimulation therapy or assist in the programming of stimulation therapy.

In some examples, leads 16A and 16B include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
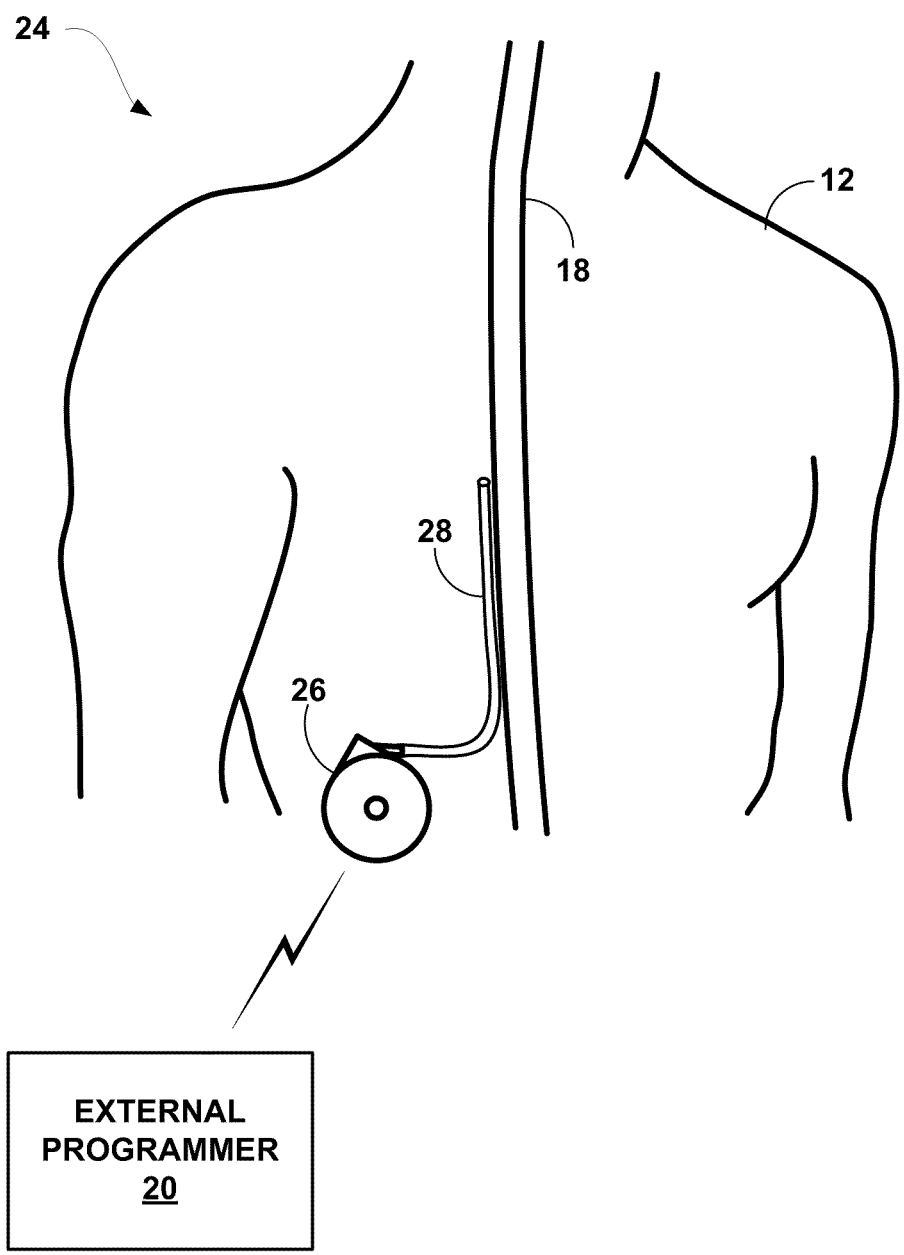
FIG. 1C is a conceptual diagram illustrating an implantable drug delivery system including a drug delivery device and a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of the delivery of therapeutic agents instead of electrical stimulation. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ.

Alternatively, each catheter may deliver therapy to different tissues within patient 12 for the purpose of treating multiple symptoms or conditions. In some examples, IMD 26 may be an external device that includes a percutaneous catheter to deliver a therapeutic agent to patient 12, e.g., in the same manner as catheter 28. Alternatively, the percutaneous catheter may be coupled to catheter 28, e.g., via a fluid coupler. In other examples, IMD 26 may include both electrical stimulation capabilities, e.g., as described with respect to IMD 14 (FIG. 1A), and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery. The titration rate may include a dosage in terms of an amount of fluid delivered over a given period of time, e.g., at a known concentration.

Just as with IMD 14 (FIG. 1A), IMD 26 includes a posture state module that monitors the patient 12 posture state and adjusts therapy accordingly. For example, the posture state module may indicate that patient 12 transitions from lying down to standing up. In some examples, IMD 26 may automatically increase the rate of drug delivered to patient 12 in the standing position, i.e., the amount of the drug delivered per unit time, if patient 12 has indicated that pain increased when standing. This automated adjustment to therapy based upon posture state may be activated for all or only a portion of the programs used by IMD 26 to deliver therapy.

As with the examples described with respect to adjustment of one or more electrical stimulation parameters to modify electrical stimulation therapy during a transition period, one more parameters associated with the drug delivery therapy provided by IMD 26 may be modified with different modification profiles based on a detected patient posture state. Different modification profiles may determine whether the parameter value is ramped, rather than immediately changed, to a desired value from the beginning value. In the case of ramping, different modification profiles may determine different ramp rates, slopes, timing, or the like.

As an example, the rate of drug delivery to patient 12 may be increased to a desirable rate from a lesser rate based on a detected patient transition from lying down to standing up according to a ramp defined for such a posture transition. In particular, the drug delivery rate may be adjusted to the desired level by ramping up the rate of drug delivery at a constant rate of change. Such adjustments to the drug delivery rate parameter may be automatically made by IMD 26 to modify the drug delivery therapy provided to patient 12 based on the posture state detected by IMD 26.

The techniques described herein for programming IMD 14 (FIG. 1A), which provides electrical stimulation therapy may also be implemented to program IMD 26. A first set of therapy parameter values may be selected during a first phase of a programming session, during which the posture responsive therapy mode of IMD 26 is deactivated. Examples of therapy parameter values that may be programmed for IMD 26 during the first phase include, but are not limited to, a size of a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval between successive doses, and so forth.

In addition, the posture state definitions stored by IMD 14 to determine patient posture state may also be determined during the first phase of the programming session. The modification profiles, posture state definitions, and other parameters that relate to the responsiveness with which IMD 26 provides posture responsive therapy are trialed and, if necessary, modified during a second phase of the programming session, during which the posture responsive therapy mode of IMD 26 is activated. While IMD 14 is primarily referred to throughout the disclosure, the systems, devices, and techniques for programming IMD 14 are also applicable to IMD 26. Thus, any part of the techniques described herein may be performed by IMD 14, programmer 20, another computing device, or any combination thereof.

Figure 2:
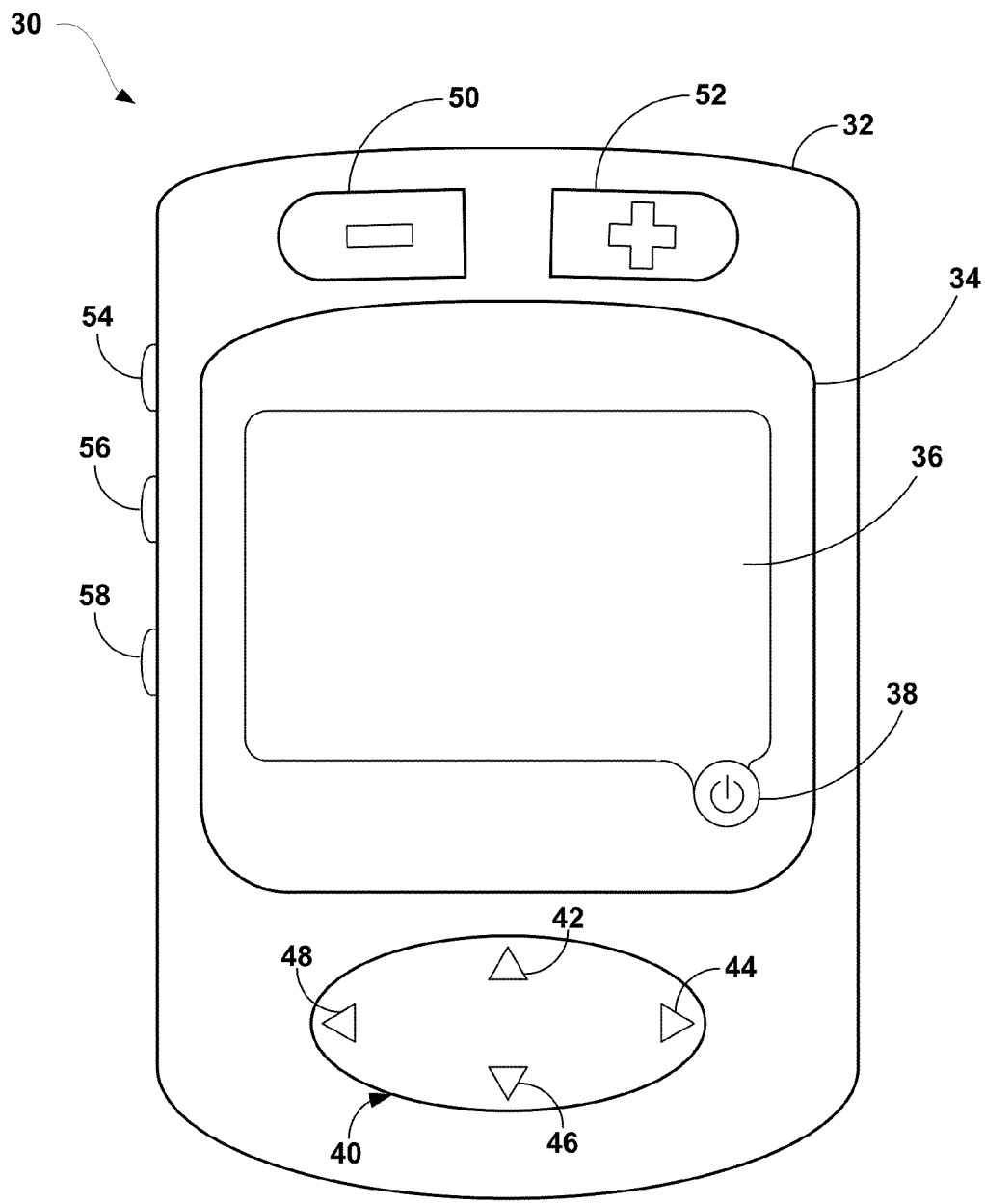
FIG. 2 is a conceptual diagram illustrating an example patient programmer for programming therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used to program either IMD 14 or IMD 26. In other examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which substantially encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during user manipulation (e.g., interaction) with patient programmer 30. Patient programmer 30 also includes control pad 40 which allows a user to navigate through items displayed on display 36 in the direction of arrows 42, 44, 46, and 48. In some examples, the buttons and control pad 40 take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects one or more highlighted items presented on display 36. In other examples, scroll bars, a scroll wheel, individual buttons, or a joystick may perform the complete or partial functions of control pad 40. In addition, in some examples, control pad 40 includes a touch pad that allows patient 12 to move a cursor within the user interface displayed on display 36 to manage therapy.

Decrease button 50 and increase button 52 provide an input mechanism for patient 12. In general, activation of decrease button 50 may decrease the value of a highlighted stimulation parameter. Buttons 50, 52 may be activated by depressing the respective button. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either button 50 and 52 is selected, patient programmer 30 may initialize communication with IMD 14 or 26 to change therapy accordingly.

When depressed by patient 12, stimulation ON button 54 directs programmer 30 to generate a command that is transmitted to IMD 14, where the command instructs IMD 14 to turn on stimulation therapy. Stimulation OFF button 56 turns off stimulation therapy when depressed by patient 12. Sync button 58 causes patient programmer 30 to communicate with IMD 14 within a substantially minimal amount of time from activation of sync button 58. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example shown in FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
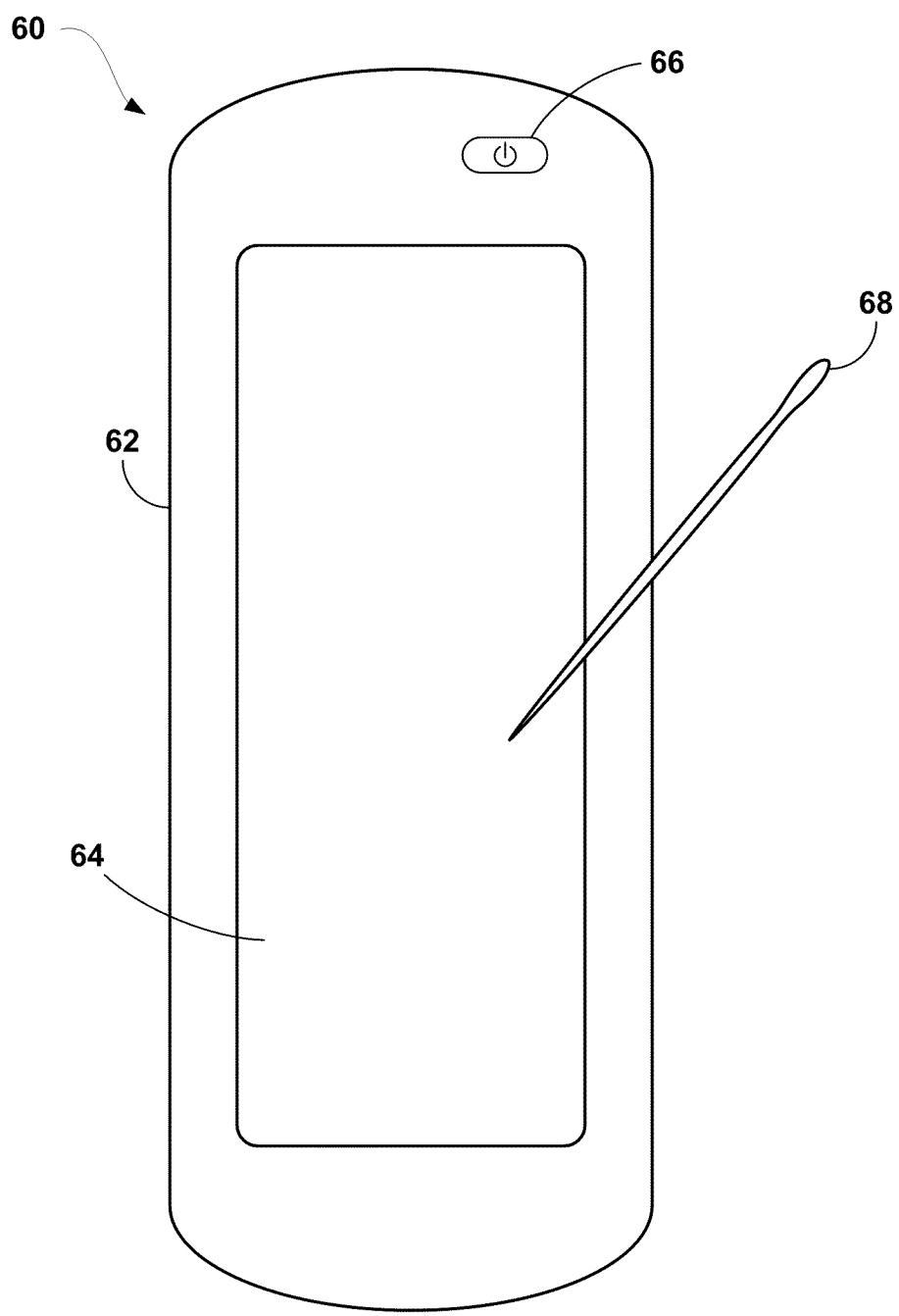
FIG. 3 is a conceptual diagram illustrating an example clinician programmer for programming therapy delivered by an implantable medical device.

FIG. 3 is a conceptual diagram illustrating an example clinician programmer 60 that may be used to program therapy delivered by an IMD, such as IMD 14 (FIG. 1A) or IMD 26 (FIG. 1C). Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example shown in FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation parameter values, modification profiles, modify therapy programs or groups, retrieve stored therapy data from an IMD or another device, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
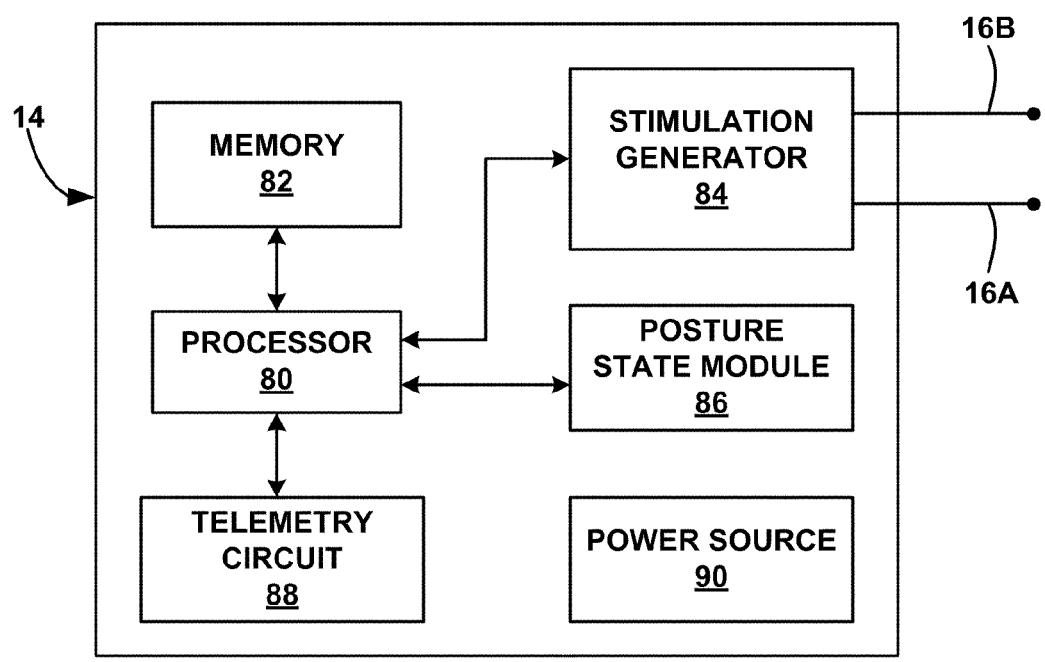
FIG. 4 is a functional block diagram illustrating various components of an implantable electrical stimulator.

FIG. 4 is a functional block diagram illustrating various components of an example IMD 14. In the example shown in FIG. 4, IMD 14 includes a processor 80, memory 82, stimulation generator 84, posture state module 86, telemetry circuit 88, and power source 90. Stimulation generator 84 forms a therapy delivery module.

Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy information, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

As one example, memory 82 may store instructions for execution by processor 80 that define one or more properties of a ramp relating to parameter adjustments, e.g., such as a rate of parameter change during a transition period. Such instructions may allow for the modification of stimulation therapy delivered by IMD 14 based on a detected posture state by making adjustments to stimulation amplitude during a transition period, in which the parameter value is ramped at the specified rate of change. As another example, memory 82 may store instructions for execution by processor 80 that define a transition period over which stimulation generator 84 transitions from therapy delivery defined by a first program to therapy delivery defined by a different therapy program in response to a posture state transition.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms, and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations on leads 16A, 16B and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations. As previously mentioned, in some example, the instructions stored in memory 82 may allow processor to control stimulation generator 84 to make parameter adjustments over a transition period, in which the parameter is ramped to the desired value.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via activity module 86. When a posture change is detected, processor 80 may determine that a modification of the stimulation therapy is appropriate, e.g., according to instructions stored in memory 82. Processor 80 may access instructions for modifying the stimulation therapy based on the posture state of patient 12, e.g., by changing from a stimulation program appropriate for the previous posture state to a stimulation program appropriate for patient's current posture state.

Depending on the parameter values defined by the respective program, an adjustment may be made to one or more or the parameter values as a result of a detected change in patient posture. Processor 80 may also adjust the parameter value over a transition period, e.g., by ramping the parameter from the existing value to the desired value of the new program according to a specific rate of change. Based on those instructions, processor 80 may control the stimulation parameter adjustment by sending an appropriate command to stimulation generator 84, which receives the command and ramps the respective stimulation parameter according to specified rate of change, thereby modifying the stimulation therapy being delivered to patient 12 based on their detected posture state.

An example range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 Hz to approximately 1200 Hz, such as approximately 5 Hz to approximately 250 Hz, or approximately 30 Hz to approximately 185 Hz, and a pulse width in the range of approximately 10 microseconds and 5000 microseconds, such as between approximately 60 microseconds and approximately 1000 microseconds, between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example shown in FIG. 4, posture state module 86 includes one or more accelerometers (e.g., one or more single axis, two-axis or three-axis accelerometers) capable of detecting static orientation or vectors in three-dimensions. Example accelerometers include a micro-electromechanical accelerometer. In other examples, posture state module 86 may alternatively or additionally include one or more gyroscopes, pressure transducers, piezoelectric crystals, or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 via patient programmer 30, or some combination thereof. As an example, processor 80 may record the posture state parameter value, or output, of a 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definition of each posture state may be illustrated as a cone in three-dimensional space. If a posture state parameter value, e.g., a sensed posture state vector, from the accelerometer of posture state module 86 is within an applicable angle or distance of a reference coordinate vector, or if the vector and the reference coordinate vector produce a cosine value in a specified cosine range, then posture state vector is determined to reside within the posture cone defined by the reference coordinate vector. Processor 80 then indicates that patient 12 is in the posture state of the posture cone. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In addition, the manual adjustment to therapy by patient 12 may be less responsive than an automated adjustment to therapy implemented by IMD 14 in response to detecting a change in a patient posture. In some examples, patient 12 may eventually be able to receive posture state responsive stimulation therapy without the need to continue making changes for different postures via patient programmer 30. Instead, patient 12 may transition immediately or over time to fully automatic adjustments based on posture state.

Although posture state module 86 is described as containing a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient posture state may be determined from multiple activity sensors placed at various locations on or within the body of patient 12.

In other examples, posture state module 86 may additionally or alternatively be configured to sense one or more additional physiological parameters of patient 12. For example, physiological parameters may include heart rate, EMG, an EEG, an ECG, temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the output of the posture state sensor in posture state module 86 to determine activity and/or posture data. For example, where the posture state sensor comprises an accelerometer, processor 80 or a processor specific to posture state module 86 may process the raw signals provided by the posture state sensor to determine activity counts. If the posture state sensor provides an analog output, processor 80 can include an analog-to-digital converter to convert the analog output of the posture state sensor to digital values.

In some examples, processor 80 may process the signals provided by the posture state sensor to determine velocity of motion information along each axis. In one example, each of the x-axis, y-axis, and z-axis signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x-axis, y-axis, and z-axis signals may be utilized to determine the patient's orientation within the gravitational field, and hence to determine the posture of the patient.

The AC component of the x-axis, y-axis, and z-axis signals yields information about patient motion. In particular, the AC component of a signal may be used to derive a value for an activity describing the patient's motion. This activity may involve a level, direction of motion, or acceleration of the patient.

One technique for determining patient activity is by determining an activity count. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12. In some examples, the threshold activity count that is used to determine whether a detected posture state of patient 12 includes an activity component (e.g., an "upright and active" posture state) is dynamic and may be changed, e.g., by a clinician during the first or second phase of the programming session, which are described in further detail below.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device via radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
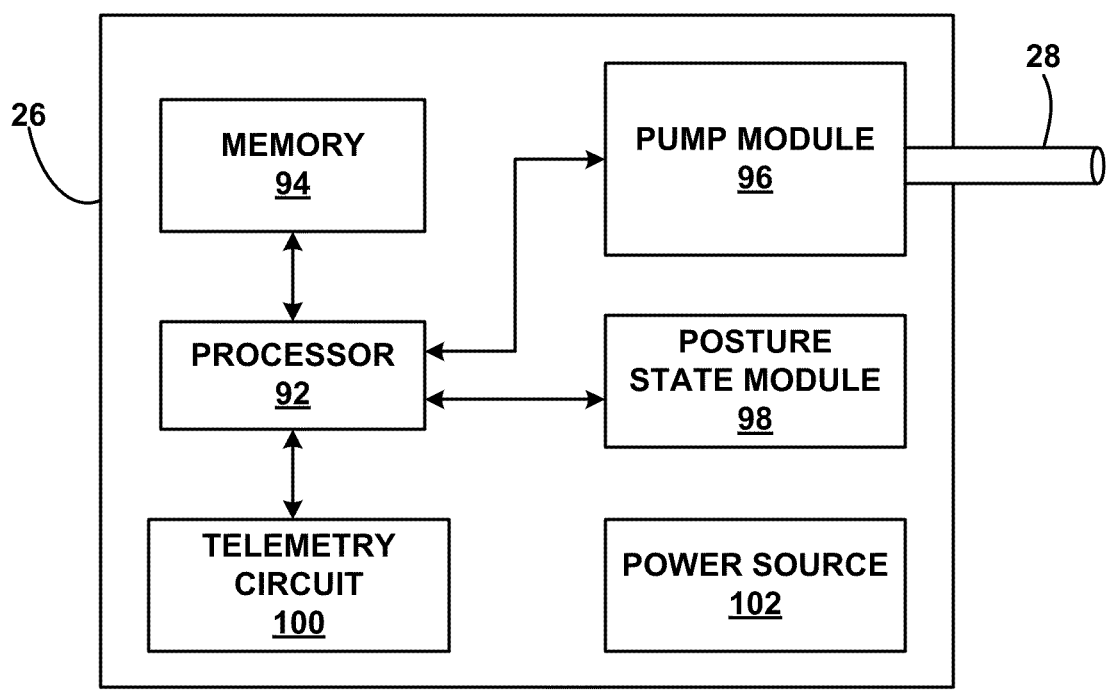
FIG. 5 is a functional block diagram illustrating various components of an implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states, e.g., adjusts their posture.

Figure 6:
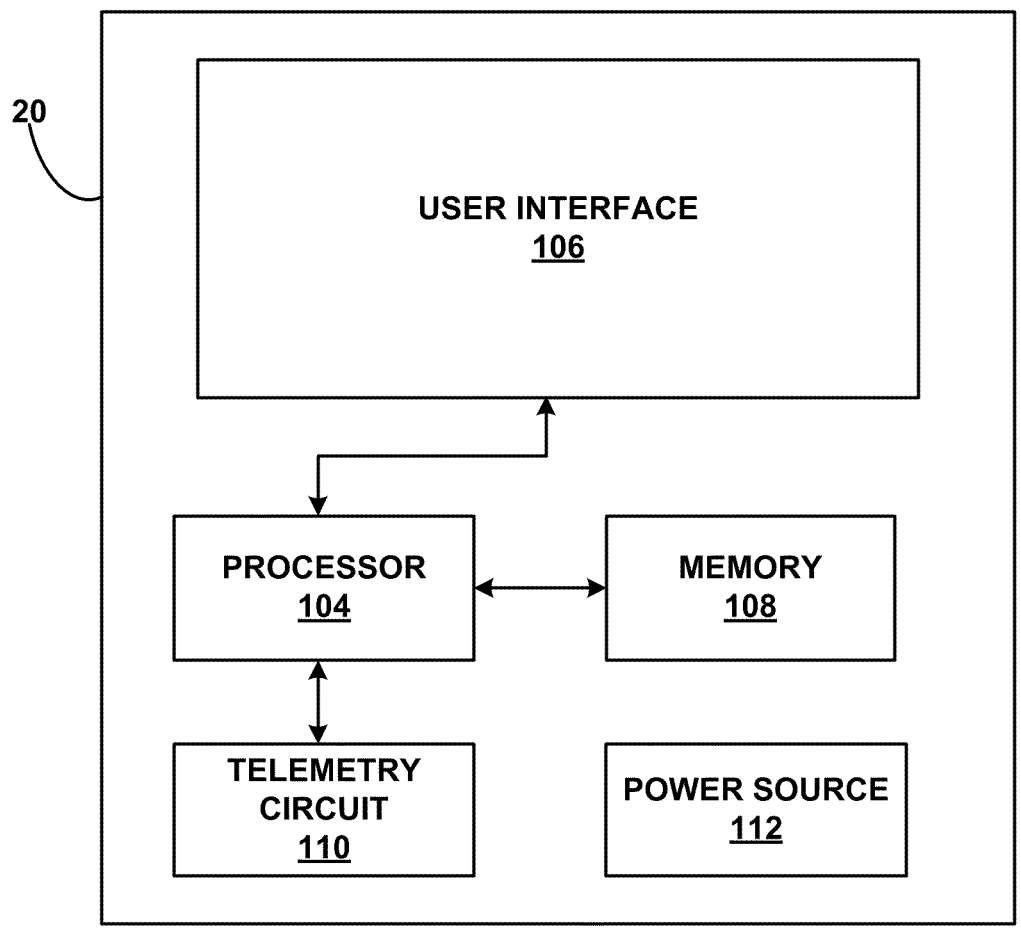
FIG. 6 is a functional block diagram illustrating various components of an external programmer for an implantable medical device.

FIG. 6 is a functional block diagram illustrating various components of an external programmer 20 for IMD 14 (or, in other examples, IMD 26). Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming IMD 14. As shown in FIG. 6, external programmer 20 includes processor 104, user interface 106, memory 108, telemetry circuit 110, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied in a hardware device via software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12 or another user (e.g., a patient caretaker) interacts with user interface 106 in order to manually change the stimulation parameters of a therapy program, switch between therapy programs within a group, switch between therapy program groups, turn posture responsive stimulation ON or OFF, view therapy information, view posture state information, or otherwise communicate with IMD 14.

User interface 106 may include a display screen and one or more input mechanisms, such as buttons as in the example of patient programmer 30 (FIG. 2), that allow external programmer 20 to receive input from a user. Alternatively, user interface 106 may additionally or only utilize a touch screen display, as in the example of clinician programmer 60 (FIG. 3). The display screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Although not shown in FIG. 6, in some examples, external programmer 20 may include a charger module capable of recharging a power source, such as a rechargeable battery that may be included in power source 90 of IMD 14. Hence, in some cases, programmer 20 may be integrated with recharging components to form a combined programmer/recharger unit.

A clinician may interact with programmer 20 to generate and/or select therapy programs for delivery in IMD 14. For example, in some examples, programmer 20 presents a user interface that supports the programming of IMD 14 in two phases, as described with respect to FIGS. 14A and 14B. Programmer 20 includes features that permit a clinician to activate or deactivate a posture responsive therapy mode of IMD 14, as well as a programming mode of IMD 14 during a programming session. For example, as described with respect to FIGS. 17A and 17B, processor 104 of programmer 20 may present a display to a user via user interface 106 that allows the user to select various modification profile parameters (e.g., transition times) and to test the posture responsive therapy features of IMD 14 with the selected modification profile parameters. The posture responsive therapy test features provided by programmer 20 permit a clinician to temporarily activate the posture responsive therapy mode of IMD 14 during a programming session, thereby enabling IMD 14 to simulate the actual posture responsive therapy mode that is programmed to be delivered to patient 12 during chronic therapy delivery by IMD 14.

Figure 7:
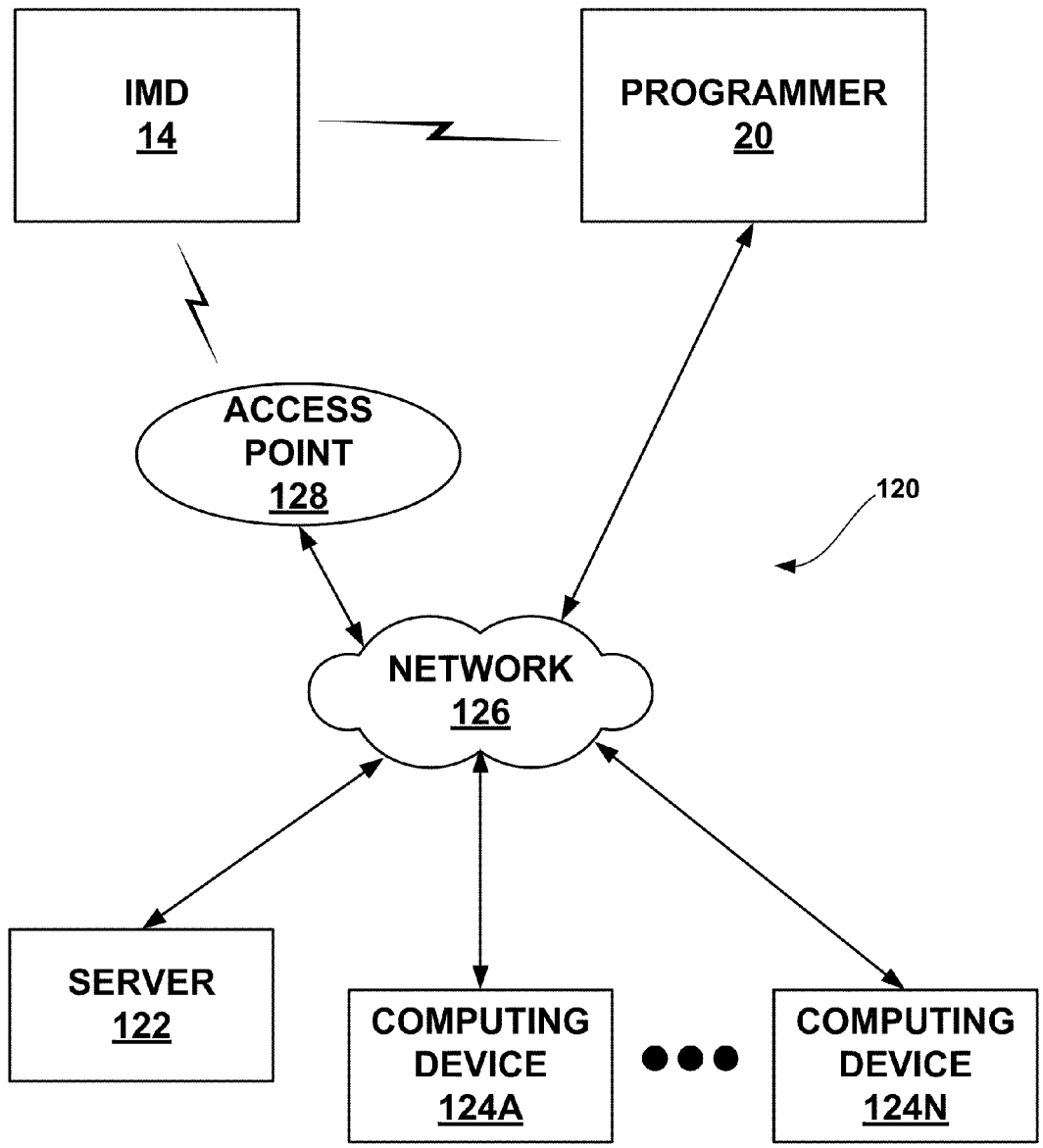
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4) to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example shown in FIG. 7, access point 128, external programmer 20, server 122, and computing devices 124A-124N are interconnected and able to communicate with each other through network 126. In some cases, one or more of access point 128, external programmer 20, server 122 or computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis.

For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

With the aid of system 120, a clinician, physician, technician, or even patient 12, may review objectivity data with respect to the posture states of patient 12. The objectivity data may include sleep quality information or proportional posture information that indicates how patient 12 has been moving during the symptom diagnosis, trial therapy delivery, or chronic therapy delivery. The user may remotely monitor the progress and trends of patient 12, thereby limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
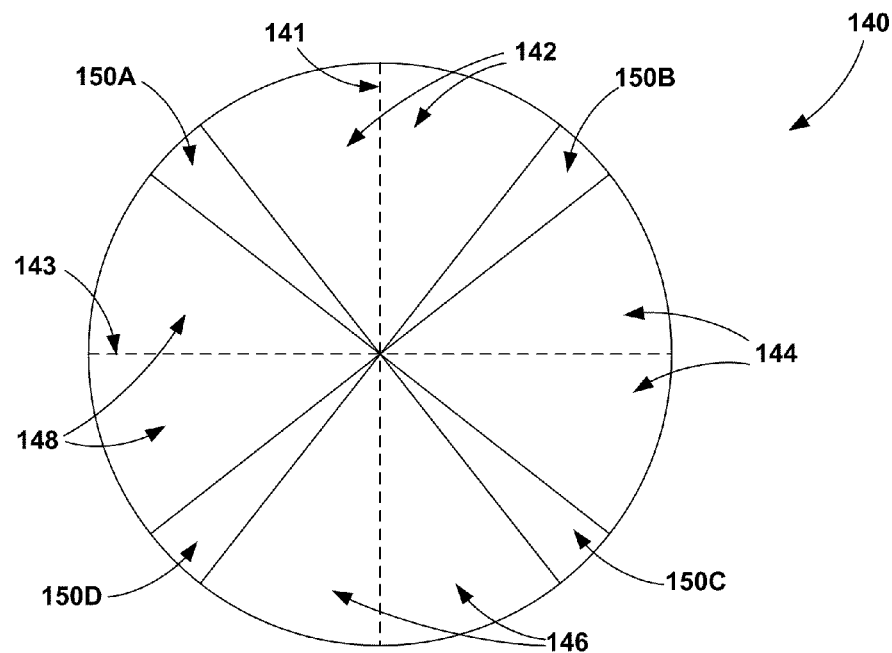
FIGS. 8A-8C are conceptual illustrations of example posture state spaces within which postures state reference data may define the posture state of a patient.
Figure 8B:
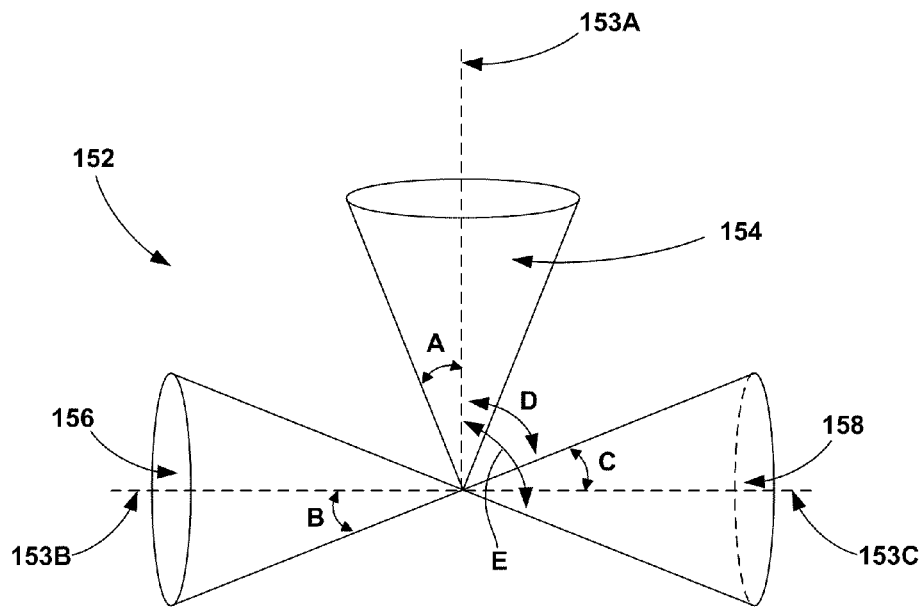
Figure 8C:
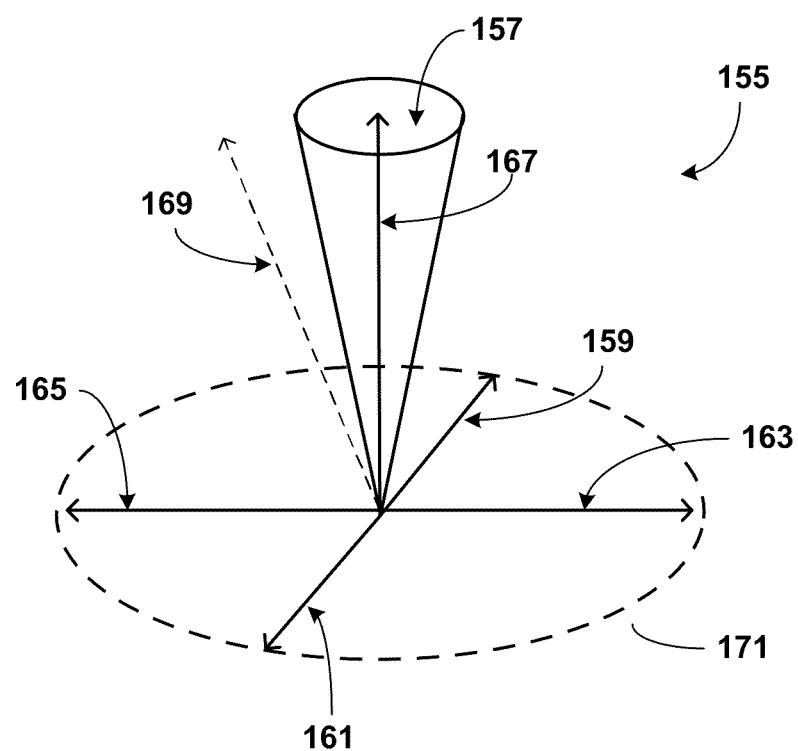

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state module 86 according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. A sense vector may be determined based on the output of the posture state sensor (e.g., based on the x, y, and/or z outputs from one or more single axis, two-axis or three-axis accelerometers). While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of 80 degrees, +40 degrees to −40 degrees from the positive vertical axis 141. In some cases, lying cones may be defined relative to the reference coordinate vector of the upright cone 142. For example, lying up cone 148 may have an angle of 80 degrees, −50 degrees to −130 degrees from the positive vertical axis 141. Inverted cone 146 may have an angle of 80 degrees, −140 degrees to +140 degrees from vertical axis 141. In addition, lying down cone 144 may have an angle of 80 degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut or toroid-like volume and the volumes of the lying posture cones. If the cones are larger such that some portions extend beyond the lying volume, then those portions can be added to the lying volume using the logical OR-like operation.

If the sensed coordinate vector resides within the donut or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 86 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 86 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 86 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
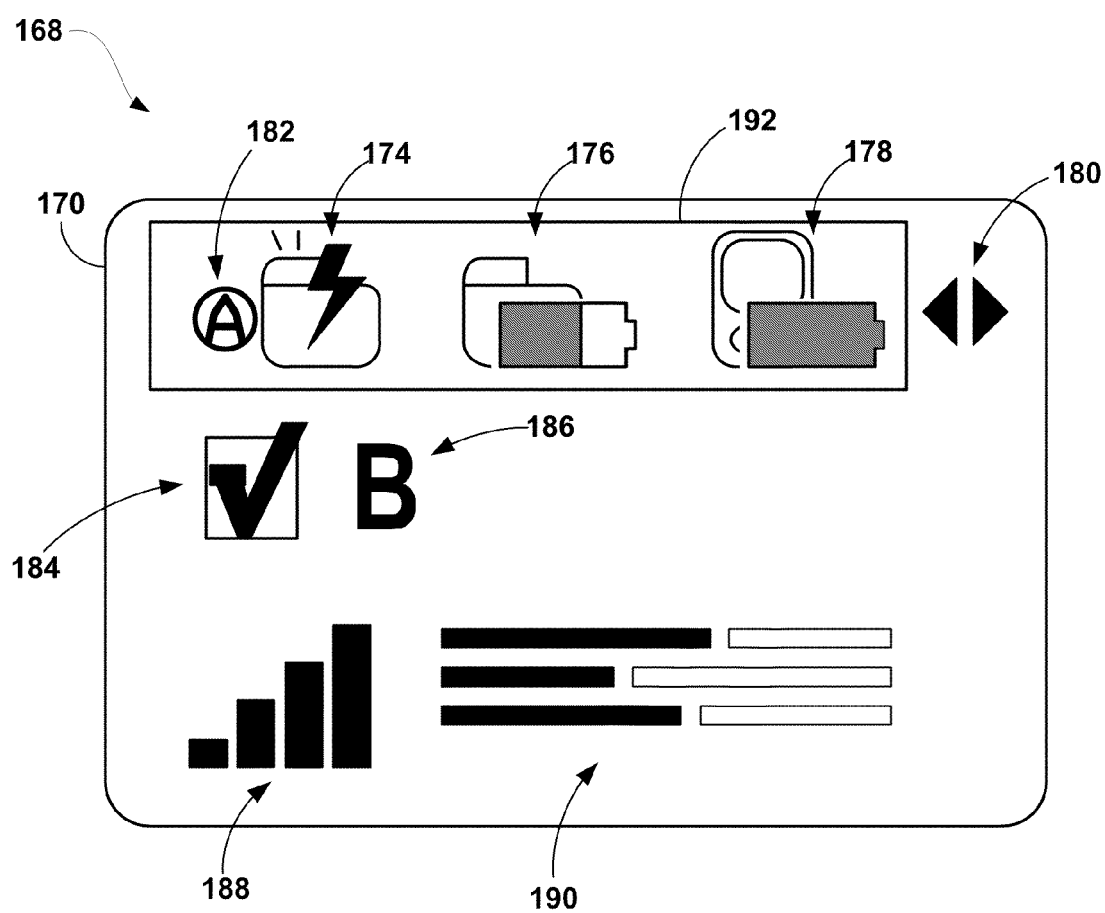
FIG. 9 is a conceptual illustration of an example user interface of a patient programmer that presents therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example shown in FIG. 9, display 36 of patient programmer 30 presents user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding therapy group, therapy program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example of screen 170 shown in FIG. 9, selection box 192 is positioned so that patient 12 may use arrows 44 and 48 (FIG. 2) of user input mechanism 40 of programmer 30 to move between an automatic posture response screen, a volume screen, a contrast or illumination screen, a time screen, and a measurement unit screen of patient programmer 30. In these screens, patient 12 may be able to control the use of the automatic posture response feature and adjust the patient programmer features. Patient 12 may only adjust the features presented within selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through stored therapy program groups, a user may use control pad 40 (FIG. 2) of programmer 30 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example shown in FIG. 9, no program number is indicated by program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that a posture responsive therapy mode of IMD 14 is activated, such that processor 80 (FIG. 4) of IMD 14 automatically adjusts therapy to patient 12 based upon the posture state detected by posture state module 86 (FIG. 4). In particular, when the posture responsive therapy mode of IMD 14 is activated, processor 80 may automatically adjust therapy delivery to patient 12 based on a detected patient posture by adjusting one or more therapy parameter values, selecting different programs or selecting different program groups based on the detected posture state of the patient. In the user interface shown in FIG. 9, automatic posture response icon 182 is not present next to group identifier 186, indicating that for therapy program group "B," IMD 14 does not provide posture responsive therapy to patient 12.

Some groups or individual programs in groups may support automatic posture responsive therapy when the posture responsive therapy mode of IMD 14 is activated. For example, automatic adjustment of one or more therapy parameter values in response to posture state indication may be selectively activated or deactivated based on settings entered by a clinician, or possibly patient 12. Hence, some therapy programs or groups may be configured for use with posture responsive therapy while other programs or groups may not be configured for use with posture responsive therapy, despite posture responsive therapy mode of IMD 14 being activated. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
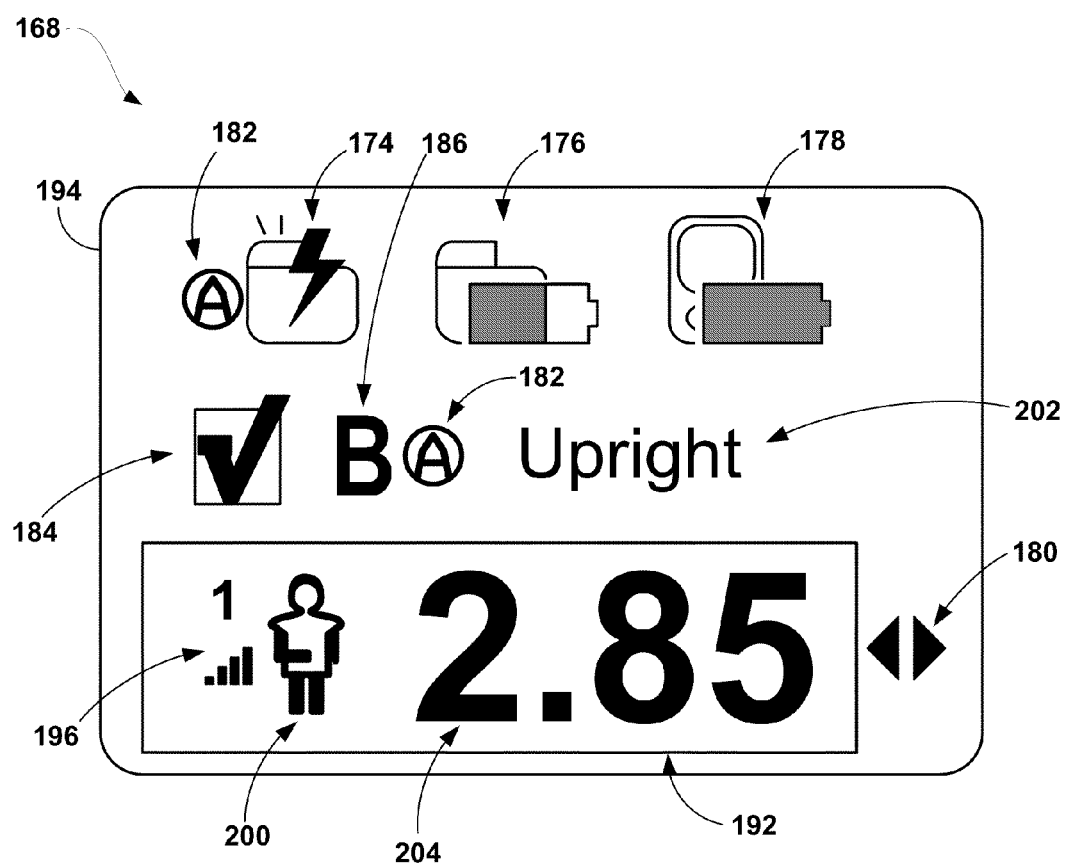
FIG. 10 is a conceptual illustration of an example user interface of a patient programmer that presents therapy information including posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Just as with screen 170 of FIG. 9, screen 194 presents stimulation icon 174, IMD battery icon 176, programmer battery icon 178, and automatic posture response icon 182. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding a therapy group, therapy program, stimulation amplitude, automatic posture response status (e.g., an indication of whether the posture responsive therapy mode of IMD 14 is activated), and posture state information. More or less information may be provided to patient 12, as desired by the clinician or the patient.

Group identifier 186 indicates that therapy group "B" is active, and automatic posture response icon 182 indicates group "B" (containing one or more programs) is activated to allow IMD 14 to automatically adjust therapy according to the patient posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194. In the example shown in FIG. 10, an amplitude value 204 illustrating the current voltage amplitude of program "1" of 2.85 Volts is presented to the user. Patient 12 (or another user) may scroll through different programs of the group by using navigation arrows 180 via arrows 44 and 48 of control pad 40 (FIG. 2).

Posture state indication 200 shows that IMD 14 is detecting that patient 12 is in the upright or standing posture based on posture state module 86 (FIG. 4). Supplementary posture state indication 202 supplements posture state indication 200 by providing a textual indication of the exact posture being detected by posture state module 86 of IMD 14. Posture state indication 200 and supplementary posture state indication 202 presented via user interface 168 change according to the sensed, or detected, posture state detected by IMD 14. The posture state may be communicated to external programmer 20 substantially immediately after IMD 14 detects a posture change, periodically communicated to programmer 20, or non-periodically communicated by IMD 14 unilaterally or upon receiving a request from programmer 20. Accordingly, the posture state indication 200 and/or supplementary posture state indication 202 may represent a current, up-to-the minute status (e.g., a real-time patient posture state), or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 180. Selection box 192 may be moved to select other screen levels with control pad 40 of programmer 20 (FIG. 2) in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

When a posture responsive therapy mode of IMD 14 is activated, processor 80 automatically modifies stimulation generated and delivered by stimulation generator 84 based on posture state of a patient, e.g., by adjusting one or more stimulation parameters according to a modification profile that varies according to a type of posture state transition undertaken by the patient. For some posture state transitions, therapy parameter value modifications may be performed gradually, rather than by immediately changing the parameter value. For example, based on the detected posture state transition of a patient, an IMD may ramp-up and/or ramp-down a stimulation parameter value during a transition period to a desirable parameter value from the value previously programmed to be delivered. Either the ramp rate or the transition period may be defined by a modification profile. Alternatively, for other posture state transitions such as upright to lying down, the IMD may immediately drop a parameter value, e.g., voltage amplitude, to a lower value. In this manner, the IMD may reduce the likelihood that the patient will experience discomfort as a result of the posture state transition.

Figure 11A:
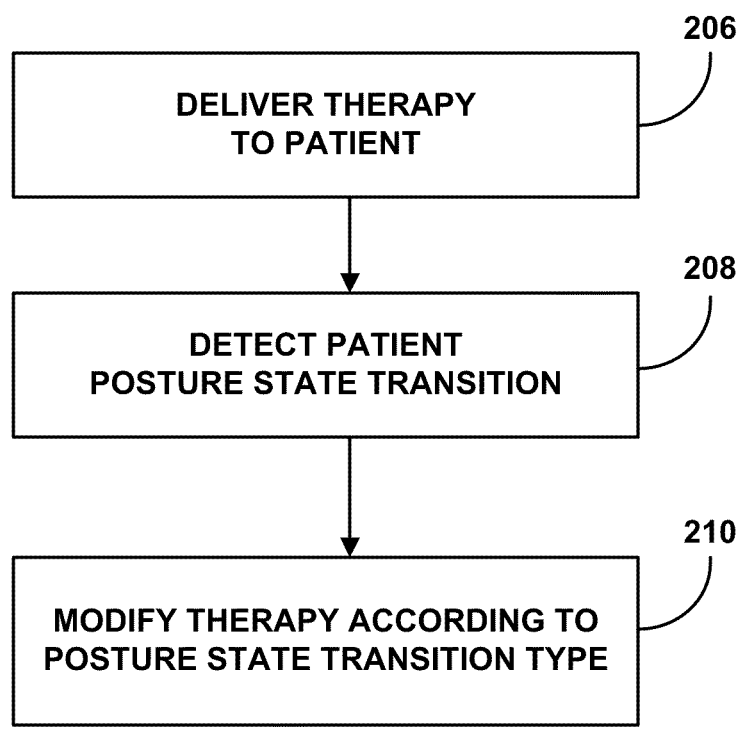
FIGS. 11A and 11B are flow diagrams illustrating example techniques for modifying stimulation therapy based on patient posture state transitions.
Figure 11B:
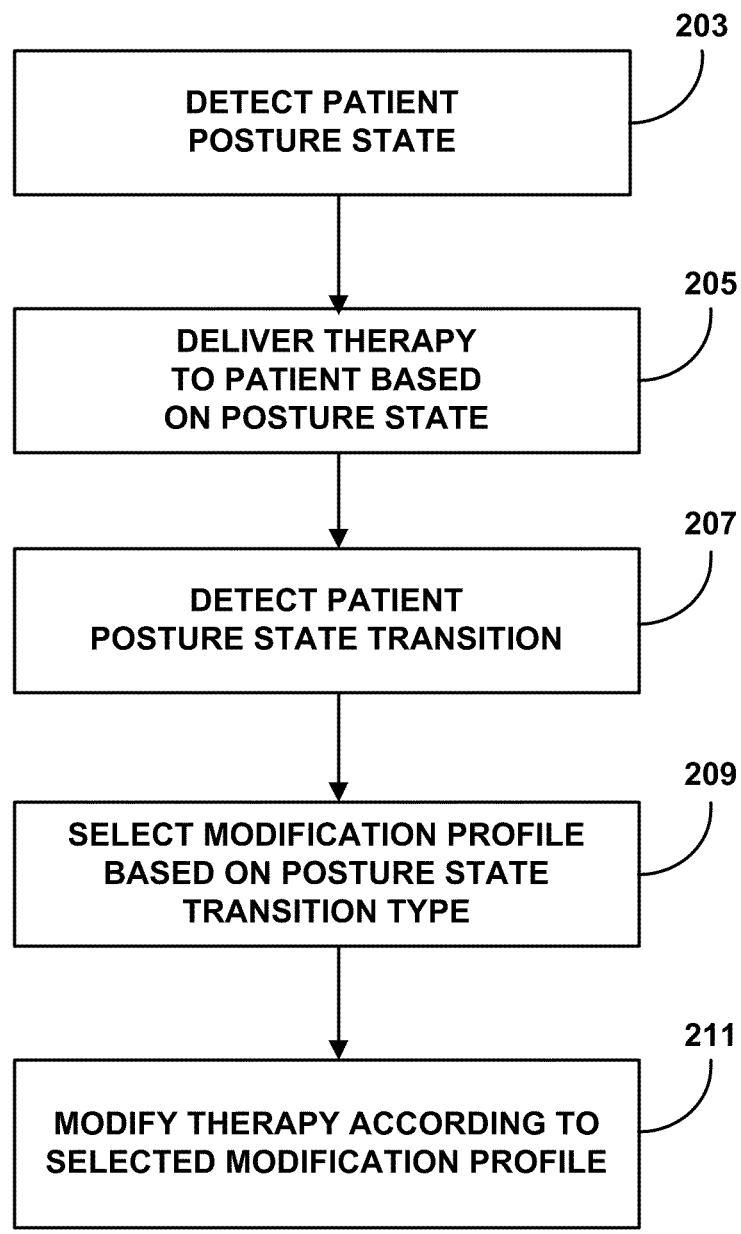

FIGS. 11A and 11B are flow diagrams illustrating example techniques processor 80 implements to modify stimulation therapy based on patient posture state transitions when a posture responsive therapy mode of IMD 14 is activated. For purposes of illustration, the example techniques will be described with respect to implantable stimulation system 10 described herein. However, such a technique may be implemented by any suitably configured system utilized to provide electrical stimulation therapy to a patient, such as, e.g., implantable stimulation system 22 described herein. Further, utilization of such an example technique is not limited to electrical stimulation therapy. Rather, in some examples, such a technique may be implemented in other patient therapy systems, including those configured to provide drug delivery therapy, e.g., implantable drug delivery system 24 described herein.

In addition, while the techniques described with respect to FIGS. 11A and 11B, as well as FIGS. 13, 14A, 14B, 15, and 16 are described as being performed by processor 80 of IMD 14 and/or processor 104 of programmer 20, in other examples, the techniques may be performed by any device or any combination of devices.

Referring to FIG. 11A, processor 80 controls stimulation generator 84 to generate and deliver therapy to patient 12 (206), e.g., in the form of electrical stimulation pulses delivered to patient 12 via stimulation leads 16A and 16B (FIG. 1) (206). As previously described, stimulation generator 84 may generate the stimulation signals according to the therapy parameter values defined by one or more therapy programs. The specific parameter values defined by the therapy programs may provide efficacious therapy to patient 12 for a particular posture state of patient 12. Thus, upon detection of the posture state by posture state module 86 (FIG. 4), processor 80 may control stimulation generator 84 to generate and deliver therapy to patient 12 according to the one or more therapy programs associated with the detected posture state. In some examples, the associations between therapy programs and patient posture states are stored by memory 82 of IMD 14. As an example of how therapy is delivered in accordance with the posture responsive therapy mode of IMD 14, if processor 80 detects that patient 12 is lying down based on input from posture state module 86, processor 80 controls stimulation generator 84 to generate and deliver stimulation signals in accordance with the therapy program associated with the lying down state. In this way, IMD 14 may deliver a stimulation signal having a stimulation amplitude and/or other parameters that are appropriate for patient 12 when lying down.

While providing therapy to patient 12, processor 80 may detect a patient posture state transition (208). Based on the type of posture state transition, processor 80 modifies the therapy delivery to patient 12 (210). In particular, processor 80 of IMD 14 may modify stimulation using a modification profile that corresponds to the patient posture state transition detected by the posture state module. For example, if the posture state transition is from an upright posture state to a lying down posture state, processor 80 may apply a modification profile that immediately drops the amplitude of the stimulation from an existing level (for the upright posture state) to a desired level (for the lying down posture state). A plurality of posture state definitions and associated modification profiles may be stored in memory 82 of IMD 14. If the posture state transition is from a first lying state to a second, different lying state, from a first upright state to a second, different upright state, or from a lying state to an upright state, processor 80 may apply a modification profile that ramps amplitude upward or downward according to a more gradual ramp profile. However, ramp characteristics such as timing, slope or the like may vary according to the particular posture state transition that is detected or the stimulation parameter value that is modified. For example, different posture state transitions may dictate different modification profiles.

In accordance with the technique shown in FIG. 11A, processor 80 of IMD 14 automatically modifies the stimulation therapy being delivered to patient 12 based on a detected posture state transition (210). In the case of stimulation therapy, processor 80 modifies therapy delivery from a set of therapy parameter values (e.g., a therapy program) configured for delivery to patient 12 in one posture state to a set of therapy parameter values configured for delivery to patient 12 when in another posture state. Processor 80 may apply a modification profile that controls the way in which the modification is made, e.g., immediate drop or gradual ramp. As an example, if a stimulation program appropriate for patient 12 when standing defines an amplitude of Y volts, and the stimulation program appropriate for patient 12 when lying down defines an amplitude of X volts, then the modification profile determines the manner in which amplitude is modified from Y to X or X to Y In other examples, the amplitude of stimulation therapy may be a current amplitude (e.g., amps), or defined in terms of energy (e.g., Coulombs).

To modify the electrical stimulation therapy as described, e.g., for a transition from lying down to upright, processor 80 controls stimulation generator 84 such that the amplitude of stimulation provided to patient 12 increases in value from X volts to Y volts. However, the adjustment from X volts to Y volts may not occur substantially immediately, but instead may be gradually adjusted (e.g., ramped up or down) over a ramp period. During the ramp period, processor 80 controls stimulation generator 84 such that the stimulation amplitude value may be ramped up from a value of X volts to a value of Y volts over a transition period of n seconds. For example, processor 80 may control stimulation generator 84 such that the amplitude value of the stimulation provided to patient 12 is increased at a constant rate, starting at X volts and ending at Y volts. In other examples, a rate that is not constant may be used to adjust the amplitude value.

For a transition from upright to lying down, however, processor 80 may modify therapy according to a different modification profile. For example, processor 80 may control stimulation generator 84 to substantially immediately drop the amplitude from Y volts to X volts. In this case, the substantially immediate drop in amplitude represents a modification profile that is different from a modification profile in which the amplitude is gradually ramped. Using such a technique, processor 80 of IMD 14 may modify stimulation therapy to patient 12 based on the posture state transition of patient 12 by adjusting one or more stimulation parameter values by ramping from a first programmed amplitude value to a second programmed amplitude value. Although the modification profile is generally described in terms of the rate of change of a therapy parameter value from an existing value to a desired target value, another aspect of a modification profile may include a dwell time that precedes activation of the modification, as described in further detail with reference to FIG. 12 below.

FIG. 11B illustrates another example technique for modifying stimulation therapy based on patient posture state transitions. As shown in FIG. 11B, upon detecting a patient posture state (203), processor 80 controls stimulation generator 84 to deliver stimulation to a patient based on the posture state (205). In particular, processor 80 may adjust therapy by adjusting one or more therapy parameters or selecting one or more different programs or groups based on the posture state occupied by the patient, e.g., upright, upright and active, lying (front), lying (back), lying (right), lying (left). Lying (front), lying (back), lying (right) and lying (left) posture states refer to postures states in which the patient is lying down on his front, back, right side or left side, respectively.

Upon detecting a patient posture state transition (207), processor 80 modifies therapy according to the new posture state. Processor 80 selects a modification profile based on the type of the posture state transition (209). The modification profiles may be stored by memory 82 of IMD 14 or a memory of another device, such as programmer 20. Examples of different posture state transition types include upright to upright and active, upright and active to upright, upright to different lying down posture states, upright and active to different lying down posture states, different lying down postures states to upright or upright and active, or a transition between different lying down posture states.

Modification profiles may be stored as modification profile data for all or a subset of the transition types, and may indicate a dwell time, and a ramp rate and/or transition period, and, in some cases, other characteristics to be implemented in the modification, or any combination thereof. In some examples, the modification profile does not include either or both the ramp rate and transition period. As previously indicated, IMD 14 may implement a ramp rate and/or transition time that are independent of the posture state transition. For example, the ramp rate or transition time may be selected based on whether the stimulation parameter value (e.g., amplitude) is increasing or decreasing in response to a detected posture state transition. Upon selection of the appropriate modification profile for the detected posture state transition (209), processor 80 modifies therapy according to the selection modification profile (211). The ramp rate, transition period, dwell time or the like may differ for different posture state transitions, depending on the modification profiles associated with the posture state transitions. For example, a transition from upright to upright and active may require a relatively gradual up-ramp, whereas a transition from upright to a lying down posture state may require an abrupt down-ramp to quickly change amplitude.

Table 1 below illustrates an example of different modification profiles associated with different posture state transition types.

TABLE 1

| POSTURE STATE TRANSITION | MODIFICATION PROFILE |
| --- | --- |
| Upright to Active and Upright | 1 |
| Upright to Lying (Front) | 2 |
| Upright to Lying (Back) | 3 |
| Upright to Lying (Right) | 4 |
| Upright to Lying (Left) | 5 |
| Upright and Active to Upright | 6 |
| Upright and Active to Lying (Front) | 7 |
| Upright and Active to Lying (Back) | 8 |
| Upright and Active to Lying (Right) | 9 |

TABLE 1-continued

| POSTURE STATE TRANSITION | MODIFICATION PROFILE |
|---|---|
| Upright and Active to Lying (Left) | 10 |
| Lying (Front) to Upright | 11 |
| Lying (Front) to Upright and Active | 12 |
| ... | ... |
| Lying (Left) to Lying (Right) | 30 |

In some examples, posture state module 86 of IMD 14 detects six different posture states, and there may be up to thirty different posture state transitions between those six posture states. Each modification profile shown in Table 1 above may be unique in the sense that it defines different rates of change, transition periods, dwell times, or the like. Alternatively, some of the modification profiles may be the same for different posture state transition types. For example, transitions to or from any of the lying down posture states could have the same modification profiles.

Figure 12:
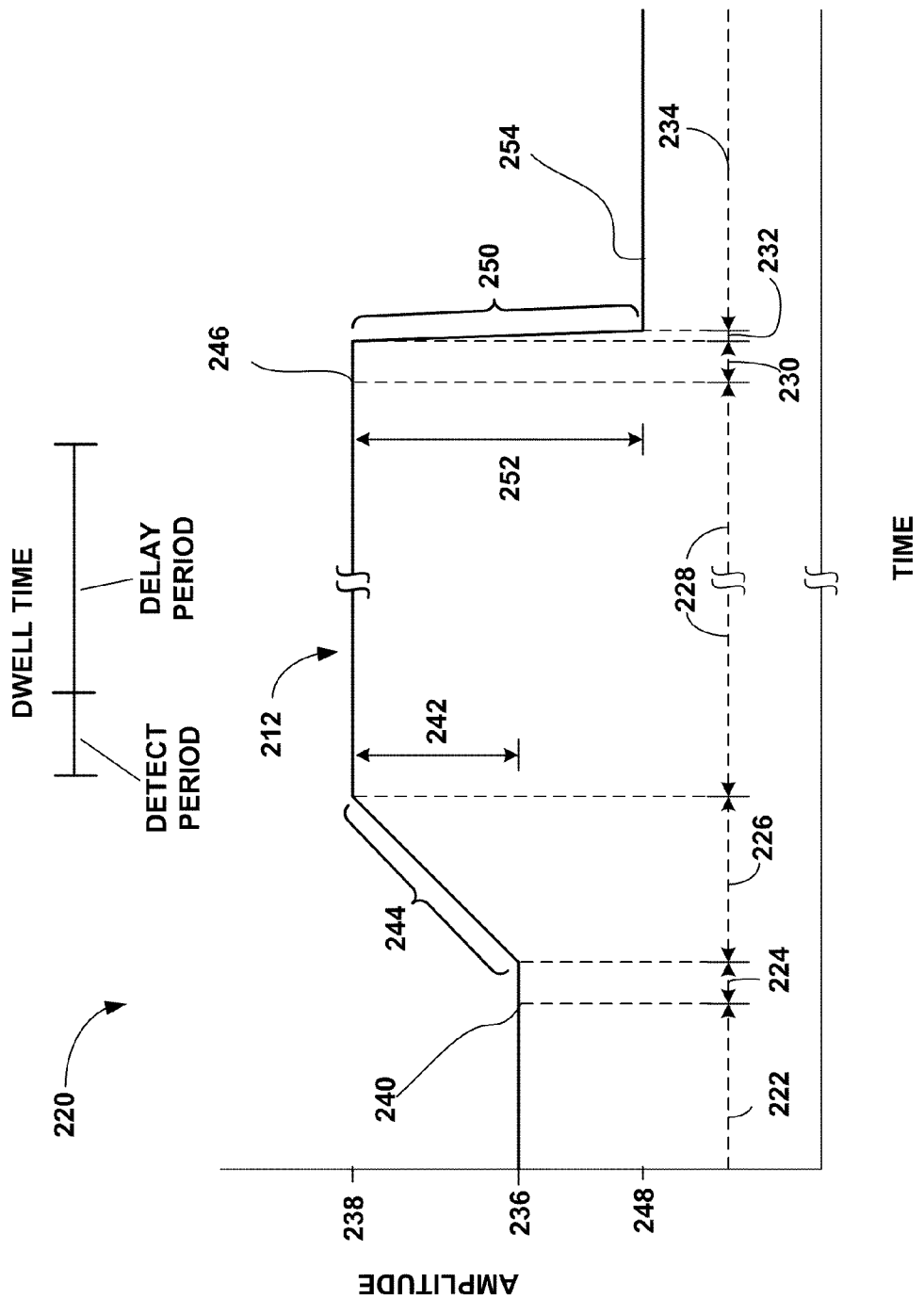
FIG. 12 is a plot illustrating the amplitude value of an example stimulation therapy provided to a patient over a period of time.

FIG. 12 is a plot 220 illustrating the amplitude value of an example stimulation therapy provided to patient 12 over a period of time. Plot 220 includes a line 212 that represents the amplitude value of stimulation pulses being delivered, e.g., by IMD 14, as part of stimulation therapy provided to patient 12 with respect to time. In the example illustrated, the stimulation therapy may be automatically modified based on the posture state of patient 12 detected by posture state module 86 (FIG. 4) of IMD 14. The modification may have a modification profile, e.g., slow ramp, medium ramp, fast ramp, or immediate increase or decrease, which varies according to the posture state transition. As one example, plot 220 may be representative of the amplitude value of stimulation therapy delivered in part according to a technique similar to that described with respect to FIGS. 11A and 11B.

As indicated by FIG. 12, the variable of time is represented along the x-axis of plot 220 and the variable of amplitude is represented along the y-axis of plot 220. As previously noted, amplitude may refer to current amplitude or voltage amplitude of stimulation signals. In addition, for purposes of illustration, the time variable of plot 220 has been divided into time periods 222, 224, 226, 228, 230, 232, and 234. During time period 222, patient 12 may occupy a posture state that can be characterized as upright, and is detected by IMD 14 as such. Accordingly, processor 80 controls stimulation generator 84 to provide patient 12 with stimulation therapy to effectively address symptoms experienced by patient 12 while upright. For example, processor 80 may select a therapy program from memory 82 that is associated with the upright posture and is believed to provide efficacious therapy to patient 12 in the upright posture. In the example shown, the amplitude parameter of such stimulation therapy is provided at a first amplitude value 236.

In the example shown in FIG. 12, patient 12 maintains the upright posture until time 240, at which time patient 12 begins to walk. At this time, the posture state transitions from upright to upright and active. The upright and active posture state may correspond to a stimulation therapy program specifying a modification of the amplitude parameter to second amplitude value 238. In addition, the transition from upright to upright and active corresponds to a modification profile characterized by a ramp 244. As indicated by FIG. 12, second amplitude value 238 is greater than first amplitude value 236 by approximately the amount represented by line 242.

According to plot 220, patient 12 continues to walk throughout time periods 224, 226, and 228. However, as indicated by plot 220, IMD 14 may not immediately respond to the posture transition of patient 12 from upright to upright and active. Instead, during a dwell time period 224, processor 80 detects the posture transition by patient 12 and imposes a delay period before modifying therapy delivery. For example, during dwell time period 224, processor 80 may process information received from patient posture module 86 using instructions stored in memory 82 to detect that patient 12 has transitioned from upright to upright and active.

In some examples, dwell time period 224 may represent a duration of time between the detection of a posture state transition and the activation of a change in a parameter such as amplitude, while in other examples, dwell time period 224 represents a duration of time between the actual posture state transition and the adjustment to the therapy. Dwell time period 224 may be a part of a modification profile that is associated with the posture state transition. This duration of time may be referred to as a dwell time, which may be a combination of a detection period and a delay period, e.g., as shown in FIG. 12. The length of the detection period may depend on parameters and sampling frequency with which posture state module 86 detects a posture state. The detection period generally refers to a period of time during which a posture state detection has reached a reliable, steady state indication of the patient posture state. The detection period should be relatively short to provide accurate and responsive posture detection performance during use of the posture responsive therapy mode of IMD 14.

The delay period may be user defined, and, in the example shown in FIG. 12, is longer than the detection period. The dwell time period 224 represents a period of delay that occurs prior to ramping the amplitude (or other stimulation parameter) to the posture-specific amplitudes for the programs in a group. Some patients may not experience increased or decrease symptoms, such as pain, until they have been in a posture for an extended period of time. The delay period aspect of the dwell time accounts for these patient considerations.

Once it is determined that a posture state transition has occurred following a detection period of the dwell time, and the delay period of the dwell time has expired, processor 80 controls stimulation generator 84 to begin modifying the amplitude level from a first amplitude level associated with the previous posture state, e.g., upright, to a second amplitude level associated with the newly detected posture state, e.g., upright and active. In some examples, the modification to the stimulation amplitude is performed according to a parameter defined by the modification profile associated with the posture state transition from the upright posture state to the upright and active posture state.

Although plot 220 indicates dwell time periods 224 and 230 (which is described below) are significant amounts of time relative to the duration of therapy delivery, in some examples, the relative amount of the detection period required to detect the posture transition of patient 12 may be minimal compared to the duration of therapy delivery, such that the detection period is relatively insignificant for the purposes of the described technique. For example, the amount of time required for a detection period may be on the order of seconds, tens or hundreds of milliseconds or less depending on the technique used to detect the posture state of patient 12. In some examples, the amount of time required for a detection period may be less than or equal to 1 second. For example, the amount of time required for a detection period may range from approximately 100 milliseconds to approximately 1 second, such as 300 milliseconds to 400 milliseconds.

The length of the delay period may be user defined to be different for different posture state transitions. Hence, the total duration of the dwell time for a transition from upright to upright and active may be different than the dwell time for a transition from upright and active to lying down. The dwell time represented by time periods 224 and 230 may be fixed for all posture state transitions or vary for different posture state transition types, e.g., according to user defined time periods. In some examples, the length of one or more dwell times may be programmed by a user, such as a patient or clinician, e.g., using one or more of programmers 20, 30 and 60 to program IMD 14 as previously described.

In some examples, the duration of a delay time period may be on the order of seconds, while in other examples the duration of a delay time period may be on the order of minutes. For example, for posture state transitions to an upright posture state, the length of a delay time period may range from approximately one second to approximately five minutes, such as approximately five seconds to approximately 60 seconds. As another example, for posture state transitions to a lying posture state, the duration of the delay time period may range from approximately 0 seconds to approximately 2 minutes, such as approximately 0 seconds to 10 seconds. As another example, for posture state transitions to an upright and active, e.g., walking, the duration of a delay time period may range from approximately 10 seconds to approximately 10 minutes, such as approximately 30 seconds to approximately five minutes, such as approximately two minutes to approximately five minutes.

In the example shown in FIG. 12, once IMD 14 has detected a posture transition of patient 12 from upright to upright and active, IMD 14 may automatically modify the stimulation therapy, e.g., to effectively address the symptoms experienced by patient 12 while walking. As illustrated by line 212, the stimulation therapy modification includes increasing the amplitude parameter value from first amplitude value 236 to second amplitude value 238. Processor 80 controls stimulation generator 84 to increase the amplitude of stimulation pulses delivered to patient 12 based on patient's posture state. Specifically, processor 80 may determine that a stimulation amplitude equal to that of second amplitude value 238 is appropriate based on one or more stimulation programs stored in memory 82 that correspond to the posture state of upright and active, as indicated by walking or other upright activity.

As indicated by the timing diagram shown in FIG. 12, IMD 14 may not instantaneously increase the amplitude parameter value of the stimulation therapy from amplitude 236 to amplitude 238 once the patient's posture state transition is detected and time period 224 expires. Instead, processor 80 controls stimulation generator 84 to transition the amplitude parameter of the stimulation therapy from first amplitude value 236 to second amplitude value 238 during a transition period 226. In particular, the amplitude parameter is ramped up from first amplitude value 236 to second amplitude value 238 beginning at the start of transition period 226, increasing at a rate of change equal to that of the slope of line 212 during transition period 226, i.e., the slope of ramp portion 244, and ending at approximately the end of transition period 226. The slope of portion 244 is equal to that of the difference 242 between first amplitude value 236 and second amplitude value 238, divided by the length of time period 226.

In this example, IMD 14 does not first drop the stimulation amplitude to approximately zero prior to ramping up the stimulation amplitude to second amplitude value 238. Instead, IMD 14 begins the stimulation amplitude adjustment to value 238 directly from first amplitude value 236. However, in some examples, other techniques may be employed. For example, instead of ramping up the stimulation intensity directly from value 236, IMD 14 may first drop to the stimulation amplitude to a lower value e.g., approximately zero, and then ramp up the stimulation amplitude to second value 238 to adjust the stimulation amplitude.

In general, the rate of change corresponding to the slope of portion 244 provides a gradual stimulation amplitude adjustment while maintaining effective stimulation therapy to patient 12. In some cases, if the amplitude value of stimulation therapy is increased too quickly, patient 12 may experience discomfort. In contrast, if the stimulation amplitude of stimulation therapy is modified too slowly, patient 12 may not be provided with appropriate stimulation therapy soon enough following a posture transition, leading to the patient experiencing symptoms that the modified therapy is meant to address. In this way, the transition period for the therapy modification affects the responsiveness of the posture responsive therapy provided by IMD 14. In some examples, the amplitude parameter value represented by line 212 may be increased during transition period 226 to allow for an adjustment of the stimulation amplitude value without resulting in patient discomfort. This may include patient discomfort as a result of increasing the amplitude value at too great of a rate, or increasing the amplitude value at too slow of a rate, as described.

In some examples in which the stimulation amplitude value is a voltage amplitude, the rate of change corresponding to the slope of portion 244 may be on the order of volts or millivolts per second. For example, the rate of change corresponding to the slope of portion 244 may range from approximately 1 volt per second to approximately 3 volts per second. In some cases, the rate of change corresponding to the slope of portion 244 may be inversely proportional to the length of dwell time period 244. Furthermore, in some examples, the length of time of transition period 226 may be on the order of minutes or seconds. For example, the length of time of transition period may range from approximately 0.1 seconds to approximately 10 seconds, such as approximately 0.5 seconds to approximately 2 seconds. In some examples, the amplitude difference represented by line 242 may be on the order of volts or millivolts in examples in which the stimulate amplitude value is a voltage amplitude. In some examples, the amplitude difference represented by line 242 may be up to approximately 10.5 volts. For example, the amplitude difference represented by line 242 may range from approximately 1 volt to approximately 3 volts, such as approximately 1.5 volts to approximately 2 volts.

In some cases, the suitability of a ramp adjustment may be unique to the type of posture state transition that results in the modification to the stimulation therapy. For example, the rate of change suitable for a ramp adjustment associated with an amplitude adjustment due to a patient's posture state transition from lying down to upright may be different than a rate of change for a ramp adjustment that is suitable for an amplitude adjustment based on the same patient's posture state transition from upright to upright and active. Consequently, in some examples, IMD 14 is configured to utilize a rate of change specific to the type of posture state transition that resulted in the therapy modification to adjust stimulation amplitude.

Just as different posture states may be associated with different amplitudes, different posture state transitions may be associated with different modification profiles, such as different ramp rates, transition periods, and the like. In the example shown in FIG. 12, the rate of change during time period 226 may be defined based on the patient's transition from an upright posture to an upright and active posture. For other posture state transitions, such as upright to lying down, different rates of change may be defined for modification of one amplitude value to another amplitude value. Such information may be stored by memory 82 of IMD 14, e.g., in a data table or another suitable data structure that associates a rate of change to one or more detectable posture state transitions. Processor 80 may access the therapy modification rate information upon detecting a patient posture change. In this manner, the modification may be made according to a particular ramp adjustment that is appropriate based on the particular patient posture state transition that caused the modification in stimulation therapy.

To detect posture state transitions, processor 80 may periodically determine the posture state occupied by patient 12. In one example, processor 80 of IMD 14 compares the current posture state of patient 12 detected via posture state module 86 to a previously detected posture state of patient 12, e.g., the posture state detected just prior to the current posture state, which may be stored in memory 82. If the two detected posture states are the same, processor 80 may continue to deliver electrical stimulation without modification. However, if the two detected posture states are different, processor 80 may modify the stimulation therapy by controlling stimulation generator 84 to adjust the amplitude parameter value according to a corresponding modification profile, e.g., as defined by the stimulation program corresponding to the new posture state occupied by patient 12, as described herein.

IMD 14 alternatively or additionally may be configured to utilize a rate of change specific to the type of amplitude adjustment being made to adjust stimulation amplitude. In general, any amplitude adjustment made by IMD 14 may be characterized as either an increase or decrease in the stimulation amplitude value. Accordingly, in some examples, processor 80 may adjust stimulation amplitude according to the same rate of change for all amplitude adjustments that increase the amplitude value, and may also adjust stimulation amplitude according to the same rate of change for all amplitude adjustments that decrease the amplitude value. For example, processor 80 may execute every amplitude increase according to substantially the same rate, regardless of the overall amplitude increase. As a result, in such cases, the transition period associated with the amplitude adjustment may vary according to the overall amplitude increase.

As another example, IMD 14 may be configured to utilize a rate of change that is specific to each posture state occupied by a patient, rather than a posture state transition, to adjust stimulation amplitude. For example, IMD 14 may automatically adjust stimulation amplitude to a desired value according to approximately the same rate of change any time IMD 14 detects that patient is in a specific posture state. For example, processor 80 may automatically adjust the stimulation amplitude to a desired value according to a specific rate of change any time IMD 14 detects that patient 12 is lying down, regardless of the previous posture state.

Although each of the provided examples describes adjusting stimulation amplitude using a rate of change that is specific to one or more factors, such as posture state transition, type of modification (i.e., increase or decrease), or posture state, in some examples, IMD 14 may be configured to adjust stimulation amplitudes using a length of the transition period that is specific to one or more factors, such as those described. For example, rather than adjusting a value of a stimulation parameter according to the same rate of change for all decreases in stimulation amplitude, IMD 14 may be configured to make any adjustment that is a decrease in stimulation amplitude over approximately the same time period. In such cases, the rate of change of the stimulation amplitude parameter from the initial to desired parameter value during the specified time period may be dependent on the overall difference between the initial and desired value, given the same period of time over which the change is to be made. In this manner, different transitions may be associated with different ramp rates, which are determined a function of the length of the time period and the magnitude of the amplitude change to be achieved over the time period.

The above examples present a wide variety of techniques for providing different modification profiles when a transition from one posture state to another posture state is detected. Such examples are provided for purposes of illustration and should not be considered limiting of the techniques as broadly described in this disclosure.

Referring again to FIG. 12, as previously mentioned, patient 12 occupies the upright and active posture state during time periods 224, 226, and 228. Once IMD 14 has increased the amplitude parameter value to second amplitude value 238 at approximately the end of transition period 226, the amplitude parameter is maintained at approximately value 238 throughout time periods 228 and 230. At time 246, patient 12 transitions to a posture state that corresponds to a stimulation therapy program specifying an amplitude parameter with third amplitude value 248. For example, the patient may transition from upright and active to a posture state corresponding to patient 12 in the lying position.

Processor 80 of IMD 14 detects the posture transition of patient 12 from upright and active to lying during dwell time period 230, e.g., in a manner similar that described with respect to the posture state transition detection during dwell time period 224. Once processor 80 has detected the posture transition of patient 12, processor 80 may automatically modify the stimulation therapy, e.g., to effectively address the symptoms experienced by patient 12 while in the lying posture. As illustrated by line 212, the stimulation therapy modification may include decreasing the amplitude parameter value from second amplitude 238 to third amplitude value 248. For example, processor 80 may control stimulation generator 84 to decrease the amplitude of stimulation pulses delivered to patient 12 from second amplitude value 238 to third amplitude value 248, where the third amplitude value 248 is associated with the current patient posture state. Processor 80 may determine that a stimulation amplitude equal to that of third amplitude value 248 is appropriate based on one or more stimulation programs stored in memory 82 that correspond to the posture state of lying down. Patient 12 continues to occupy a lying down posture state during time period 234, in which IMD 14 continues to deliver stimulation therapy to patient 12 at amplitude value 248.

As indicated by the chart shown in FIG. 12, processor 80 controls stimulation generator 84 to adjust the stimulation parameter from second amplitude value 238 to third amplitude value 248 during time period 232 according to a modification profile that specifies the rate of change defined by the slope of portion 250 of line 212. In particular, the rate of change during time period 232 is approximately the negative of the absolute amplitude represented by line 252 divided by the amount of time represented by transition period 232, i.e., the slope of portion 250. Similar to portion 244 of line 212, the rate of change associated with portion 250 may be stored as a value in a look-up table in memory 82, and correspond to stimulation amplitude adjustments associated with a specific posture state transition from upright and active to lying down. In this manner, upon detecting that patient 12 has changed from upright and active to lying down, processor 80 adjusts the stimulation amplitude to a level that provides effective stimulation therapy, and controls the stimulation amplitude adjustment such that the amplitude value is adjusted according to the rate of change specified for the pertinent posture state transition.

In the example shown in FIG. 12, the modification profile for the upright and active to lying down posture state transition presents a slope associated with portion 250 that is much steeper than the slope of portion 244. That is, the modification profile for the upright and active to lying down posture state transition indicates a faster transition period than the modification profile for the upright to upright and active posture state transition. In some cases, an immediate increase or decrease in amplitude or other therapy parameter values may be desirable to mitigate potential patient discomfort that could be caused during a gradual increase or decrease. As previously mentioned, when the posture responsive therapy features of IMD 14 are activated, the transition of patient 12 among different posture states may affect the ability of IMD 14 to deliver consistent efficacious therapy, e.g., because of the response time. As one example, referring to FIG. 1A, the movement of patient 12 to a lying down position may affect the relative positioning of leads 16 with respect to the spinal cord 18 of patient 12.

In some examples, the length of time of transition period 232 may be on the order of seconds or milliseconds. For example, the length of time of transition period 232 may range from approximately 100 milliseconds to approximately 30 seconds, such as approximately 100 milliseconds to approximately 150 milliseconds. In some examples, the length of time of transition period 232 may be substantially equal to that of the length of time required by IMD 14 to process and reconfigure one or more components to deliver stimulation according to respective stimulation amplitude adjustment. In some examples in which the stimulation amplitude value is a voltage amplitude, the amplitude difference represented by line 252 may be on the order of volts or millivolts. In some examples, the amplitude difference represented by line 252 may be up to approximately 10.5 volts. For example, the amplitude difference represented by line 242 may range from approximately one volt to approximately three volts, such as approximately 1.5 volts to approximately two volts.

In some cases, when patient 12 lies down, leads 16 may be compressed towards the spinal cord 18 (FIG. 1A). As a result of the compression of leads 16 toward spinal cord 18, the amplitude of stimulation therapy may need to be decreased relatively quickly to a suitable amplitude value to minimize the possibility of causing patient 12 discomfort or unusual sensations. For example, in some cases, patient 12 may experience what can be described as a "buzz" sensation after lying down due to the compression of one or more leads 16 toward spinal cord 18. Furthermore, because the compression of lead 16 toward spinal cord 18 may substantially coincide with physical movement of patient 12 lying down, it may be desirable to reduce the stimulation amplitude to a suitable value in a relatively short amount of time to avoid patient 12 discomfort.

Consequently, in some examples, the stimulation amplitude may be decreased to a suitable amplitude value within a time period sufficient to prevent the patient from experiencing one or more of the undesirable effects that may result from a patient lying down. In addition, in such cases, it may also be desirable to reduce the delay period component of the dwell time so that the IMD may react more quickly to particular posture state transitions, such as transitions from upright to lying posture states.

In some examples, IMD 14 may automatically decrease the stimulation amplitude according to rate of change that provides for a substantially immediate decrease or drop to a suitable amplitude value when IMD 14 detects that patient 12 lies down, e.g., as shown in FIG. 12. For example, IMD 14 may automatically decrease the stimulation amplitude to a suitable value substantially simultaneously with the detection of patient 12 occupying a lying down posture state. With respect to FIG. 12, such an example is illustrated by portion 250 being substantially vertical. In other words, the amount of time in transition period 232 may be approximately zero. In this example, the time delay between a patient lying down and the decrease to a suitable stimulation amplitude is approximately the amount of time required for IMD 14 to detect that patient 12 is lying down, i.e., time period 230. The substantially immediate drop can be expressed in terms of an abrupt rate of change as determined by an aggressive slope in portion 250 and/or very short transition period 232.

In other examples, the stimulation amplitude may not be decreased substantially immediately by IMD 14, but instead may be decreased to a suitable amplitude value over a period of time that is sufficiently short to prevent patient 12 from experiencing undesirable stimulation effects as a result of receiving stimulation therapy having too high of stimulation amplitude. For example, transition period 232 may define an amount of a time that is less than the amount time in which patient 12 may experience undesirable effects from relating to the patient lying down. As the appropriate transition period may vary from patient to patient, IMD 14 may be programmed with transition period value during a programming session that is defined based on actual patient 12 experiences from therapy delivered by IMD 14 in such a situation.

In some examples, the suitable amplitude value to which IMD 14 decreases stimulation when it is detected that patient 12 lies down may include an amplitude value of zero. By decreasing the amplitude value to zero, it can be ensured that IMD 14 will not supply stimulation to patient 12 at too great of stimulation amplitude. However, in some examples, rather than dropping stimulation amplitude to a value of substantially zero, IMD 14 may decrease the stimulation amplitude to the value defined by the stimulation corresponding to patient 12 occupying a lying posture state, such as illustrated by the stimulation amplitude decrease shown in FIG. 12.

Alternatively, IMD 14 may be programmed to decrease the stimulation amplitude value to a "safe" value that is greater than zero but that is such that patient 12 will not experience any significant negative side effects from the stimulation when lying down. While in some examples the safe value may be the same of the stimulation amplitude value defined by the stimulation program, in some cases it may be different. The safe value may be a preprogrammed value stored in memory 82 of IMD 14 and may be based on one or more factors, such as, e.g., previous patient experience. In some examples, the safe value may be modified after implantation of IMD 14 in patient based on the actual stimulation experiences of patient 12.

In examples utilizing such a "safe" value approach, processor 80 may automatically decrease the stimulation amplitude value to the safe value whenever patient 12 occupies a lying posture state. Alternatively, processor 80 may automatically decrease the stimulation amplitude value to the safe value whenever an adjustment that involves a decrease in stimulation is determined, which may include when patient 12 is lying down, but also other therapy modifications that result in an overall stimulation decrease that are not necessarily as a result of patient 12 lying down.

In some examples, once IMD 14 has decreased the stimulation amplitude value to the safe value in an appropriate amount of time, e.g., to prevent patient 12 from experiencing undesirable side effects, processor 80 may make a further adjustment to the stimulation amplitude value that is defined by the stimulation program that corresponds to the posture state that patient 12 occupies. This amplitude adjustment may be according to a ramp that has a rate of change of different that that employed to make the adjustment to the "safe" value.

For example, IMD 14 may ramp-up/ramp-down the stimulation amplitude from the predetermined safe value to the stimulation value defined by the stimulation program corresponding to patient's 12 posture state. As such, such a technique may have two transition periods associated with the adjustment, the first transition period having a rate of change appropriate for adjusting to the safe value, and the second transition period adjusting to the value defined by the stimulation program corresponding to the patient's detected posture state.

Alternatively, IMD 14 may be programmed to decrease the stimulation amplitude value to any value that is less than a minimum threshold value. This threshold value may represent the minimum amplitude value at which a patient may perceive effects from stimulation regardless of the patient posture state. Similar to described above, this minimum threshold value may be preprogrammed but also modifiable based on patient experience such that the threshold value is patient specific. By lowering the stimulation amplitude value below the threshold value within an appropriate amount of time, patient should not experience any perceivable effects resulting from therapy delivered at too great of stimulation amplitude value.

As another example, if such a threshold value approach is used by an IMD, when the stimulation amplitude value defined by the stimulation program corresponding to a posture state occupied by the patient is less than the minimum threshold value, then the IMD may decrease the stimulation amplitude value to that value in an appropriate amount of time, e.g., substantially immediately, to prevent the patient from experiencing undesirable side effects. However, if the stimulation amplitude value defined by the stimulation program corresponding to the posture state occupied by the patient is greater than or equal to the minimum threshold value, IMD may first decrease the amplitude value to a value less than the threshold, e.g., such as the "safe" value described above, in an appropriate amount of time, e.g., substantially immediately. After that adjustment has been made, the IMD 14 may then adjust to the stimulation amplitude to the value defined by the corresponding stimulation program by ramping up the stimulation at a suitable rate. Accordingly, similar to that described above, such an example may also be described as exhibiting two transition periods.

The rate of change appropriate for one or more adjustments made to the stimulation amplitude may vary from patient to patient. Factors that may influence the effects experienced by patient due to stimulation may include, but are not limited to, the implant location of one or more leads with respect to the spinal cord of a patient and the relative impedance of the tissue separating the one or more leads and the spinal cord. Accordingly, as will be described in further detail below with respect to FIG. 15, in some examples, one or more properties relating to stimulation amplitude adjustments, e.g., the rate of amplitude change, may be tailored to a specific patient.

While the above examples have been described with respect to decreasing stimulation amplitude based on patient 12 occupying a lying down state, e.g., transitioning from upright and active to lying down, in some examples the techniques for decreasing stimulation amplitude may also be applied in any situation in which IMD 14 determines that a stimulation amplitude adjustment that decreases the stimulation amplitude value is warranted. In this manner, patient 12 may be guarded against receiving stimulation therapy from IMD 14 with a pulse amplitude that is too high as a result of a decrease in stimulation amplitude that is too slow.

As described above, a stimulation therapy system may utilize one or more dwell times to determine when to modify the stimulation therapy based on the detected patient activity. Again, a dwell time may include one or time periods utilized by IMD 14 to determine if patient 12 has occupied a posture state for an amount of time that merits modification to stimulation based on the posture state. For example, the dwell time may include a detect period and a delay period. Processor 80 of IMD 14 may classify a posture state as either being a stable posture state or an unstable posture state. For example, IMD 14 may classify a posture state that has been detected but has not satisfied an associated dwell time requirement as an unstable posture state. Conversely, IMD 14 may classify a posture state that has been detected and also has satisfied an associated dwell time requirement as a stable posture state.

In some examples, processor 80 commences modification of one or more therapy parameters only after a posture state transition results in a stable posture state. For example, processor 80 may detect a first posture transition from active to active and upright, followed shortly thereafter by another posture transition from active and upright to upright. In this type of example, rather than automatically modifying the stimulation therapy when it is detected that patient 12 is active and upright, IMD 14 may classify the posture state as unstable and suspend the modification until the dwell time has passed before modifying the stimulation.

If, after the dwell time has passed, processor 80 detects that patient 12 is still upright and active, IMD 14 may classify the upright and active posture state as a stable posture state and, therefore, modify the stimulation to correspond to the active and upright posture state. However, in a situation such as that described, if patient 12 is no longer active at the end of the dwell time, processor 80 may not modify the therapy because the patient did not occupy the upright and active posture state for a sufficient time for IMD 14 to classify it as a stable posture state. Instead, IMD 14 may continue delivering stimulation therapy according to the most recent stable posture state, i.e., upright. In this manner, IMD 14 may only modify stimulation therapy as defined by the stimulation program associated with a detected posture state when the posture state is recognized as a stable posture state.

However, in some examples, processor 80 is configured to adjust one or more stimulation parameters of stimulation therapy prior to patient 12 occupying a stable posture state. In particular, it is recognized that in some examples, especially those relating to the detection of a posture state by IMD 14 that would result in a decrease in stimulation amplitude according to the specified therapy modification, it may be appropriate for processor 80 to control stimulation generator 84 to decrease the stimulation amplitude before the dwell time has elapsed instead of remaining at stimulation amplitude according to the most recent stable posture state. In such a manner, patient 12 may be prevented from receiving stimulation therapy having a stimulation amplitude that is too high, and potentially uncomfortable.

Consequently, in some examples, processor 80 automatically controls stimulation generator 84 to decrease the stimulation amplitude to a lower amplitude value when posture state module 86 first detects an unstable posture state of patient 12 rather than waiting for the posture state to stabilize upon expiration of the dwell time, or remain at the stimulation amplitude value of the most recent stable posture state. Hence, processor 80 controls stimulation generator 84 to gradually or abruptly drop the stimulation amplitude to a lower amplitude before the dwell time has elapsed in order to reduce the possibility that patient 12 may experience discomfort when patient 12 occupies the next posture state. In some examples, IMD 14 may be configured such that the stimulation amplitude value is adjusted to a lower stimulation amplitude only when the detected, unstable posture state defines a stimulation amplitude value that is lower than the amplitude value for the most recent stable posture state.

Hence, in summary, IMD 14 may be configured to respond to a transient indication of sensed posture state change during the dwell time by switching to the lower therapy level (or temporarily turning off therapy) in any instance where the sensed parameter indicates that the patient is transitioning to a posture state (posture or posture/activity) that is associated with lower intensity of therapy (e.g., as indicated by a lower amplitude, frequency, signal duration, and the like). This provision may be added to compensate for the necessary lag between initial sensing of the posture state transition, i.e., a change in the sensed posture state, and expiration of the dwell time. If upon expiration of the dwell time, processor 80 concludes that the sensed posture state change indicates a stable posture state, processor 80 does not further adjust therapy.

Because processor 80 may be unable to predict prospective posture changes in posture of patient 12 and there may be transient or dynamic sensed posture parameters that are misinterpreted as change in posture, and it may be desirable for IMD 14 to respond to each dynamic or transient sensed event with a therapy change, there is a lag produced by the dwell time between the sensed event and the therapy change caused by the system in response to that sensed event. Therefore, for patient comfort, the IMD may provide the feature of turning down or turning off the amplitude during the dwell time when the posture state transition would result in occupation of a posture state for which amplitude would be reduced, to the previous posture state. In this manner, the IMD may reduce therapy intensity, e.g., by reducing amplitude, when there might be a risk that during the transient period, i.e., the dwell time, the patient may be subject to therapy levels that might cause discomfort.

Figure 13:
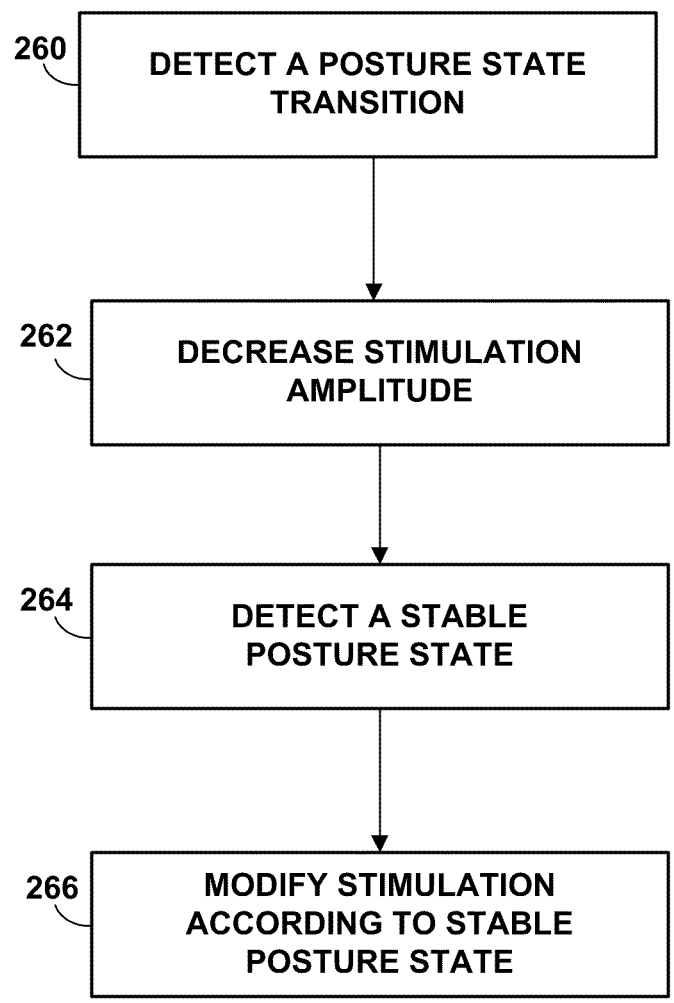
FIG. 13 is a flow diagram illustrating an example technique for adjusting stimulation amplitude based on a patient posture state.

FIG. 13 is a flow diagram illustrating an example technique for adjusting stimulation amplitude based on a patient posture state. In particular, IMD 14 may be configured to automatically decrease a stimulation amplitude of stimulation therapy when IMD 14 detects that patient has transitioned to an unstable posture state rather than waiting to adjust the stimulation amplitude when IMD 14 detects a stable posture state following expiration of the dwell time.

As illustrated processor 80 of IMD 14 detects that patient 12 has undertaken a posture state transition from a stable posture state (260). For example, processor 80 may detect that patient 12 has transitioned from walking (upright and active) to standing (upright). While processor 80 may determine that the upright posture state is an unstable posture state, e.g., based on a defined dwell time, processor 80 automatically decreases the stimulation amplitude value from the stimulation value that was being delivered while patient 12 occupied an upright and active posture state (262). Such an adjustment may be accomplished according to one or more of the techniques described herein, e.g., by decreasing the amplitude substantially immediately.

In general, the lower stimulation amplitude value may be selected such that the amplitude of the stimulation therapy delivered to patient 12 it not too high, e.g., to avoid possible overstimulation of patient 12. In some examples, the lower amplitude value may be zero. As another example, the lower amplitude value may be based on a minimum perception threshold for the patient. As another example, the lower amplitude value may be the lowest amplitude value defined in any stimulation program stored in memory 82. As another example, the lower amplitude value may be a predetermined safe value as previously described.

As another example, the lower amplitude value may be amplitude value corresponding to the unstable posture state that has been detected. In examples in which processor 80 detects that patient 12 has occupied more than one unstable posture state since the latest stable posture state, e.g., a transition from walking to briefly standing to briefly lying down, processor 80 may control stimulation generator 84 to adjust the stimulation therapy to the lowest amplitude value associated with the multiple unstable posture states.

In any case, stimulation generator 84 may continue delivering stimulation therapy at the lower amplitude value until processor 80 detects that patient 12 is occupying a stable posture state (264). For example, patient 12 may occupy the posture state of standing long enough to fulfill a defined dwell time. Once processor 80 has detected the stable posture state, processor 80 may automatically modify the stimulation therapy based on the stable posture state (266), including adjusting the stimulation amplitude value from the lower amplitude value to which processor 80 adjusted when an unstable posture state was occupied by patient 12 to the stimulation amplitude value as defined by the stable posture state, e.g., as defined by the stimulation program associated with the stable posture state. The adjustment to the desired stimulation amplitude value may be carried out using one or more of the techniques described herein, e.g., ramping during a transition period.

As previously described, the lower amplitude value to which processor 80 automatically decreases when an unstable posture state is detected may be selected to avoid over stimulation of patient 12. However, it is also recognized that in some cases, the lower the amplitude value to which processor 80 transitions therapy delivery upon detection of an unstable posture state, the greater the overall amplitude adjustment is required once a stable posture state is detected. Accordingly, in some examples, the lower amplitude value that processor 80 automatically decreases to upon detection of an unstable posture state may be greater than zero. For example, as previously described, the lower amplitude value may be equal to that of the lowest amplitude value defined by any program stored in memory 82 of IMD 14 (FIG. 4). As another example, as previously described, the lower amplitude may be defined by the lowest amplitude value of an unstable posture state. In this manner, the overall adjustment made to the stimulation amplitude by IMD 14 once patient 12 occupies a stable posture state may be minimized.

While examples of modification profiles have been primarily described as exhibiting substantially linear profiles, i.e., approximately constant rate of change over the transition period, example modification profiles are not limited as such. In some example, a modification profile may exhibit a non-linear profile over all or portions of a transition period. For example, a modification profile may define an adjustment such that the rate of change exponentially increases over first portion and then exponentially decays over a last portion such that the stimulation amplitude value gradually approaches the final amplitude value after initially changing at a relative high rate. Furthermore, in some examples, a modification profile may be defined for each of a plurality of sub-periods that make up an overall transition period. For example, a transition period having a length of approximately X seconds may be divided equally into 10 sub-periods, each being approximately one-tenth of X seconds in length. In such cases, a specific rate of change may be defined for each sub-period, such that the modification profile exhibits up to 10 different rates of change over the entire transition period. Using such techniques, a modification profile may be further tailored, e.g., based on specific patient experience, therapy type, and the nature of the amplitude adjustment. In any case, examples of the disclosure are not limited to modification profiles which exhibit a substantially linear profile over a transition period.

Furthermore, although examples of the disclosure may be described as automatically adjusting stimulation amplitude according to the posture state of patient 12 detected by posture state module 86, in some examples, IMD 14 may be configured to adjust stimulation as described herein based on patient input, e.g., sent via programmer 30. In particular, IMD 14 may be configured to receive an indication from patient 12, e.g., via an external programmer, that patient 12 is about to enter or has recently undertaken a lying posture state. Upon receiving this indication, processor 80 of IMD 14 may decrease the stimulation amplitude value in one or more ways that has been described with respect to the detection of a patient transitioning to a lying posture state. In one example, patient 12 may communicate a prospective transition into a lying posture state to IMD 14 by depressing a single button on patient programmer 30 before undertaking the lying posture state. In response, processor 80 may substantially immediately decrease the stimulation amplitude to a value appropriate to be delivered to the patient when lying down. In this manner, IMD 14 may appropriately decrease the stimulation amplitude when patient 12 enters a lying posture state according to a patient-directed adjustment rather than a posture state transition detected by a posture state module.

As previously described, a clinician programs IMD 14 (e.g., after implantation of IMD 14 within patient 12), for therapy delivery on a chronic (e.g., a nontemporary and indefinite) basis. When the posture responsive therapy features of IMD 14 are activated, the clinician may not have direct control over the therapy parameter values with which IMD 14 actually generates and delivers therapy because IMD 14 is programmed to dynamically change one or more therapy parameter values based on a detected patient posture. Thus, the tendency of a clinician during a programming session may be to deactivate the posture responsive therapy mode of IMD 14 during a programming session in order for the clinician to maintain control over the actual therapy parameter values delivered to patient 12. Deactivating the posture responsive therapy mode of IMD 14, however, may result in the failure to test features of the posture responsive therapy mode, such as the modification profiles with which IMD 14 switches between therapy programs (e.g., as described with respect to FIG. 12) and the posture state definitions (e.g., the orientation of a reference coordinate vectors used to define one or more posture cones or otherwise associated with posture states). When IMD 14 is in a programming mode, only a static evaluation of therapy delivery is performed for one or more posture states, regardless of how patient 12 arrived at that posture.

In some cases, IMD 14 is programmed during a programming session that takes place at the clinic. The programming session differs from a therapy session, during which, for example, patient 12 leaves the clinic and goes about normal daily activities while IMD 14 delivers therapy in the manner programmed during the programming session. Regardless of where the programming session takes place, the programming session may be relatively time consuming because the selection of efficacious therapy parameter values for each of a plurality of patient posture states may require several trial and error selections before an efficacious set of therapy parameter values are identified. Thus, it may be inconvenient for patient 12 to continually revisit the clinic to have one or more parameters of the second set of therapy parameters (e.g., modification profile, posture cones or hysteresis zones) adjusted. Accordingly, it may be desirable to trial (e.g., deliver test therapy) the posture responsive therapy features of IMD 14 during the programming session.

In accordance with techniques described herein, a programming session during which IMD 14 is programmed includes at least two phases. In a first phase, the posture responsive therapy mode of IMD 14 is deactivated (e.g., temporarily suspended), and values for a first set of therapy parameters are selected and/or otherwise modified based on trial therapy delivery with the first set of therapy parameter values. In a second phase, the posture responsive therapy mode of IMD 14 is activated, and a second set of therapy parameter values are programmed based on the efficacy of the posture responsive therapy provided by IMD 14 during the second phase. In this way, the responsiveness of therapy delivery by IMD 14 to accommodate different patient postures may be trialed during the programming session, thereby eliminating at least one clinic visit for patient 12. The second phase of the programming session provides an active, posture responsive evaluation for posture state transitions instead of just static evaluation in each posture, as is done in the first phase of the programming session.

Programmer 20 provides a user interface that includes a posture responsive therapy test feature. That is, programmer 20 includes a programming feature that enables the posture responsive therapy mode of IMD 14 to be deactivated and activated during a programming session.

In the absence of activating the posture responsive therapy mode of IMD 14 during the programming session, patient 12 may require a subsequent visit to the clinic in order to modify one or more therapy parameter values related to the responsiveness of IMD 14 to provide posture responsive therapy (referred to herein as the second set of therapy parameters). These therapy parameters may include, for example, the modification profiles or posture state definitions, e.g., as defined by posture cones and hysteresis zones.

FIGS. 14A and 14B are flow diagrams of an example programming technique. If the posture responsive therapy mode of IMD 14 is active when the clinician initiates the programming session, the clinician may deactivate the posture responsive therapy mode (270). In some examples, the clinician utilizes programmer 20 (e.g., clinician programmer 60) to control the activation and deactivation of the posture responsive therapy mode of IMD 14. Example user interfaces that may be presented by programmer 20 to activate and deactivate the posture responsive therapy mode of IMD 14 is described with respect to FIGS. 17A and 18.

In some examples, the posture responsive therapy mode of IMD 14 is automatically deactivated upon the initiation of a programming session with IMD 14 by programmer 20. For example, IMD 14 may automatically deactivate the posture responsive therapy mode and enter a programming mode upon receiving a signal from programmer 20 that indicates a programming session has been initiated. The signal that indicates a programming session has been initiated may include, for example, a communication signal that merely indicates that the programming session was initiated or a programming signal indicating one or more therapy parameter values for implementation by IMD 14. As described below, during the programming session, the clinician may select one or more therapy parameter values (e.g., as individual parameter values or as part of a therapy program) for trialing by IMD 14. In some examples, clinician may manually select the one or more therapy parameter values, while in other examples, the clinician selects the therapy parameter values with the aid of a guided programming technique (e.g., decision trees or a genetic algorithm). Thus, upon receiving an indication of the selected therapy parameter values for trialing via telemetry circuit 88 (FIG. 4), processor 80 of IMD 14 may automatically deactivate the posture responsive therapy mode.

While IMD 14 is in a programming mode, during which processor 80 does not automatically select one or more therapy programs based on a patient posture state determined by posture state module 86 (FIG. 4), the clinician selects a first set of therapy parameter values during a first phase of the programming session (271). For example, the clinician may manually specify parameter values using any suitable technique, such as guided programming techniques (e.g., decision trees, genetic algorithms, and the like), knowledge from past experience program IMDs, and the like. The first set of therapy parameters includes values that define the electrical stimulation signal generated by stimulation generator 84 (FIG. 4) and delivered to patient 12. For example, during the first phase of the programming session, the clinician may select a combination of electrodes carried by one or more implantable leads, and assign polarities to the selected electrodes. In addition, the clinician may select an amplitude, which may be a current or voltage amplitude, and, in the case of therapy delivery by stimulation pulses, a pulse width, and a pulse rate for stimulation pulses to be delivered to the patient.

While posture state module 86 within IMD 14 may continue to sense the posture of patient 12 during the first phase of the programming session, IMD 14 does not automatically modify therapy parameter values based on the detected patient posture. Instead, IMD 14 generates and delivers therapy to patient 12 based on therapy parameter values selected by the clinician (or another user) via programmer 20. The deactivation of the posture responsive therapy mode of IMD 14 enables the clinician to deliver test stimulation to patient 12 according to a clinician-selected therapy program without IMD 14 circumventing the selected therapy parameters. Programmer 20, automatically or with the aid of a clinician, may control IMD 14 to deliver therapy to patient 12 with a selected set of therapy parameter values. The clinician may direct patient 12 to assume a particular posture state to see if a selected set of therapy parameter values are effective for that posture.

During the first phase of the programming session, the clinician may also define the posture state definitions with which IMD 14 automatically determines patient posture states. In some examples, the clinician may instruct patient 12 to undertake a plurality of posture states, and, while in each of the posture states, the clinician may determine the output of the posture sensor and associate the output with the respective posture state. The output from the posture sensor may be used to determine the posture state definitions. For example, the posture sensor output when patient 12 is in a known posture may define a reference coordinate vector (e.g., center lines 153A, 153B, 153C in FIG. 8B or vectors 159, 161, 163, 165, 167 in FIG. 8C) for one or more posture states. In some examples, the clinician defines at least one posture cone based on a reference coordinate vector, as described with reference to FIGS. 8A-8C. Other types of posture state definitions are contemplated in addition to posture cones, such as posture toroids.

The clinician may manually define the posture states or define the posture state definitions with the aid of a computing device, such as programmer 20. The posture state definitions may be stored in memory 82 of IMD 14 (FIG. 4), memory 108 of programmer 20 (FIG. 6) or a memory of another device. Other techniques for determining posture state definitions with which IMD 14 detects patient postures are contemplated.

Prior to or after determining the posture state definitions, the clinician tests a plurality of therapy parameter values in order to select a first set of therapy parameter values that provide efficacious therapy to patient 12 for each of a plurality of patient postures. For example, the clinician may select a therapy program (e.g., with the aid of a guided programming technique), which may be stored within programmer 20 or IMD 14, and instruct IMD 14 to generate and deliver therapy to patient 12 according to the selected therapy program (272). Alternatively, the clinician may select specific therapy parameter values, rather than a group of therapy parameter value stored as a therapy program, to select the first set of therapy parameter values. In this way, deactivating the posture responsive therapy mode of IMD 14 enables the clinician to have direct control over the therapy parameter values with which IMD 14 actually generates and delivers therapy. In other examples, in addition to or instead of clinician generated therapy parameter sets, in some examples, the therapy parameter sets may be selected by patient 12.

Based on the trial therapy delivery with the selected values for the first set of therapy parameters, the clinician determines whether the selected values provide efficacious therapy to patient (273). The efficacy of the stimulation parameters may be determined by receiving input from patient 12 and/or based on one or more physiological parameters of patient 12 monitored by one or more physiological sensors.

The clinician may determine efficacious values for the first set of therapy parameters for each of a plurality of patient posture states, such as the upright, upright and active, lying front, lying back, lying right, and lying left states. The clinician may associate the selected values for the first set of therapy parameters with the patient posture states and store the information in memory 82 of IMD 14 and/or memory 108 of programmer 20. In some examples, the clinician selects values for the first set of therapy parameters and subsequently associates the values with a patient posture state for which the stimulation parameter values provide efficacious therapy. In other examples, the clinician selects a patient posture state and subsequently selects the values for the first set of therapy parameters that provide efficacious therapy for the selected patient posture state. In either example, a set of therapy parameter values may be stored as a therapy program in a memory 82 (FIG. 4) of IMD 14, memory 108 (FIG. 6) of programmer 20, and/or a memory of another device. When the posture responsive therapy mode of IMD 14 is active, processor 80 of IMD 14 delivers therapy to patient 12 by determining a detected patient posture state and the first set of therapy parameter values associated with the posture state in memory 82, 108.

If the selected values for the first set of therapy parameters do not provide efficacious therapy to patient 12 (273), new values may be selected (271) and tested (272). After determining that the selected values for the first set of therapy parameters provide efficacious therapy to patient 12 (273), the clinician activates the posture responsive therapy mode of IMD 14 (274). In some examples, the clinician utilizes programmer 20 (e.g., clinician programmer 60) to activate the posture responsive therapy mode of IMD 14. An example user interface that may be presented by IMD 14 to activate and deactivate the posture responsive therapy mode of IMD 14 is described with respect to FIGS. 17A and 18. In some cases, the posture responsive therapy mode may be referred to as such, or may be more generally referred to as a "trial chronic therapy mode" or another label that indicates that IMD 14 is in a therapy mode in which all features useful for chronic therapy delivery, including the posture responsive therapy features, are active and automatically controlling therapy delivery. In general, activating the posture responsive therapy features may indicate to processor 80 of IMD 14 that processor 80 should control therapy delivery to patient 12 with the chronic therapy delivery techniques, including posture responsive therapy delivery. IMD 14 may be in one of the programming or the posture responsive therapy modes at a time.

During the second phase of the programming session, while patient 12 is in the clinic, patient 12 trials the posture responsive therapy mode of IMD 14. That is, upon activating the posture responsive therapy mode, IMD 14 automatically controls therapy delivery to patient 12 based on a detected patient posture. During the second phase, IMD 14 delivers posture responsive therapy to patient 12 with the values for the first set of therapy parameter values selected during the first phase of the programming session, and the currently stored values for the second set of therapy parameter values (276). The second set of therapy parameters includes the modification profiles for each posture transition. As discussed with reference to FIG. 12, the modification profile includes a dwell time and a transition period and/or a ramp rate for switching between therapy parameter values. If the modification profile includes both a transition period and ramp rate, either the ramp rate or transition period may be fixed and the other may be variable. As previously indicated, in some cases, the ramp rate may depend on the transition period or dictate the transition period, and likewise, the transition period may depend on the ramp rate or dictate the ramp rate. In addition, the second set of therapy parameters includes the definitions of posture states with which posture state module 86 (FIG. 4) of IMD 14 determines a patient posture state. In some cases, the patient posture states may be defined by reference coordinate vectors and at least one posture cone, e.g., as described with respect to FIGS. 8A-8C, and, in some examples, hysteresis zones between the posture cones.

The current values for the second set of therapy parameter values that are stored in memory 82 of IMD 14 may be initially selected using any suitable technique. In some examples, the clinician selects the initial values for the second set of therapy parameters based on the patient condition and/or past experience programming similar IMDs. In other examples, IMD 14 may be programmed by the manufacturer with initial values for the second set of therapy parameter values.

During the second phase of the programming session, patient 12 may undergo various posture state transitions in order to test and assess the efficacy of the posture responsive therapy features of IMD 14. The second set of therapy parameter affect how IMD 14 transitions between therapy programs for the different patient postures, and, therefore, the responsiveness of IMD 14 to posture changes. Efficacy of therapy delivery by IMD 14 may not only be based on the actual parameters of the stimulation signals, but the manner in which IMD 14 switches between therapy programs when a change in patient posture is detected.

Activating the posture responsive therapy features of IMD 14 allows the clinician to determine, during the same programming session during which the first therapy parameter values are selected, whether the current dwell time duration, transition period duration, and/or other modification profile settings result in efficacious shifting between therapy programs to accommodate different patient posture states. In addition, activating the posture responsive therapy features of IMD 14 allows the clinician to assess whether the current definitions of the posture cones (e.g., the orientation of the reference coordinate vector that is determined while patient 12 is known to be in a specific position, as described above with respect to FIGS. 8A-8C) accurately capture the patient's posture states.

As previously indicated, the posture states may be defined by a plurality of posture cones that are each associated with a respective patient posture states and each define values of an output from the posture state sensor that indicate the respective patient posture state. Thus, the posture state definitions may be determined based on a posture reference coordinate vector (e.g., vertical axis 141 and horizontal axis 143 in FIG. 8A) and a distance or angle defining a range of coordinate vectors for the posture cone or a range of cosine values computed using the reference coordinate vector as an adjacent vector and any of the outermost vectors of the cone as a hypotenuse vector, which are determined during the first phase of the programming phase.

The definition of patient posture states affects the responsiveness with which IMD 14 delivers posture responsive therapy to patient 12 because the therapy parameters with which stimulation generator 84 generates and delivers the therapy depends upon the patient posture state detected by posture state module 86. Posture state module 86 determines a patient posture state by associating the output from a posture sensor with a patient posture state based on the stored patient posture state definitions. If the posture state definitions inaccurately reflect the actual patient posture state, posture state module 86 may determine the patient posture state to be an incorrect posture, and processor 80 may select a therapy program associated with the incorrect patient posture state, which may not provide efficacious therapy to patient 12 for the actual patient posture state.

A clinician may determine the effects of the currently selected second set of stimulation parameter values with the first set of stimulation parameter values (277), which were selected during the first phase of the programming session. For example, the clinician may monitor the efficacy of the posture responsive therapy based on patient input and/or based on one or more physiological sensors that generate signals indicative of a physiological parameter of patient 12 that indicates the efficacy of therapy. If the posture responsive therapy with the currently selected second set of stimulation parameter values provides efficacious therapy to patient 12, the clinician may not take any further action (278). The currently stored values for the second set of therapy parameters may be maintained for chronic posture responsive therapy delivery to patient 12.

On the other hand, if the posture responsive therapy with the currently selected second set of stimulation parameter values does not provide efficacious therapy to patient 12, the clinician may modify the second set of therapy parameter values (279). The clinician may modify the second set of therapy parameter values based on the determined physiological effects of the posture responsive therapy delivery by IMD 14 during the second phase of the programming session. In some examples, the posture responsive therapy mode are deactivated prior to modifying the second set of therapy parameter values, e.g., because the therapy parameter values of IMD 14 are not programmable in the posture responsive therapy mode. In addition, in some cases, at least some parameter values of the first set of therapy parameter values may be modified during the second phase of the programming session, e.g., based on the determined physiological effects of the posture responsive therapy delivery by IMD 14.

Patient 12 may provide input indicative of the efficacy of therapy using any suitable technique. In some cases, patient 12 may provide verbal (or its equivalent in the case of patients that cannot speak) or textual input that indicates whether a particular posture state transition was accompanied by inefficacious therapy. The particular posture state transition may be accompanied by inefficacious therapy if, for example, the detection period and/or delay period of the dwell time for initiating the switch between therapy programs was too long (e.g., resulting in nonresponsive therapy delivery) or too short (e.g., resulting in inappropriate therapy delivery because of a transient patient posture change). As another example, a particular posture state transition may be accompanied by inefficacious therapy if the transition time for switching between therapy programs was too long (e.g., resulting in nonresponsive therapy delivery) or too short (e.g., resulting in patient discomfort). Thus, if patient 12 indicates that IMD 14 did not react quickly enough to modify therapy delivery in response to a posture transition, the clinician may adjust the dwell time or transition period duration.

As other examples, patient 12 may provide verbal (or its equivalent) or textual input that indicates that therapy delivery in a particular patient posture state is not effective. In some cases, this input may indicate that the first set of therapy parameter values, e.g., that define the stimulation signal, should be modified. However, because the first set of therapy parameter values was already determined to provide efficacious therapy to patient 12 during the first phase of the programming session, such a patient input may indicate that the posture state definition does not accurately and precisely capture the patient's actual posture state. In addition, the possibility that the patient condition changed enough to change the results of therapy delivery according to the first set of therapy parameter values is minimal because the first and second phases occur during the same programming session.

The posture state definition may be inaccurate based on the distance or angle defining a range of coordinate vectors within a cone surrounding the posture reference coordinate vector, based on the range of cosine values for a particular posture state cone or the size of a hysteresis zone, or based on the orientation of one or more reference coordinate vectors. For example, posture state module 86 of IMD 14 may determine that patient 12 is in an upright posture state when patient 12 is actually in a lying (front) posture state. As a result, processor 80 may deliver electrical stimulation associated with the upright patient posture state, rather than the actual lying (front) posture state of patient 12. Accordingly, patient 12 may indicate that the therapy associated with the lying (front) posture state is ineffective. The clinician may modify the posture state definitions, such as by resizing or reorienting the posture cones and/or reorienting the reference coordinate vector associated with the known patient position. Resizing the posture cone may include, for example, changing the distance or angle defining the range of coordinate vectors within a cone, changing the range of cosine values for the posture cone. As described with respect to FIGS. 8A-8C, in some examples, posture state definitions may include multiple posture cones or an upright posture cone in combination with lying reference coordinate vectors (FIG. 8C).

IMD 14 may also incorrectly determine a patient posture based on the hysteresis zone. That is, patient 12 may also indicate that a particular posture state is associated with an inefficacious therapy program if the hysteresis zone between posture cones is too large, resulting in a failure to modify therapy when patient 12 undergoes an actual posture transition that merits therapy delivery. For example, with respect to the example shown in FIG. 8B, patient 12 may transition from an upright posture to a reclining posture, which may be between the lying (back) cone 156 and upright posture cone 154. The therapy program associated with lying (back) cone 156 may provide more efficacious therapy for patient 12 than the therapy associated with upright posture cone 154. If patient 12 is between cones 156, 154 while in the reclining posture, processor 80 of IMD 14 may not switch to the therapy program associated with lying (back) cone 156 until patient 12 crosses over into the lying (back) posture state due to the hysteresis zone. As a result, patient 12 may indicate that the reclining posture state was associated with an ineffective therapy program, and the clinician may adjust the size of the hysteresis zone. In other examples, the clinician may define an additional posture cone associated with the reclining posture state of patient 12.

In addition to patient input, the clinician may determine the efficacy of the posture responsive therapy mode based on one or more physiological parameters of patient 12 that are monitored with the aid of one or more implanted or external sensors. Examples of physiological parameters that may indicate efficacy of therapy include, for example, heart rate, respiration rate, brain signals (e.g., determined by an EEG or ECoG), an ECG, body temperature, blood pressure, electrodermal activity (e.g., galvanic skin response or skin conductance response), muscle activity (e.g., EMG), blood flow rate, sweat gland activity, pilomotor reflex (e.g., goose bumps), or the like. If any of the physiological parameters indicate IMD 14 is not providing efficacious posture responsive therapy, the clinician may evaluate whether the posture definitions are accurate and/or modify one or more modification profiles. As discussed above, the one or more physiological parameters may indicate IMD 14 is not providing efficacious posture responsive therapy if, for example, the physiological parameter values fall outside of a target range of values or are greater than a threshold value, or in other cases, less than a threshold value.

Other techniques for evaluating the efficacy of the postures responsive therapy provided by IMD 14 in the second phase of the programming session are contemplated. In addition, other types of modifications to the second set of therapy parameter values that affect the responsiveness of the posture responsive therapy delivery by IMD 14 are contemplated.

In some examples, the posture responsive therapy mode of IMD 14 may only be activated during the second phase of the programming session for a predetermined maximum duration of time. Thus, after a predetermined maximum duration of time has passed after activation of the posture responsive therapy mode of IMD 14, IMD 14 may automatically change operating modes from the posture responsive therapy mode back to a programming mode in which the posture responsive therapy features of IMD 14 are deactivated. In other examples, the second phase of the programming session does not terminate until a clinician intervenes and reverts IMD 14 from the posture responsive therapy mode back to the programming mode.

In some examples, after activation of the posture responsive therapy mode of IMD 14 and prior to expiration of a maximum duration of time for testing the posture responsive therapy mode (if any), the clinician may manually revert IMD 14 back to a programming mode at any time. In other examples, the posture responsive therapy mode of IMD 14 is activated during the second phase of the programming session for at least a predetermined minimum duration of time. The minimum duration of time required for trialing the posture responsive therapy features of IMD 14 may be useful to, for example, providing enough time for patient 12 to undergo different patient posture state transitions. The clinician may also select the predetermined minimum duration of time or the predetermined minimum duration of time may be selected by, e.g., a manufacturer of IMD 14 or programmer 20. In some examples, the predetermined minimum duration of time is about one minute to about 30 minutes or more.

Figure 15:
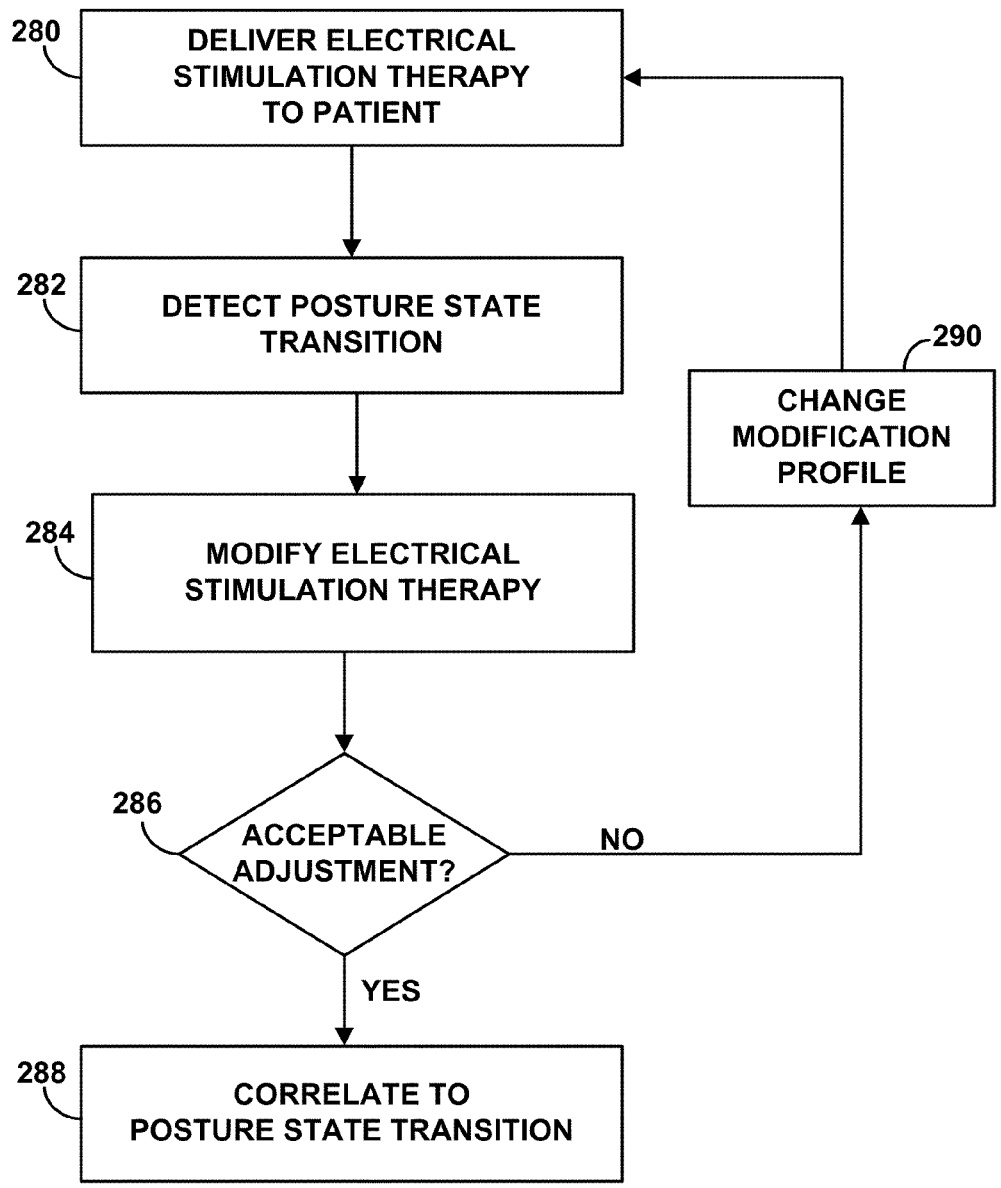
FIG. 15 is a flow diagram illustrating an example technique for configuring one or more properties associated with a stimulation parameter adjustment.

FIG. 15 is a flow diagram illustrating an example technique for configuring one or more properties associated with a modification profile for a stimulation parameter adjustment. For example, such a technique may be utilized to configure the rate of change associated with a stimulation parameter adjustment on a patient-specific basis. Such a technique may be utilized by a clinician during a second phase of a programming session with patient 12 via clinician programmer 60 or, alternatively, may be carried out on a periodic basis by patient 12, e.g., using patient programmer 30.

While IMD 14 is in a posture responsive therapy mode, IMD 14 delivers electrical stimulation therapy having a first stimulation amplitude value to patient 12 (280). In general, the first stimulation amplitude value may be appropriate for the posture state occupied by patient 12 at the time the therapy is delivered. For example, if patient 12 is in an upright posture state, IMD 14 delivers stimulation therapy having a stimulation amplitude value appropriate for when patient 12 is standing. This stimulation amplitude may be determined during the first phase of a programming session. When patient 12 undertakes a posture state transition, processor 80 of IMD 14 detects the posture state transition with the aid of posture state module 86 (282).

Processor 80 modifies the stimulation therapy based on a predetermined modification profile associated with the detected posture state transition. In particular, processor 80 controls stimulation generator 84 (FIG. 4) to modify a therapy parameter value of the electrical stimulation therapy such as amplitude to a value associated with the new posture state (284). The modification may be performed according to a modification profile associated with the particular posture state transition. The modification profile may specify, for example, a rate of change for a ramp to implement the modification of the parameter.

Initially, processor 80 may modify the stimulation parameter (284) according to a default rate of change that is stored by memory 82 of IMD 14 (FIG. 4). The default rate of change may be predetermined based on previous testing specific to patient 12 or for a class of patients with a similar patient condition. As another example, the default rate of change may be predetermined to provide an amplitude adjustment with relatively high efficiency, e.g., with respect to battery consumption. As another example, the default rate of change used may be similar to that used by processor 80 to adjust stimulation amplitude based on other patient posture transitions.

The rate of change that is suitable for a therapy parameter (e.g., amplitude) adjustment may depend on one or more patient specific factors. In accordance with the technique shown in FIG. 15, during the second phase of the programming session when the clinician tests the posture responsive therapy mode of IMD 14, patient 12 may evaluate the acceptability of the therapy parameter adjustment (286) resulting from the therapy modification based on the detected patient activity, e.g., the posture state transition from standing to walking. The modification profile is modified based on the patient evaluation, and, in some cases, input from one or more physiological sensors that indicate the physiological response of patient 12 to the therapy transition.

If the therapy adjustment is determined to be acceptable, e.g., patient 12 indicates that there were substantially no noticeable negative side effects or symptoms experienced during the transition period, then the specific rate of change used to adjust the therapy parameter may be associated with the respective posture state transition on which the therapy modification was based (288), e.g., using one or more suitable techniques to program IMD 14 using programmer 60 or 30. In such a manner, IMD 14 may use the same rate of change in the future when adjusting stimulation amplitude based on a transition from upright to upright and active.

Alternatively, if the adjustment was determined to be unacceptable, e.g., patient 12 experienced one or more negative side effects or symptoms during the transition period, the rate of change value specified by the modification profile and defining the therapy parameter adjustment may be changed (290), i.e., increased or decreased, and the process may be repeated using the new rate of change. A determination of whether the automatic stimulation adjustment was acceptable or not may be determined directly from interaction with the patient or based on one or more sensed physiological parameters.

Figure 17A:
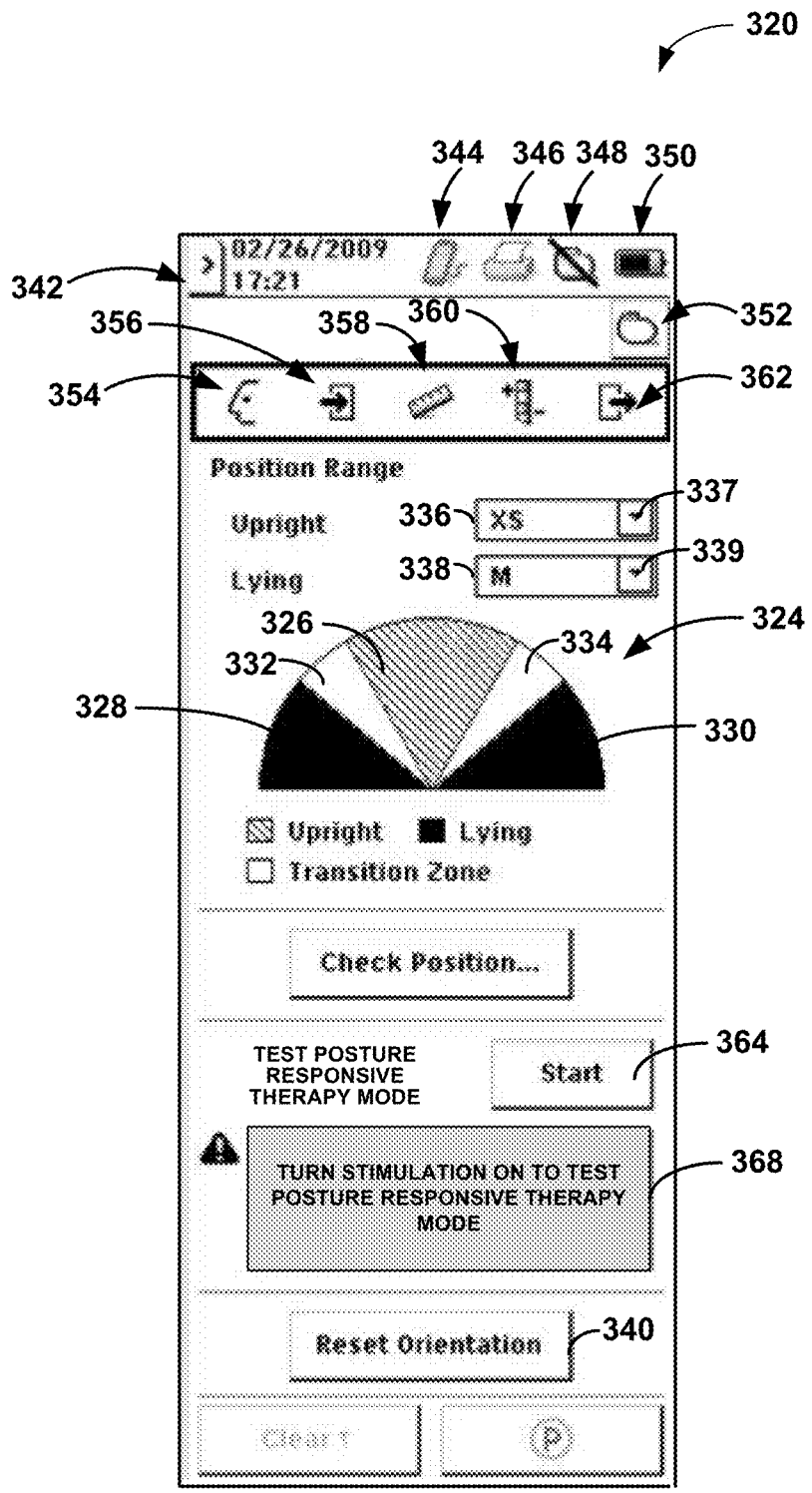
FIGS. 17A, 17B, and 18 are example user interfaces that may be presented to a user via a programmer in order to test a posture responsive therapy mode of an implantable medical device.

In some cases, clinician may change the rate of change value used for amplitude adjustments by communicating with IMD 14 via clinician programmer 60 to specify desired changes to the modification profile that was previously used to modify stimulation delivered to patient 12. FIG. 17A (described below) illustrates a user interface that may be presented by clinician programmer 60 to modify the modification profile associated with various patient posture transitions. In other cases, patient 12 may be allowed to specify changes to the modification profile, e.g., by communicating with IMD 14 via patient programmer 30.

The rate of change value may be changed based at least in part on patient feedback with respect to the previous amplitude adjustment. In some examples, clinician may revise the amplitude rate of change based on experience. For example, if patient 12 experiences physiological effects that are consistent with a rate of change that is too slow, the clinician may increase the rate of change from the previously specified value. Alternatively, if the patient perception of posture responsive therapy is consistent with a rate of change that is too fast, the clinician may decrease the rate of change from the previously specified value. In another example, the rate of change value may be revised based on stimulation efficiency. For example, the revised rate of change value may be the next most efficient rate of change compared to the previously applied rate of change value, which was determined to be unacceptable.

A process such as that illustrated in FIG. 15 may be repeated during the second phase of the programming session at the clinic until an acceptable rate of change is determined for amplitude adjustment for the posture state transition. The clinician may temporarily activate and deactivate the posture responsive therapy mode of IMD 14 as needed with the aid of programmer 20, e.g., using the user interfaces shown in FIGS. 17A and 17B and described below. Further, such a process may be repeated to determine rate of change values specific to one or more different posture state transitions that may result in an adjustment to stimulation amplitude. In this manner, the properties of the stimulation parameter adjustments corresponding to specific therapy modifications may be defined on a patient-specific basis.

Figure 16:
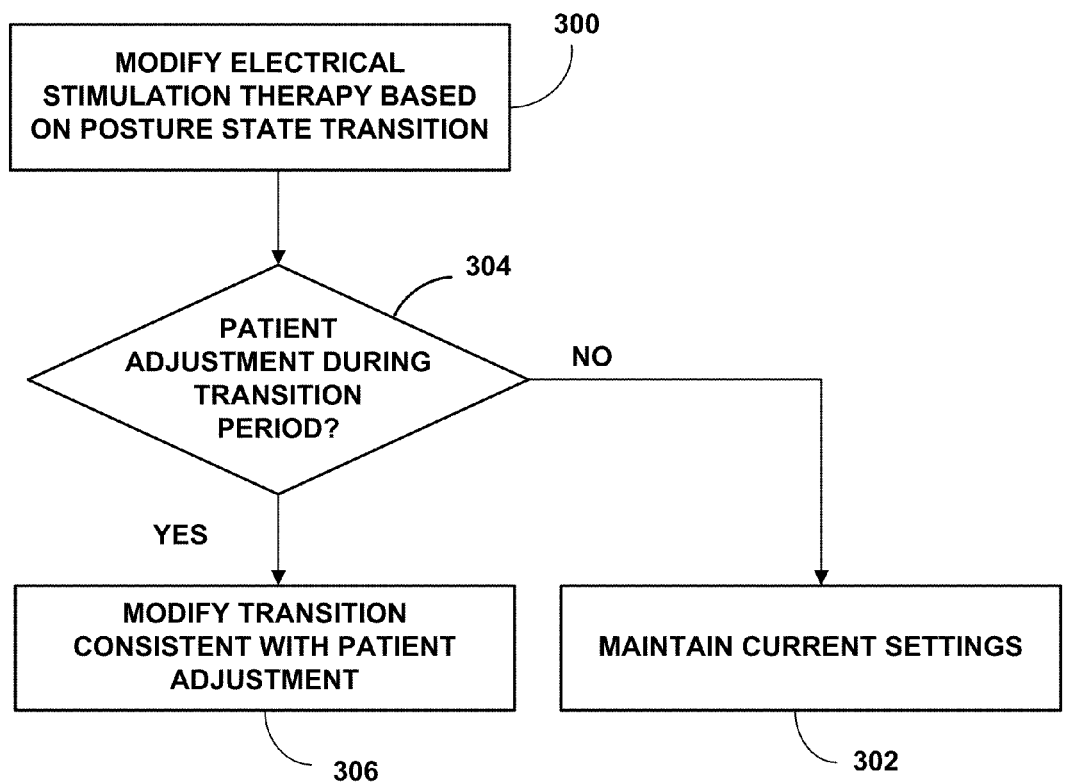
FIG. 16 is a flow diagram illustrating an example technique for configuring a stimulation parameter adjustment based on patient action.

FIG. 16 is a flow diagram illustrating an example technique for configuring a stimulation parameter adjustment based on patient action. Although such a technique may be utilized during a clinician programming session, in some examples, it also may be utilized outside a clinician programming setting. In particular, such a technique may be utilized to continuously or periodically configure one or more properties associated with therapy modifications based on patient activity. In some situations, the suitability of one or more properties associated with a stimulation amplitude adjustment may change over time, e.g., as a result of lead migration within patient 12 and/or fibrosis near one or more implanted leads. For example, as described with respect to FIG. 16, the suitability of the rate of change value associated with one or more stimulation amplitude adjustments carried out by IMD 14 may change from that originally programmed.

Processor 80 of IMD 14 modifies electrical stimulation therapy based on a posture state transition detected by posture state module 86 (FIG. 4) (300). Such a modification may include the increase or decrease of stimulation amplitude. In the posture responsive therapy mode of IMD 14, processor 80 automatically adjusts the stimulation amplitude (or other therapy parameter) according to a specific rate of change specified by a modification profile for a posture state transition. Generally, the stimulation amplitude adjustment may not be perceived by patient 12, or patient 12 may find the respective adjustment to be acceptable at the rate of change over which it is provided. In such cases, IMD 14 will make future stimulation amplitude adjustments according to the programmed rate of change value (302).

However, in some cases, patient 12 provides an indication that the therapy adjustment is not acceptable while processor 80 is in the process of adjusting the stimulation amplitude, i.e., during the transition period. For example, patient 12 may attempt to modify the stimulation amplitude parameter via programmer 30 (304) and, in effect, override the modification profile. As another example, patient 12 may provide input to patient programmer 30 indicating that the therapy adjustment is not acceptable. Based on this patient action, IMD 14 may determine that the existing modification profile is not acceptable to patient 12.

Processor 80 then modifies one or more of the properties associated with the adjustment to the stimulation amplitude consistent with the nature of the patient action (306). For example, in the case of a therapy modification by IMD 14 that increases the stimulation amplitude, if patient 12 attempts to manually increase the stimulation amplitude before the transition period is over, it may be inferred that the adjustment is not being made within an acceptable amount of time, i.e., not quickly enough. In such cases, processor 80 of IMD 14 may automatically modify one or more properties associated with the amplitude adjustment consistent with the attempted patient adjustment (306) to address the apparent shortcoming.

For example, processor 80 may increase the rate of change value specified for the respective stimulation amplitude adjustment such that the adjustment is completed over a shorter period of time, e.g., an amount of time that allows the overall adjustment to be completed prior to the time corresponding to the attempted modification by patient 12. A similar approach may be taken in cases involving a decrease in stimulation amplitude in which patient 12 attempts to manually decrease the stimulation amplitude during the transition period. In this manner, IMD 14 may automatically modify the rate of change value used for stimulation amplitude adjustments based on patient action.

As described with respect to the technique shown in FIG. 16, a determination of whether an automatic stimulation adjustment resulting from a posture transition detected by IMD 14 was acceptable or not may be inferred from patient action or inaction. If patient 12 made a further adjustment during the transition period, it may be inferred that the rate of the posture responsive therapy adjustment was not acceptable and that the modification profile for the associated posture state transition should be modified, e.g., by automatically adjusting the slope of the ramp, if applicable. If patient 12 did not make any further adjustment, it may be inferred that the automated adjustment was acceptable.

In some examples, rather than automatically modifying the rate of change value for the stimulation amplitude adjustment when a patient attempts to modify the stimulation during a transition period, IMD 14 may instead flag the patient adjustment and store the information in memory 82. This information may later be accessed by a clinician, who may then determine whether the rate of change value used by IMD 14 should be changed. In this case, the adjustment of the modification profile is not automatic, but rather clinician-supervised. In other examples, IMD 14 may automatically modify the rate of change value similar to that described, but only after a specific amount of flagged patient adjustments have been made during the respective stimulation period.

In some examples, patient 12 may attempt to adjust the stimulation amplitude parameter during a dwell time period, e.g., such as dwell time 224 of FIG. 12, following a posture state transition. For example, patient 12 may transition between posture states and then attempt to modify the stimulation amplitude via patient programmer 30 before the dwell time period has expired. In such cases, IMD 14 may be configured to recognize such a situation and respond to the situation in an appropriate manner. In some examples, IMD 14 may respond by beginning the stimulation amplitude adjustment according to the corresponding modification profile as if the dwell time had expired at the point when IMD 14 (or programmer) detected that the patient attempted to modify the stimulation amplitude.

In other examples, IMD 14 may respond by adjusting the stimulation to the final stimulation amplitude value substantially immediately and/or at an appropriate rate of change, rather than according the modification profile corresponding to the posture state transition, upon detecting that the patient attempted to modify the stimulation amplitude. In other examples, IMD 14 may ignore the patient's attempt to adjust the stimulation amplitude and, instead wait for the dwell time to expire and adjust the stimulation amplitude according to the corresponding modification profile at that time. In other examples, IMD 14 may respond by adjusting the stimulation amplitude upward or downward to the value indicated by the patient and stay at that value even when the dwell time expires. In other examples, IMD 14 may respond by adjusting the stimulation amplitude to the value indicated by the patient, but then make a further adjustment from that amplitude value to the final amplitude value programmed for the posture state when the dwell time expires, e.g., according to the modification profile corresponding to the posture state transition.

Figure 17B:
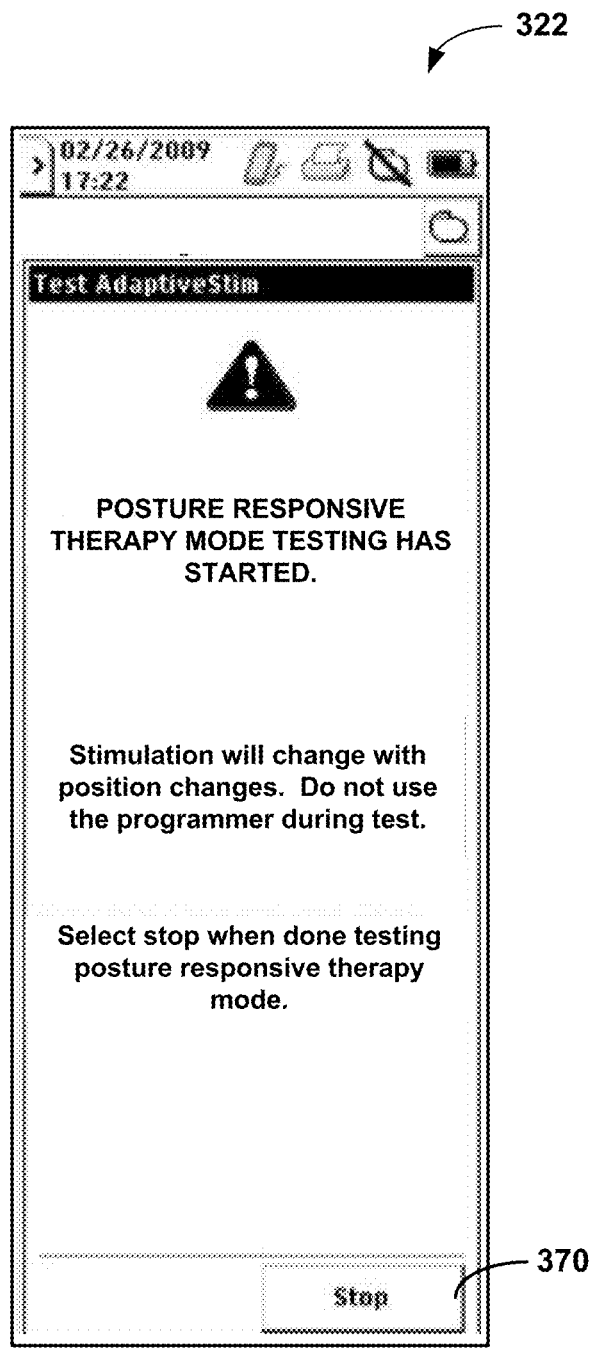

FIGS. 17A and 17B illustrate example user interfaces 320, 322 that may be presented by a medical device programmer. User interfaces 320, 322 are described as generally being displayed by clinician programmer 60. However, user interface 320 may also be displayed by patient programmer 30 or some other external programmer 20 or remote device. A clinician may interact with user interface 320, shown in FIG. 17A, in order to activate or deactivate the posture responsive therapy mode of IMD 14 during a programming session in which the clinician also selects efficacious values for a first set of therapy parameters that define the stimulation signal delivered to patient 12 and associates the selected values with patient posture states.

User interface 320 displays data that indicates the relative size of different posture cones, which define posture states automatically detected by IMD 14 based on the output from a posture sensor of posture state module 86 (FIG. 4). The size of the posture cones may be determined based on the tolerance associated with a defined posture state. As described above with respect to FIGS. 8A-8C, the tolerance may be an angle relative to a coordinate reference vector or a cosine value or a range of cosine values determined based on the reference vector. In the example shown in FIG. 17A, user interface 320 includes a two-dimensional representation of posture state area 324, which is similar to posture state area 140 shown in FIG. 8A, but only represents portions of posture state area 140 indicating the upright and lying postures. In other examples, a three-dimensional illustration of posture state area 324 may be presented via user interface 320. Posture state area 324 includes upright posture cone 326, lying down (back) posture cone 328, lying down (front) posture cone 330, and hysteresis zones 332, 334. In the example shown in FIG. 17A, lying down cones 328, 330 are substantially equal in size.

As described with respect to FIG. 8C, in some examples, the posture state definitions may include an upright cone in combination with lying down reference coordinate vectors that are not necessarily associated with respective lying down posture cones. Thus, in some examples, user interface 320 may only indicate the size of the upright posture cone and permit a user to modify the size of the upright posture cone.

Position range indicator 336 indicates the relative size of upright cone 326, while position range indicator 338 indicates the relative size of each of lying down cones 328, 330.

A clinician or other user may adjust the relative size of posture cones 326, 328, 330 with the aid of pull-down menus 337, 339. For example, the clinician may adjust the size of upright cone 326 by changing position range indicator 336 from extra-small ("XS" as shown in FIG. 17A) to small, medium, or large. Pull-down menu 337 provides the user with the available position range sizes for upright cone 326. Similarly, the clinician may adjust the size of lying down cones 328, 330 by changing position range indicator 338 from medium ("M" as shown in FIG. 17A) to extra-small, small or large with the aid of pull-down menu 339. The designations of the relative posture cone 326, 328, 330 sizes as "extra-small," "small," "medium," and "large" is merely one example of indicating relative posture cone sizes. For example, user interface 320 may alternatively or additionally provide numerical or graphical indications of relative posture cone sizes. Modifying the size of posture cones 326, 328, 330 using the interface shown in FIG. 17A may change the tolerance that is associated with a defined posture value (e.g., may change the angle relative a reference vector or a cosine values that define the tolerance). Modifying the size of posture cones 326, 328, 330 also changes the size of hysteresis zones 332, 334 because of the set area (or volume) of posture state area 324.

In some examples, during the programming session, e.g., in the first phase, the clinician may reset the orientation of the position sensor of posture state module 86 (FIG. 4) of IMD 14 by selecting button 340. In some examples, resetting the orientation of posture sensor may redefine the posture vectors that are stored in IMD 14 for defining the different posture states. The posture vectors are used to, for example, define the relative orientation of posture cones 326, 328, 330 and determine a cosine value for determining which posture state of a plurality of posture states patient 12 currently occupies. In other examples, resetting the orientation of the position sensor of posture state module 86 by selecting button 340 does not redefine posture states (e.g., by reestablishing the reference vectors associated with each patient posture state), but only clears the stored orientation information.

User interface 320 also includes operational menu 342, networking icon 344, printer icon 346, IMD communication icon 348, programmer battery icon 350, stimulation status icon 352, patient data icon 354, data recording icon 356, device status icon 358, programming icon 360, and data reporting icon 362. Operational menu 342 is a button that the user may select to view multiple options or preferences selectable by the user. Operational menu 342 may provide preferences for clinician programmer 60 instead of therapy specific information. Networking icon 344 is shown as grayed out to indicate that clinician programmer 60 is not currently connected to a network. When networking icon 344 is shown fully, clinician programmer 60 is connected to a network. Printer icon 346 indicates when clinician programmer 60 is connected to a printer. When printer icon 346 is grayed out as shown in FIG. 17A, there is no printer connected to clinician programmer 60.

Further, IMD communication icon 348 is shown as indicating that clinician programmer 60 is not in communication with IMD 14 because the icon includes a slash through the IMD representation. The slash is removed when clinician programmer 60 has established a communication link to IMD 14. In addition, programmer battery icon 350 indicates the current charge level of the battery contained within clinician programmer 60. Stimulation status icon 352 indicates to the user when stimulation is being delivered to patient 12. In the example of FIG. 17A, stimulation is not currently being delivered, but stimulation status icon 352 may include an electrical bolt through the IMD representation when stimulation is delivered.

User interface 320 also provides menu options related to stimulation therapy of patient 12. Patient data icon 354 allows the user to enter and review data related to the status of and the condition of patient 12. Data recording icon 356 allows the user to navigate to other screens to enter data recording preferences and review stored data. Device status icon 358 allows the user to view operational status of components of IMD 14, such as electrodes, leads, batteries, and any discovered problems. Programming icon 360 allows the user to navigate to programming screens that define the stimulation therapy parameters used to deliver stimulation to patient 12. In addition, data reporting icon 362 allows the user to view and print reports of the progress of the patient's therapy and other therapy information.

In some examples, the clinician interacts with user interface 320 (e.g., via user input mechanisms provided by user interface 106 (FIG. 6)) in order to activate the posture responsive therapy mode of IMD 14 during a programming session. The clinician may select start button 364 to activate the posture responsive therapy mode of IMD 14. Upon selection of start button 364, processor 104 of clinician programmer 60 (shown in FIG. 6 as processor 104 of programmer 20) transmits a signal to IMD 14 via the respective telemetry circuits 110 (FIG. 6), 88 (FIG. 4) that instructs IMD 14 to activate the posture responsive therapy mode. That is, upon receiving the signal from clinician programmer 60, processor 80 of IMD 14 enters a mode in which processor 80 dynamically adjusts therapy delivery to patient 12 based on a detected patient posture state. In this way, activation of start button 364 may also represent the start of the second phase of a programming session for programming IMD 14. In the example shown in FIG. 17A, user interface 320 presents an alert 368 to the clinician that indicates that stimulation delivery by IMD 14 needs to be activated in order test the posture responsive therapy mode of IMD 14.

After activating the posture responsive therapy mode of IMD 14, processor 104 of clinician programmer 60 may present user interface 322, as shown in FIG. 17B, that indicates that the posture responsive therapy mode testing has started. The example of user interface 322 shown in FIG. 17B also informs the clinician that IMD 14 will modify stimulation therapy as patient position (e.g., posture) changes. This notification helps ensure that the clinician will not attempt to override the posture responsive therapy mode of IMD 14 while the posture responsive therapy mode is tested. After the clinician determines the efficacy of the posture responsive therapy mode of IMD 14, the clinician may select stop button 370, which deactivates the posture responsive therapy mode.

During the second phase of the programming session, the clinician may determine the efficacy of one or more aspects of posture responsive therapy mode of IMD 14 at a time. For example, the clinician may determine the efficacy of the posture state definitions in the second phase. If, after selecting select stop button 370, the clinician determines that the posture state definitions stored by IMD 14 are inaccurate, the clinician may return to user interface 320 shown in FIG. 17A and adjust the relative size of the posture cones 326, 328, 330 or otherwise adjust the posture state definitions. Thereafter, the clinician may select start button 364 (FIG. 17A) and determine the efficacy of the posture responsive therapy mode implemented with the modified posture cone sizes. The clinician may continue to trial different posture state definitions during the second phase of the programming session until the posture state definitions are acceptable.

After defining and storing acceptable posture state definitions, the clinician may determine the efficacy of the modification profiles stored by IMD 14 by selecting values for the dwell time and transition periods, trialing the selected dwell time and transition periods during a subsequent phase in which the posture responsive therapy features of IMD 14 are activated, and, if necessary, modifying the dwell time and transition periods based on the patient input and/or other input provided regarding the efficacy of the posture responsive therapy delivered with the current modification profile settings.

Figure 18:
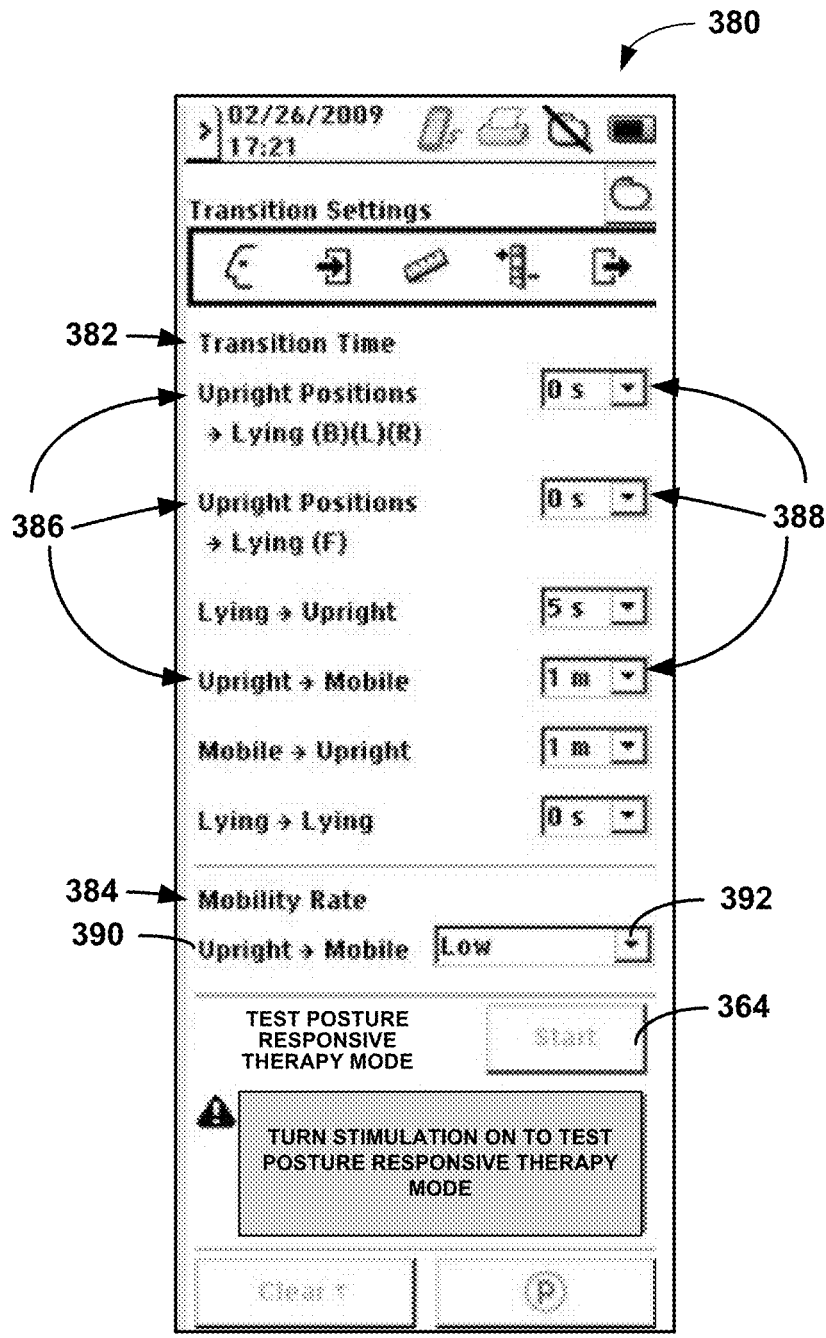

FIG. 18 illustrates an example user interface 380, which includes similar features as user interface 320 (FIG. 17A), but provides an interface that enables a clinician to select various dwell times, rather than posture cones as in user interface 320. User interface 380 includes transition time section 382 and mobility rate section 384. Transition time section 382 includes options with which the clinician may select from different dwell times for different patient posture transitions 386. In the example shown in FIG. 18, the available dwell times are predetermined and may be selected from pull down menus 388 for the respective patient posture transitions 386.

Mobility rate section 384 indicates the relative mobility of patient 12 for the indicated posture state. For example, for an upright and mobile (active) posture state (390), the clinician may select between "low," "moderate," and "high" mobility rates with the aid of pull down menu 392. Other mobility indications may be used, such as a numerical scale. Mobility rate may be, for example, an indication of the activity intensity threshold, such as whether the posture state indicates patient 12 is walking, jogging or running. In some examples, the mobility rate (e.g., activity level) associated with a posture state may affect the detection of the posture state during the dwell time.

After selecting dwell times (shown as "transition time" in FIG. 18) for each of the posture state transitions provided by user interface 380, the clinician may determine the efficacy of the posture responsive therapy delivery with the selected dwell times by testing the posture responsive therapy mode of IMD 14. In the example shown in FIG. 18, the clinician may select start button 364 in order to activate the posture responsive therapy mode of IMD 14. After the activation of the posture responsive therapy mode of IMD 14, patient 12 may physically move between different postures and evaluate the manner in which IMD 14 shifts between therapy programs after the posture transition. Patient 12 may provide input regarding the efficacy of posture responsive therapy delivery with the selected dwell times using any suitable technique, such as verbal input or written input.

If patient 12 indicates that the shift between therapy programs for a particular patient posture state was too slow or too quick, the clinician may return to user interface 380 and modify the dwell time for that posture transition using the pull down menu 388 associated with the posture transition. The dwell time may be perceived by patient 12 as being too slow if patient 12 perceives a shift in therapy, but the duration of time prior to reaching an efficacious therapy for the final patient posture in the posture transition was too long. Patient 12 may perceive the dwell time as being too fast if patient 12 perceives a shift in therapy along with discomfort from a sudden change in therapy parameters (e.g., amplitude). The clinician may continue to test and modify different dwell times until efficacious dwell times for each posture transition are identified.

In some examples, a techniques for programming a medical device may include, during a programming session, programming one or more therapy parameters of a medical device during a programming session while the medical device is in a first mode, during the programming session, activating a second mode of the medical device to deliver posture responsive therapy to a patient, wherein the posture responsive therapy is suspended while the medical device is in the first mode, and determining an efficacy of the posture responsive therapy based on the delivery of posture responsive therapy during the programming session. In some examples, the technique can include programming one or more therapy parameters of the medical device based on efficacy of the posture responsive therapy delivered to the patient while the second mode of the medical device is activated.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry. In examples in which information processed and presented to a user, the information may be processed and/or presented via a patient or clinician programmer or a computer that communicates with the patient programmer or clinician programmer.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the claims. These and other examples are within the scope of the following claims.

The invention claimed is:

1. A method comprising:
    programming a first set of one or more therapy parameter values of a medical device during a programming session while the medical device is in a first mode, the first set of one or more therapy parameter values being associated with a posture state, wherein programming the first set of one or more therapy parameter values while the medical device is in the first mode comprises programming a first value of a first therapy parameter with which the medical device delivers therapy to the patient;

during the programming session, activating a second mode of the medical device to deliver posture responsive therapy to a patient, wherein the posture responsive therapy is suspended while the medical device is in the first mode, and wherein, while the medical device is in the second mode, the medical device delivers posture responsive therapy to the patient by at least delivering therapy to the patient in accordance with the first set of one or more therapy parameter values in response to detecting the posture state; and programming a second set of one or more therapy parameter values of the medical device based on efficacy of the posture responsive therapy delivered to the patient with therapy parameter values including the first set of one or more therapy parameter values while the second mode of the medical device is activated, wherein programming the second set of one or more therapy parameter values based on efficacy of the posture responsive therapy delivered to the patient while the second mode of the medical device is activated comprises programming a second therapy parameter that differs from the first therapy parameter.

2. The method of claim 1, further comprising receiving input indicative of the efficacy of the posture responsive therapy delivered to the patient while the second mode of the medical device is activated.

3. The method of claim 2, wherein receiving input comprises at least one of receiving patient input or input from one or more sensors indicative of a physiological effect of the therapy.

4. The method of claim 2, wherein programming the second set of one or more therapy parameter values comprises modifying at least one therapy parameter value of the first set of one or more therapy parameter values based on efficacy of the posture responsive therapy delivered to the patient while the second mode of the medical device is activated.

5. The method of claim 1, wherein the first therapy parameter comprises at least one of an amplitude, a frequency, a signal duration, an electrode combination, or a posture state definition with which the medical device automatically determines a patient posture state.

6. The method of claim 1, wherein the second therapy parameter comprises a modification profile with which the medical device transitions between therapy parameter settings in response to detecting a posture state transition.

7. The method of claim 6, wherein the modification profile defines at least one of a dwell time duration between a detection of the posture state transition by the medical device and a modification to the therapy parameter settings made by the medical device, a rate of change of a therapy parameter implemented by the medical device upon detecting the patient posture transition, or a transition period of time over which the medical device adjusts a therapy parameter upon detecting the posture state transition.

8. The method of claim 6, wherein the modification profile defines a dwell time duration between the posture state transition by the patient and a modification to the therapy parameter settings made by the medical device.

9. The method of claim 1, wherein the second therapy parameter comprises a posture state definition with which the medical device automatically determines a patient posture state.

10. The method of claim 1, further comprising:
    receiving input indicative of an efficacy of therapy delivered to the patient while the medical device is in the first mode; and modifying the first therapy parameter value based on the input indicative of the efficacy of therapy, wherein programming the second set of one or more therapy parameters of the medical device based on efficacy of the posture responsive therapy delivered to the patient while the second mode of the medical device is activated comprises modifying the second therapy parameter value based on the efficacy of the posture responsive therapy, wherein the second therapy parameter value is not modified based on the efficacy of the therapy delivered to the patient while the medical device is in the first mode.

11. The method of claim 1, wherein programming the first set of one or more therapy parameter values while the medical device is in the first mode and programming the second set of one or more therapy parameter values based on efficacy of the posture responsive therapy delivered to the patient while the second mode of the medical device is activated comprises programming values for one or more common therapy parameters.

12. The method of claim 1, wherein the patient is present at a clinic during the programming session and activating the second mode of the programming session of the medical device comprises temporarily activating a chronic therapy delivery mode of the medical device while the patient is present at the clinic.

13. The method of claim 1, further comprising automatically deactivating the second mode of the medical device after a predetermined duration of time.

14. A system comprising:
a medical device that includes a first mode and a second mode in which the medical device automatically delivers posture responsive therapy to a patient, wherein the posture responsive therapy is suspended when the medical device is in the first mode; and
a processor that, during a programming session, programs a first set of one or more therapy parameter values of the medical device while the medical device is in the first mode, the first set of one or more therapy parameter values being associated with a posture state, and activates the second mode of the medical device to activate posture responsive therapy delivery to the patient, wherein, while the medical device is in the second mode, the medical device delivers posture response therapy to the patient by at least delivering therapy to the patient in accordance with the first set of one or more therapy parameter values in response to detecting the posture state, and wherein the processor programs a second set of one or more therapy parameter values of the medical device based on efficacy of the posture responsive therapy delivered to the patient with therapy parameter values including the first set of therapy parameter values while the second mode of the medical device is activated,
wherein the processor programs the first set of one or more therapy parameter values of the medical device while the medical device is in the first mode by at least programming a first value of a first therapy parameter with which the medical device delivers therapy to the patient, and
wherein the processor programs the second set of one or more therapy parameter values of the medical device based on efficacy of the posture responsive therapy delivered to the patient while the second mode of the medical device is activated by at least programming a second therapy parameter that differs from the first therapy parameter.

15. The system of claim 14, wherein the processor automatically deactivates the second mode of the medical device after a predetermined duration of time.

16. The system of claim 14, wherein the processor receives input indicative of the efficacy of the posture responsive therapy delivered to the patient while the second mode of the medical device is activated and determines the efficacy of the posture responsive therapy based on the input.

17. The system of claim 16, wherein the processor receives the input from a user.

18. The system of claim 16, comprising one or more sensors that sense one or more physiological parameters of the patient, wherein the processor receives the input indicative of the efficacy of therapy from the one or more sensors.

19. The system of claim 16, wherein the processor programs the second set of one or more therapy parameter values by at least modifying at least one therapy parameter value of the first set of one or more therapy parameter values based on efficacy of the posture responsive therapy delivered to the patient while the second mode of the medical device is activated.

20. The system of claim 14, wherein the first therapy parameter comprises at least one of an amplitude, a frequency, a signal duration, an electrode combination, or a posture state definition with which the medical device automatically determines a patient posture.

21. The system of claim 14, wherein the second therapy parameter comprises a modification profile with which the medical device transitions between therapy parameter settings in response to detecting a posture state transition.

22. The system of claim 14, wherein the second therapy parameter comprises a posture state definition with which the medical device automatically determines a patient posture state.

23. The system of claim 14, wherein the processor activates the second mode of the medical device by at least temporarily activating a chronic therapy delivery mode of the medical device.

24. The system of claim 14, further comprising a medical device programmer that comprises the processor.

25. The system of claim 14, wherein the medical device comprises the processor.

26. A system comprising:
means for programming a first set of one or more therapy parameter values of a medical device during a programming session while the medical device is in a first mode, the first set of one or more therapy parameter values being associated with a posture state, wherein the means for programming the first set of one or more therapy parameter values while the medical device is in the first mode programs a first value of a first therapy parameter with which the medical device delivers therapy to the patient;
means for activating a second mode of the medical device to deliver posture responsive therapy to a patient during the programming session, wherein the posture responsive therapy is suspended while the medical device is in the first mode, and wherein, while the medical device is in the second mode, the medical device delivers posture response therapy to the patient by at least delivering therapy to the patient in accordance with the first set of one or more therapy parameter values in response to detecting the posture state; and
means for programming a second set of one or more therapy parameter values of the medical device based on efficacy of the posture responsive therapy delivered to the patient with therapy parameter values including the first set of one or more therapy parameter values while the second mode of the medical device is activated, wherein the means for programming the second set of one or more therapy parameter values based on efficacy of the posture responsive therapy delivered to the patient while the second mode of the medical device is activated programs a second therapy parameter that differs from the first therapy parameter.

27. The system of claim 26, further comprising:

means for determining an efficacy of therapy delivered to the patient while the medical device is in the first mode.

\* \* \* \* \*